United States Patent
Bookbinder et al.

(10) Patent No.: US 12,012,597 B2
(45) Date of Patent: Jun. 18, 2024

(54) CANCER TREATMENT USING siRNA TO MODULATE EXPRESSION OF PRDM2/RIZ PROTEIN

(71) Applicant: ARIZ Precision Medicine, Inc., Davis, CA (US)

(72) Inventors: Lonnie L. Bookbinder, Davis, CA (US); Narendra K. Vaish, Kirkland, WA (US); Brad J. Niles, Davis, CA (US); Jonathan Flynn, San Jose, CA (US); Nicole Nunez, Vacaville, CA (US)

(73) Assignee: ARIZ Precision Medicine, Inc., Davis, CA (US)

( * ) Notice: Subject to any disclaimer, the term of this patent is extended or adjusted under 35 U.S.C. 154(b) by 0 days.

(21) Appl. No.: 17/945,739

(22) Filed: Sep. 15, 2022

(65) Prior Publication Data
US 2023/0099879 A1    Mar. 30, 2023

Related U.S. Application Data

(63) Continuation of application No. PCT/US2021/032311, filed on May 13, 2021.

(60) Provisional application No. 63/024,624, filed on May 14, 2020.

(51) Int. Cl.
  *C12N 15/113*    (2010.01)
  *A61P 35/00*    (2006.01)

(52) U.S. Cl.
  CPC ............ *C12N 15/113* (2013.01); *A61P 35/00* (2018.01); *C12N 2310/14* (2013.01); *C12N 2310/16* (2013.01); *C12N 2310/335* (2013.01)

(58) Field of Classification Search
  CPC .............. C12N 15/113; C12N 2310/14; C12N 2310/335; C12N 15/87; C12N 15/88; C12N 2320/31
  USPC ...... 424/9.1; 435/6.1, 91.1, 91.31, 455, 458; 514/44 R; 536/23.1, 24.5
  See application file for complete search history.

(56) References Cited

U.S. PATENT DOCUMENTS

| | | |
|---|---|---|
| 5,811,304 A | 9/1998 | Huang |
| 6,989,245 B2 | 1/2006 | Huang |
| 7,691,997 B2 | 4/2010 | Khvorova et al. |
| 7,820,809 B2 | 10/2010 | Khvorova et al. |
| 7,834,170 B2 | 11/2010 | Khvorova et al. |
| 8,090,542 B2 | 1/2012 | Khvorova et al. |
| 8,680,045 B2 | 3/2014 | Primiano et al. |
| 9,273,316 B2 | 3/2016 | Primiano et al. |
| 9,358,308 B2 | 6/2016 | Primiano et al. |
| 10,111,898 B2 | 10/2018 | Primiano et al. |
| 10,226,424 B2 | 3/2019 | Parette et al. |
| 2005/0116204 A1 | 6/2005 | Moeckly et al. |
| 2005/0244851 A1 | 11/2005 | Blume et al. |
| 2005/0245475 A1 | 11/2005 | Khvorova et al. |
| 2005/0246749 A1 | 11/2005 | Tsuruga et al. |
| 2005/0255487 A1* | 11/2005 | Khvorova ............... A61P 13/12 435/6.16 |
| 2005/0281884 A1 | 12/2005 | Adair et al. |
| 2007/0031844 A1 | 2/2007 | Khvorova et al. |
| 2007/0039072 A1 | 2/2007 | Khvorova et al. |
| 2008/0113351 A1 | 5/2008 | Naito et al. |
| 2010/0247436 A1 | 9/2010 | Adair et al. |
| 2011/0054005 A1 | 3/2011 | Naito et al. |
| 2011/0129413 A1 | 6/2011 | Morgan et al. |
| 2011/0293698 A1 | 12/2011 | Primiano et al. |
| 2012/0052487 A9* | 3/2012 | Khvorova ............... G16B 20/00 536/23.1 |
| 2012/0208742 A1 | 8/2012 | Primiano et al. |
| 2014/0220045 A1 | 8/2014 | Primiano et al. |
| 2015/0165053 A1 | 6/2015 | Parette et al. |
| 2016/0058784 A1 | 3/2016 | Primiano, II et al. |
| 2016/0244501 A1 | 8/2016 | Ellsworth et al. |
| 2017/0073768 A1* | 3/2017 | Shanahan ............... A61K 48/00 |
| 2018/0291400 A1 | 10/2018 | Zhang et al. |
| 2018/0305699 A1 | 10/2018 | Drummond et al. |
| 2019/0345573 A1 | 11/2019 | Khvorova et al. |
| 2022/0267775 A1 | 8/2022 | Bookbinder et al. |

FOREIGN PATENT DOCUMENTS

| | | |
|---|---|---|
| EP | 2213738 B1 | 10/2012 |
| JP | 2015033381 A | 2/2015 |
| WO | WO-9961631 A1 | 12/1999 |
| WO | WO-2005111238 A2 | 11/2005 |
| WO | WO-2006006948 A2 | 1/2006 |
| WO | WO-2008038832 A1 | 4/2008 |
| WO | WO-2011050178 A2 | 4/2011 |
| WO | WO-2012061443 A2 | 5/2012 |
| WO | WO-2015023967 A2 | 2/2015 |
| WO | WO-2021007465 A2 | 1/2021 |
| WO | WO-2021231771 A2 | 11/2021 |

OTHER PUBLICATIONS

Mallikaratchy, P. (Molecules, vol. 22, 215, pp. 1-12 (2017)). (Year: 2017).*

Abbondanza, C. et al., "Identification of a functional estrogen-responsive enhancer element in the promoter 2 of PRDM2 gene in breast cancer cell lines", J Cell Physiol, 2012, vol. 227, No. 3, pp. 964-975.

Altinoglu, E. et al., "Near-Infrared Emitting Fluorophore-Doped Calcium Phosphate Nanoparticles for In Vivo Imaging of Human Breast Cancer", ACS Nano, 2008, vol. 2, No. 10, pp. 2075-2084.

Bass, B., "Double-Stranded RNA as Template for Gene Silencing", Cell, 2000, vol. 101, p. 235.

Bates, P. et al., "G-quadruplex oligonucleotide AS1411 as a cancer-targeting agent: Uses and Mechanisms", Biochimica et Biophysica Acta, 2017, vol. 1861, pp. 1414-1428.

(Continued)

*Primary Examiner* — Jane J Zara

(74) *Attorney, Agent, or Firm* — Wilson Sonsini Goodrich & Rosati

(57) ABSTRACT

Inhibitory RNA molecules that specifically inhibit mammalian RIZ2 expression, with therapeutic effect in cell proliferative diseases, such as cancer.

8 Claims, 10 Drawing Sheets

Specification includes a Sequence Listing.

(56) References Cited

OTHER PUBLICATIONS

Bernstein, E. et al., "Role for a bidentate ribonuclease in the initiation step of RNA interference", Nature, 2001, vol. 409, p. 363.
Casamassimi, A. et al., "Multifaceted Role of PRDM Proteins in Human Cancer", Int J Mol Sci., 2020, vol. 21, No. 2648, pp. 1-46.
Cheedipudi, S. et al. "A fine balance: epigenetic control of cellular quiescence by the tumor suppressor PRDMX/RIX at a bivalent domain in the cyclin a gene", Nucleic Acids Research, 2015, vol. 43, No. 13, pp. 6236-6253.
Chen, G et al, "MRI-visible polymeric vector bearing CED3 single chain antibody for gene delivery to T cells for immunosuppression", Biomaterials, 2009, vol. 30, pp. 1962-1970.
Cheng, H.Y. et al., "Synergism between RIZ1 gene therapy and paclitaxel in SiHa cervical cancer cells", Cancer Gene Ther, 2016, vol. 23, No. 11, pp. 392-395.
Cui, Y. et al, "The unusual yin-yang fashion of RIZ1/RIZ2 contributes to the progression of esophageal squamous cell carcinoma", Open Life Sciences, 2016, vol. 11, pp. 136-141.
Di Zazzo, E. et al, "Critical Function of PRDMZ in the Neoplastic Growth of Testicular Germ Cell Tumors", Biology, 2016, vol. 5, No. 54, pp. 1-12.
Di Zazzo, E. et al., "PRDM Proteins: Molecular Mechanisms in Signal Transduction and Transcriptional Regulation", Biology, 2013, vol. 2, No. 1, pp. 107-141.
Dong, S.W. et al., "Study on RIZ1 gene promoter methylation status in human esphogeal squamous cell carcinoma", World J Gastroenterol, 2012, vol. 18, No. 6, pp. 576-582.
Du, Y. et al., "Hypermethylation in Human Cancers of the RIZ1 Tumor Suppressor Gene, a Member of a Histone/Protein Methlytransferase Superfamily", 2001, Cancer Research, vol. 61, pp. 8094-8099.
Elbashir, S.M. et al., RNA interference is mediated by 21-and 22-nucleotide RNAs, Genes Dev, 2001, vol. 15, pp. 188-200.
Fire et al. Potent and specific genetic interference by double-stranded RNA in Caenorhabditis elegans. Nature 391 (1998): 806-811.
Fog, C.K. et al, "PRDM proteins: Important players in differentiation and disease", Bioessays, 2011, vol. 34, pp. 50-60.
Fumasoni, I. et al., "Family expansion and gene rearrangements contributed to the functional specialization of PRDM genes in vertebrates", BMC Evol Biol, 2007, vol. 7, No. 187, pp. 1-11.
Gazzerro, P. et al, "Modulation of RIZ gene expression is associated to estradiol control of MCF-7 breast cancer cell proliferation", Exp Cell Res, 2006, vol. 312, No. 3, pp. 340-349.
Ge, P. et al., "Aberrant Methylation of the 1p36 Tumor Suppressor Gene RIZ1 in Renal Cell Carcinoma", Asian Pac J Cancer Prev, 2015, vol. 16, No. 9, pp. 4071-4075.
Genbank Accession XR-003719324.1, "Predicted: Macaca mulatta uncharacterized LOC114669949, transcript variant X2, ncRNA", Publication [online] Apr. 26, 2019 [retrieved on Dec. 13, 2022] retrieved from internet: URL: https://www.ncbi.nlm.nih.gov/nucleotide/XR_003719324.1?report=genbank&log$=nucltop&blast_rank=8&RID=PEXF6GH016.
Gyory, I. et al, "Identification of a functionally impaired positive regulatory domain I binding factor 1 transcription repressor in myeloma cell lines", J. Immunol, 2003, vol. 170, pp. 3125-3133.
Hadjipanayis, CG et al., "EGFRvIII antibody-conjugated iron oxide nanoparticles for magnetic resonance imaging-guided convection-enhanced delivery and targeted therapy of glioblastoma", Cancer Res, 2010, vol. 70, No. 15, pp. 6303-6312.
Hamilton, A.J. et al, "A species of small antisense RNA in post-transcriptional gene silencing in plants", Science, 1999, vol. 286, pp. 950-952.
Hammond, S.M. et al., "An RNA-directed nuclease mediates post-transcriptional gene silencing in Drosophila cells", Nature, 2000, vol. 404, pp. 293-296.
Hasegawa, Y. et al., "DNA methylation of the RIZ1 gene is associated with nuclear accumulation of p53 in prostate cancer", Cancer Sci, 2007, vol. 98, No. 1, pp. 32-36.

Huang, S. et al., "The PR Domain of the Rb-binding Zinc Finger Protein RIZ1 is a Protein Binding Interface and is Related to the SET Domain Functioning in Chromatin-mediated Gene Expression", The Journal of Biological Chemistry, 1998, vol. 273, No. 26, pp. 15933-15939.
Hutvagner, G. et al., "A cellular function for the RNA-interference enzyme Dicer in the maturation of the let-7 small temporal RNA", Science, 2001, vol. 293, p. 834.
International Preliminary Report on Patentability dated Jan. 20, 2022 for International Application No. PCT/US2020/041473.
International Preliminary Report on Patentability dated Nov. 24, 2022 for International Application No. PCT/US2021/032311.
International Search Report and Written Opinion dated Jan. 7, 2021 for International Application No. PCT/US2020/041473.
International Search Report and Written Opinion dated Nov. 26, 2021 for International Application No. PCT/US2021/032311.
Jiang, G.L. et al., "Adenovirus expression RIZ1 in tumor suppressor gene therapy of microsatellite—unstable colorectal cancers", Cancer Res 2001, vol. 61, No. 5, pp. 1796-1798.
Jin, H., et al., "NNK-induced DNA methyltransferase 1 in lung tumorigenesis in A/J mice and inhibitory effects of (−)-epigallocatechin-3-gallate", Nutr Cancer, 2015, vol. 67, No. 1, pp. 167-176.
Kaniskan, H.U. et al., "Inhibitors of Protein Methyltransferases and Demethylases", Chem. Rev., 2018, vol. 118, pp. 989-1068.
Liang, X.H. "mRNA levels can be reduced by antisense oligonucleotides via no-go decay pathway", Nucleic Acids Research, 2019, vol. 47, No. 13, pp. 6900-6916.
Lin, R. et al., "Policing rogue genes", Nature, 1999, vol. 402, pp. 128-129.
Ling, Y. et al., "Dual docetaxel/superparamagnetic iron oxide loaded nanoparticles for both targeting magnetic resonance imaging and cancer therapy", Biomaterials, 2011, vol. 32, pp. 7139-7150.
Liu, L. et al, "The Retinoblastoma Interacting Zinc Finger Gene RIZ Produces a PR Domain-lacking Product through an Internal Promote", J. Biol Chem, 1997, vol. 272, No. 5, pp. 2984-2991.
Niles, B., Keystone Nano, Inc., "New RNA Therapies", Jan. 25-Jan. 27, 2022, pp. 1-27.
Precision Medicine World Conference, Jan. 25-Jan. 27, 2022, Speaker profile for Brad Niles, retrieved from the internet https://www.pmwcintl.com/session/emerging-therapeutics-showcase_2022sv, retrieved online Jul. 13, 2022, p. 1.
Oshimo, Y. et al., "Frequent Epigenetic Inactivation of RIZ1 by Promoter Hypermethlyation in Human Gastric Carcinoma", Int J Cancer, 2004, vol. 110, No. 5, pp. 212-218.
Pandzic, T. et al., Somatic PRDM2 c.4467delA mutations in colorectal cancers control histone methylation and tumor growth, Oncotarget, 2017, vol. 8, No. 58, pp. 98646-98659.
Pastural, E. et al., "RIZ1 repression is associated with insulin-like growth fator-1 signaling activation in chronic myeloid leukemia cell lines", 2006, Oncogene, vol. 26, pp. 1586-1594.
Poetsch, M. et al., "Frameshift mutations of RIZ, but no point mutations in RIZ1 exons in malignant melanomas with deletions in 1p36", Oncogene, 2002, vol. 21, No. 19, pp. 3038-3042.
Rienzo, M. et al., "Searching for a Putative Mechanism of RIZ2 Tumor-Promoting Function in Cancer Models", Front. Oncol., 2021, vol. 10, Article 583533., pp. 1-15.
Sakurada, K. et al., "RIZ, the retinoblastoma protein interacting zinc finger gene, is mutated in genetically unstable cancers of the pancreas, stomach, and colorectum", Genes, Chromosomes & Cancer, 2001, vol. 30, No. 2, pp. 207-211.
Shahid, I. et al., "In vitro inhibitory analysis of consensus siRNAs against NS3 gene of hepatitis C virus 1a genotype", Asian Pacific Journal of Tropical Medicine, 2017, vol. 10, No. 7, pp. 701-709.
Sharma, R. et al., "Bioconjugation of Calcium Phosphate Nanoparticles for Selective Targeting of Human Breast and Pancreatic Cancers In Vivo", ACS Nano, 2010, vol. 4, No. 3, pp. 1279-1287.
Shimura, H. et al., "Aberrant methylation and decreased expression of the RIZ1 gene are frequent in adult acute lymphoblastic leukemia of T-cell Phenotype", Leuk Lymphoma, 2012, vol. 53, No. 8, pp. 1599-1609.
Sorrentino, A. et al., "Human PRDM2: Structure, function and pathophysiology", Biochimica et Biophysica Acta (BBA)—Gene Regulatory Mechanisms, 2018, vol. 1861, pp. 657-671.

(56) References Cited

OTHER PUBLICATIONS

Sorrentino, A. et al., "PR/SET Domain Family and Cancer: Novel Insights from the Cancer Genome Atlas", Int J Mol Sci., 2018, vol. 19(10):3250, pp. 1-17.
Strauss, E., "Molecular Biology. Candidate 'gene silencers' found", Science, 1999, vol. 286, No. 5441, p. 886.
Tabata, T. et al., "RNA interference targeting against S100A4, suppresses cell growth and motility and induces apoptosis in human pancreatic cancer cells", Biochem Biophys Res Commun, 2009, vol. 390, No. 3, pp. 475-480.
Tan, S.X. et al., "Methylation of PRDM2, PRDM5 and PRDM16 geners in lung cancer cells", Int J Clin Exp Pathol, 2014, vol. 7, No. 5, pp. 2305-2311.
Tan, S.X. et al., "The methylation profiles of PRDM promoters in non-small cell lung cancer", Onco Targets Ther, 2018, vol. 11, pp. 2991-3002.
Thiel, K. et al., "Therapeutic Applications of DNA and RNA Aptamers", Oligonucleotides, 2009, vol. 19, No. 3, pp. 209-222.
Tuerk, C. et al., "RNA pseudoknots that inhibit human immunodeficiency virus type 1 reverse transcriptase", 1990, PNAS, vol. 89, pp. 6988-6992.
Xiao, B. et al., "SET domains and histone methylation", Curr Opin Struct Biol, 2003, vol. 13, pp. 699-705.
Xie, M. et al., "Transcriptional Repression Mediated by the PR Domain Zinc Finger Gene RIZ", J. Biol Chem, 1997, vol. 272, No. 42, pp. 26360-26366.
Yang, L. et al., "Efficient Delivery of Antisense Oligonucleotides Using Bioreducible Lipid Nanonparticles In Vitro and In Vivo", Molecular Therapy Nucleic Acids, 2020, pp. 1357-1367.
Zamore, P.D. et al., "RNAi: Double-Stranded RNA Directs the ATP-Dependent Cleavage of Mrna at 21 to 23 Nucleotide intervals", Cell, 2000, vol. 101, pp. 25-33.
Zhang. C. et al., "Methylation Status of the RIZ1 Gene Promoter in Human Glioma Tissues and Cell Lines", Cell Mol Neurobiol, 2017 ,vol. 37, No. 6, pp. 1021-1027.
Zhang, C. et al., "RIZ1: a potential tumor suppressor in glioma", BMC Cancer, 2015, vol. 15, No. 990, pp. 1-12.
Zhao, F. et al., "Effects of triptolide on RIZ1 expression, proliferation, and apoptosis in multiple myeloma U266 cells", Acta Pharmalogica Sinica, 2010, vol. 31, pp. 733-740.
Zhu, G. et al., "Aptamer-based targeted therapy", Adv Drug Deliv Rev., 2018, vol. 134, pp. 65-78.

\* cited by examiner

CANCER TREATMENT USING siRNA TO MODULATE EXPRESSION OF PRDM2/RIZ PROTEIN

CROSS-REFERENCE

This Application is a continuation application of the PCT application, PCT/US2021/032311 filed on May 13, 2021, which published as WO2021/231771 on Nov. 18, 2021 which claims the benefit of U.S. Provisional Application No. 63/024,624, filed on May 14, 2020, which is incorporated herein by reference in its entirety.

SEQUENCE LISTING

The instant application contains a Sequence Listing which has been submitted electronically in XML format and is hereby incorporated by reference in its entirety. Said XML copy, created on Dec. 7, 2022, is named 60673-701_301_SL.xml and is 62,059 bytes in size.

BACKGROUND

Cancer disease continues to be a major health concern worldwide being the second leading cause of death in the world. According to the World Health Organization (WHO), nearly 10 million people are estimated to die of cancer worldwide in the year 2020, with 2.26 million new cases of breast cancer, followed by 2.21 million of lung cancer cases. Small interfering RNAs (siRNAs) represent a new and emerging therapeutic that has shown promising results in a number of diseases. Lymphomas are cancers that arise from lymphocytes. T cell lymphoma (TCL) is a lymphoma that arises from T cells; these account for approximately 7% of all non-Hodgkin's lymphomas in the United States. Common subtypes of TCL include: Peripheral T Cell Lymphoma, Not Otherwise Specified (PTCLNOS), Anaplastic Large Cell Lymphoma (ALCL), Angioimmunoblastic T Cell Lymphoma (AITL), and Cutaneous T Cell Lymphoma (CTCL). Each type of TCL has its own pathology and symptoms. Small interfering RNAs (siRNAs) represent a new and emerging therapeutic that has shown promising results in a number of diseases. Given the complexity and severity of cancers, there is an ongoing need for improved and precisely targeted therapeutics development.

SUMMARY

Disclosed herein is a method of inhibiting cell proliferation, comprising contacting a population of cells with a composition comprising a Retinoblastoma Protein-Interacting Zinc Finger Protein 2 (RIZ2) inhibitor. In one embodiment, the RIZ2 inhibitor reduces expression of RIZ2 in the cells. In one embodiment, the RIZ2 inhibitor reduces expression of RIZ2 mRNA in the cells. In one embodiment, the RIZ2 inhibitor reduces expression of RIZ2 protein in the cells.

In some embodiments, the RIZ2 mRNA is reduced by at least 10% when compared to expression of a housekeeping gene in the cells. In some embodiments, the RIZ2 mRNA is reduced by at least 10% relative to a control cell population. In some embodiments, the control cell population is a cell population that has not been contacted with the composition comprising the RIZ2 inhibitor.

In some embodiments, expression of RIZ2 mRNA is reduced by at least 50% relative to the control cell population.

In some embodiments, expression of RIZ2 mRNA is reduced by at least 80% relative to the control cell population.

In one embodiment, the RIZ2 inhibitor further increases expression of RIZ1 in the cell population. In some embodiments, the composition alters a ratio of RIZ1 mRNA expression level to RIZ2 mRNA expression level. In some embodiments, the composition alters the ratio of RIZ1 protein expression level to RIZ2 protein expression level. In some embodiments, the RIZ2 inhibitor alters the ratio of RIZ1 to RIZ2 mRNA expression levels by greater than at least 1.1-fold.

In some embodiments, the RIZ2 inhibitor alters the ratio of RIZ1 to RIZ2 mRNA expression levels by greater than at least 1.5-fold. In some embodiments, the RIZ2 inhibitor alters the ratio of RIZ1 to RIZ2 mRNA expression levels by at least 2-fold.

In one embodiment, the RIZ2 inhibitor further decreases hypermethylation of RIZ1.

In some embodiments of the method described herein, the cells are mammalian cells. In some embodiments, the cells are human cells. In some embodiments, the cells are cancer cells.

In some embodiments of the method described herein, the cells are from a tissue that is a breast, colon, endometrial, esophageal, gastric, glioma, kidney, liver, lung, lymphoma, melanoma, meningioma, myeloma, nasopharyngeal, neuroblastoma, ovarian, pancreatic, parathyroid, pituitary, prostate, thyroid, or a uterine tissue. In some embodiments, the cancer cells are from a blood cancer.

In some embodiments, the cancer cells are from a solid tumor.

In some embodiments, the contacting comprises contacting a population of cells with the composition comprising the RIZ2 inhibitor. In some embodiments, the contacting results in a reduction of a cell number of the population of cells by at least 10%. In some embodiments, the contacting results in a reduction of a cell number of the population of cells by about 90%.

In some embodiments, inhibiting cell proliferation comprises reducing a cell mass by at least 10%. In some embodiments, inhibiting cell proliferation comprises reducing a cell mass by about 50%.

In one embodiment of the method disclosed herein, contacting the cell further comprises incorporating the RIZ2 inhibitor into the cell.

In one embodiment, the RIZ2 inhibitor comprises a non-naturally occurring compound. In one embodiment, the RIZ2 inhibitor is a synthetic agent. In one embodiment, the RIZ2 inhibitor comprises a peptide. In one embodiment, the RIZ2 inhibitor comprises a conjugated polypeptide.

In one embodiment, the RIZ2 inhibitor comprises one or more polynucleotides.

In some embodiments, RIZ2 inhibitor comprises a synthetic polynucleotide. In some embodiments, the one or more polynucleotides comprise one or more modified nucleotides. In some embodiments, the composition comprising the RIZ2 inhibitor comprises one or more polynucleotides coupled to a delivery system.

In one embodiment, the delivery system comprises one or more of lipids, cyclodextrin, chitosan, carbohydrate polymers, elastin-like polymers (ELP), calcium phosphate polymers or combinations thereof.

In some embodiments, the delivery system comprises a lipid. In some embodiments, the delivery system comprises a PEGylated lipid. In some embodiments, the delivery system comprises a cell targeting moiety. In some embodiments, the cell targeting moiety, is cell-type specific. In some embodiments, the cell targeting moiety is a ligand that selectively binds to a receptor on a target cell. In some embodiments, the cell targeting moiety is an antibody that binds to a cell surface molecule on a target cell. In some embodiments, the cell targeting moiety is a single chain antibody or an antibody fragment. In some embodiments, the cell targeting moiety is a peptide. In some embodiments, the cell targeting moiety is a cell-penetrating peptide. In some embodiments, the cell targeting moiety is cyclic peptide. In some embodiments, the cell targeting moiety is an aptamer. In some embodiments, the delivery system comprises a liposome. In some embodiments, the delivery system comprises a nanoparticle. In some embodiments, the RIZ2 inhibitor comprises an RNA molecule. In some embodiments, the RIZ2 inhibitor comprises an inhibitory RNA molecule.

In one embodiment, wherein the inhibitory RNA molecule disclosed herein hybridizes to at least 10 contiguous nucleobases on the PRDM2 gene or a PRDM2 gene product. In some embodiments, the inhibitory RNA is about 10 to about 21 nucleotides in length. In some embodiments, the inhibitory RNA molecule is double-stranded. In some embodiments, the RNA molecule comprises one or more modified nucleotides.

In some embodiments of the method disclosed herein, the RIZ2 inhibitor comprises an inhibitory double-stranded RNA comprising a sequence of SEQ ID NO: 1, or a sequence having at least 90% identity to SEQ ID NO: 1. In some embodiments of the method disclosed herein, the RIZ2 inhibitor comprises an inhibitory double-stranded RNA comprising a sequence of SEQ ID NO: 1, and a sequence of SEQ ID NO: 10.

In some embodiments of the method disclosed herein, the RIZ2 inhibitor comprises an inhibitory double-stranded RNA comprising a sequence of SEQ ID NO: 6, or a sequence having at least 90% identity to SEQ ID NO: 6. In some embodiments of the method disclosed herein, the RIZ2 inhibitor comprises an inhibitory double-stranded RNA comprising a sequence of SEQ ID NO: 6, and a sequence of SEQ ID NO: 11.

Disclosed herein is a method of treating a cell proliferative disease or a disorder in a subject, comprising administering to the subject a composition comprising a RIZ2 inhibitor.

Disclosed herein is a method of selecting a patient as a subject in need for administering a composition comprising a RIZ2 inhibitor, the method comprising: (i) detecting an elevated RIZ1 methylation level in a biological sample of the subject compared to a control sample or control value; or, (ii) detecting a downregulation of RIZ1 mRNA levels compared to a control sample or control value; wherein an at least 1.1-fold elevation of methylated RIZ1, or, at least 2-fold downregulation of RIZ1 mRNA levels in the biological sample of the subject compared to the control sample or value determines the subject to be in need for administering the composition comprising a RIZ2 inhibitor, and wherein the control sample is a sample from a clinically healthy individual, a control value is an average value of RIZ1 methylation levels from two or more clinically healthy individual samples.

In some embodiments of a method disclosed herein, the cell proliferative disease or disorder is a cancer.

In some embodiments, the cancer is a cancer of breast, colon, endometrial, esophageal, gastric, glioma, kidney, liver, lung, lymphoma, melanoma, meningioma, myeloma, nasopharyngeal, neuroblastoma, ovarian, pancreatic, parathyroid, pituitary, prostate, thyroid, or uterine tissue.

In some embodiments, the cancer is a solid tumor. In some embodiments, the cancer is a lung cancer.

In some embodiments of the method disclosed herein, administering comprises administering an effective amount of the RIZ2 inhibitor.

In some embodiments, the effective amount of the RIZ2 inhibitor is an amount that reduces at least one or more disease parameters associated with the cell proliferative disorder.

In some embodiments, the cell proliferative disease is a cancer and the effective amount of the RIZ2 reduces the number of cancer cells. In some embodiments, the cell proliferative disease is a solid tumor and the effective amount of the RIZ2 reduces the tumor mass.

In some embodiments, the composition comprising the RIZ2 inhibitor comprises one or more polynucleotides coupled to a delivery system. In some embodiments, the one or more polynucleotides comprise an inhibitory RNA molecule. In some embodiments, the inhibitory RNA molecule is a double-stranded RNA molecule comprising at least 90% sequence identity to a sequence of SEQ ID NO: 1. In some embodiments, the inhibitory RNA molecule is a double-stranded RNA molecule comprising at least 90% sequence identity to a sequence of SEQ ID NO: 6.

In some embodiments, the inhibitory RNA molecule is a double-stranded RNA molecule comprising at least 90% sequence identity to any one of the sequences listed in Table 2.

In some embodiments, the composition further comprises a delivery system. In some embodiments, the delivery system comprises a lipid and/or a cell targeting moiety. In some embodiments, the lipid is a PEGylated lipid. In some embodiments, the cell targeting moiety is a cell-penetrating peptide, a cyclic peptide, an antibody or a fragment thereof, or an aptamer.

Further disclosed herein is a pharmaceutical composition comprising: (a) the RIZ2 inhibitor; and (b) a pharmaceutically acceptable excipient. In some embodiments of the pharmaceutical composition disclosed herein, the RIZ2 inhibitor comprises one or more polynucleotide molecules and a delivery system. In some embodiments, the RIZ2 inhibitor comprises an inhibitory RNA molecule. In some embodiments, the inhibitory RNA molecule hybridizes to at least 10 contiguous nucleobases on the PRDM2 gene or a PRDM2 gene product.

In some embodiments, the inhibitory RNA molecule is about 10 to about 21 nucleotides in length. In some embodiments, the inhibitory RNA molecule is double-stranded. In some embodiments, the inhibitory double-stranded RNA comprising a sequence of SEQ ID NO: 1, or a sequence having at least 90% identity to SEQ ID NO: 1. In some embodiments, the inhibitory double-stranded RNA comprising a sequence of SEQ ID NO: 13, or a sequence having at least 90% identity to SEQ ID NO: 13. In some embodiments, the inhibitory double-stranded RNA comprising a sequence of SEQ ID NO: 13, or a sequence having at least 90% identity to SEQ ID NO: 14. In some embodiments, the delivery system comprises a cell targeting moiety. In some embodiments, the cell targeting moiety is a ligand, and antibody or an antibody fragment, a single chain antibody, a peptide or an aptamer. In some embodiments, cell-penetrating peptide.

In some embodiments, the delivery system comprises one or more of lipids, cyclodextrin, chitosan, carbohydrate polymers, elastin-like polymers (ELP), calcium phosphate polymers or combinations thereof. In some embodiments, the RIZ2 inhibitor comprises: (i) an siRNA comprising a double stranded RNA of 10-21 nucleotides that have homology to human PRDM2/RIZ2 gene; covalently linked to a (ii) a PEG molecule, linked to a (iii) cell targeting moiety; wherein the cell targeting moiety is an aptamer. In some embodiments, the delivery system comprises a liposome. In some embodiments, the delivery system comprises a nanoparticle. In some embodiments, the nanoparticle comprise lipids, cyclodextrin, chitosan, carbohydrate polymers, elastin-like polymers (ELP), calcium phosphate polymers, and combinations thereof. In some embodiments, the nanoparticle comprising a calcium phosphosilicate complex. In some embodiments, the pharmaceutical composition further comprises a calcium phosphosilicate complex associated with the RIZ2 inhibitor. In some embodiments, the pharmaceutical composition further comprises one or more chemotherapeutic drugs.

Additional features of any of the aforesaid multifunctional molecules, nucleic acids, vectors, host cells, or methods include one or more of the following enumerated embodiments.

Those skilled in the art will recognize, or be able to ascertain using no more than routine experimentation, many equivalents to the specific embodiments of the invention described herein. Such equivalents are intended to be encompassed by the following enumerated embodiments.

Additional features of any of the aforesaid multifunctional molecules, nucleic acids, vectors, host cells, or methods include one or more of the following enumerated embodiments.

Figure 1:
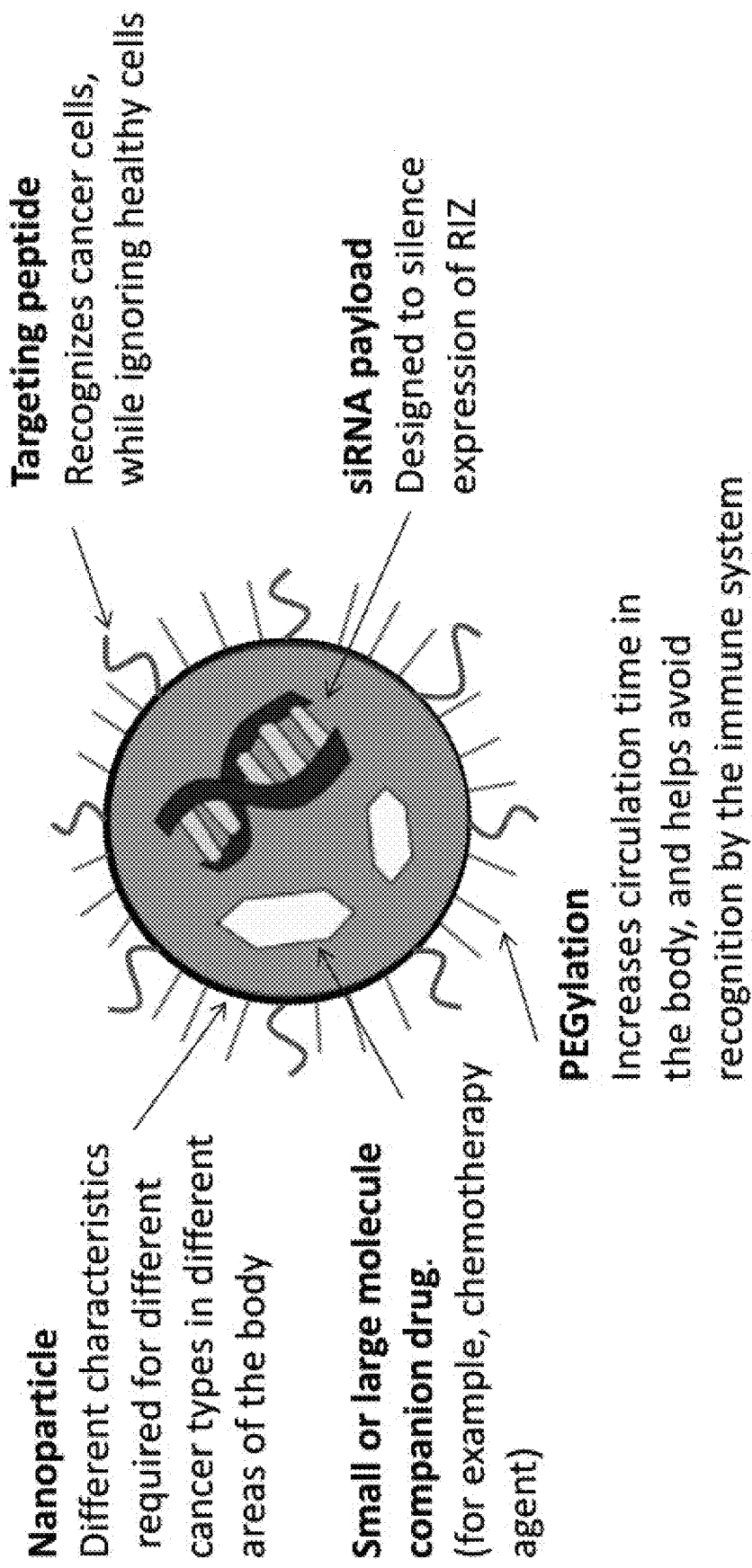
FIG. 1 depicts an example according to one embodiment of the invention comprising a drug delivery system containing an siRNA payload with complementarity to RIZ mRNA. In this example, the drug delivery system is PEGylated and bears a targeting peptide to specifically target the payload to cancer cells or cancer stem cells. To illustrate that the drug delivery system may contain one or more additional payloads, the nanoparticle is shown containing a small or large molecule companion drug, in addition to the anti-RIZ siRNA. Such additional payload(s) may be currently approved chemotherapy agents, repurposed drugs, or any drug that effectively aids in killing, or controlling the growth or spread of cancer cells.

The accompanying drawings numbered herein are given by way of illustration only and are not intended to be limitative to any extent.

DETAILED DESCRIPTION

The present disclosure is based on an important finding that a balance between RIZ1 and RIZ2 levels in mammalian cells is a determinant of an unperturbed normal life cycle of the cell, and an imbalance of the same leads to cell cycle changes leading to a hyper-proliferative disorder, e.g., a hyperplasia or cancer. The present disclosure is based on the further breakthrough development that RIZ2 can be specifically targeted to address the imbalance, and thereby to prevent or ameliorate a hyper-proliferative disorder, such as a cancer.

Current anti-cancer drug therapies are of limited effectiveness. Commonly used anti-cancer drugs may bring about temporary remission of tumors, and help prolong the patient's life, but in most cases are not curative because they often do not eliminate the cancer completely and tumors may subsequently reemerge. Small molecule chemotherapies are currently the most widely used treatment for cancer, but their action is largely non-specific.

Chemotherapy agents have serious off-target toxic effects, causing collateral damage to normal, healthy cells and tissues as well as the cancerous cells that they are intended to control and destroy. Consequently, patients suffer from severe side effects due to toxicity. Immune based therapies were expected to decrease toxicity and improve survival, but despite their promise they have only incrementally improved the prospects for cancer treatment and for favorable long-term patient outcomes. Although targeted therapy and immunotherapy are increasingly used as supplements or alternatives to traditional chemotherapy, such therapies generally lack long-term effectiveness, as cancers commonly adapt and rapidly develop resistance, escaping the targeted therapy effect. For the foregoing reasons, chemotherapy, immunotherapy, and targeted therapies are rarely curative. By addressing the root cause, cancer may be cured, for example overcoming the underlying genetic abnormalities that make cells cancerous and give rise to this devastating disease in the first place. The approach may involve modulating the expression of proteins that act as master regulators to suppress tumorigenesis in normal cells, but become drivers of cancer cell formation when expressed abnormally.

Of particular interest are cancer treatments that focus on altering the expression of the PRDM class of tumor suppressor genes. The PRDMs are a family of genes and proteins that control cell growth, proliferation, survival and mobility. Studies show that changes in the expression and activity of the PRDMs are commonly among the first changes in normal cells that lead to cancer cell formation. Aberrant expression of PRDM genes is strongly implicated in a wide variety of cancer types. The PRDMs have been implicated as causative genes and proteins in solid tumors such as breast, colon, gastric, liver, lung, melanoma, prostate and other cancers, as well as in blood cancers such as leukemia, lymphoma and myeloma.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise. The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising". It is understood that terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention. Nothing herein is intended as a promise.

By "agent" is meant any small molecule chemical compound, antibody, nucleic acid molecule, or polypeptide, or fragments thereof.

The terms "polynucleotide" and "nucleic acid" are used interchangeably herein and refer to polymers of nucleotides of any length, and include DNA and RNA, for example, mRNA. The nucleotides can be deoxyribonucleotides, ribonucleotides, modified nucleotides or bases, and/or their analogs, or any substrate that can be incorporated into a polymer by DNA or RNA polymerase. In some embodiments, the polynucleotide and nucleic acid can be in vitro transcribed mRNA. In some embodiments, the polynucleotide that is administered using the methods of the invention is mRNA.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software that can be used to obtain alignments of amino acid or nucleotide sequences are well-known in the art. These include, but are not limited to, BLAST, ALIGN, Megalign, BestFit, GCG Wisconsin Package, and variations thereof. In some embodiments, two nucleic acids or polypeptides described herein are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection.

Cell proliferative disorder or hyperproliferative disorder, as used herein is a disease or a disorder associated with an increased, in most cases uncontrolled cell proliferation due to disfunction of one or more cell cycle related genes. Exemplary hyperproliferative disorder is neoplasia, cancer. Cell cycle is the cyclic interval between two consecutive G0/G1 phases (or two consecutive G1/M phases) in the life cycle of a cell, which usually remains constant for a cell type under optimal environmental conditions. A cell cycle disorder may be a disorder that disrupts the normal cyclic interval between two consecutive G0/G1 phases (or two consecutive G1/M phases) in the life cycle of the cell, in general that may be caused by disruption of a cell cycle regulator. For example, an exemplary cell cycle regulator is cyclin D. In some embodiments, RIZ1 and/or RIZ2 may be considered regulators of cell cycle. In some embodiments, RIZ1 and/or RIZ2 may be considered master regulators of cell cycle, in that they control life cycle ubiquitously; or that they control a nodal point in the life cycle of a cell which is irrespective of the cell type, location or environmental conditions.

Hyperplasia may be defined as a condition of rapid cell proliferation, e.g, as a result of disruption of a cell cycle regulator, e.g., a checkpoint inhibitor. Neoplasia is a condition where a cell has undergone a neoplastic transformation, e.g., a cancerous transformation.

RNA interference and siRNA. RNA interference refers to the process of sequence-specific post-transcriptional gene silencing in animals mediated by short interfering RNAs (siRNAs) (Zamore et al, 2000, Cell, 101, 25-33; Fire et al., 1998, Nature, 391, 806; Hamilton et al., 1999, Science, 286, 950-951, Lin et al., 1999, Nature, 402, 128-129; and Strauss, 1999, Science, 286, 886). The corresponding process in plants (Heifetz et al., International PCT Publication No. WO 99/61631) is commonly referred to as post-transcriptional gene silencing or RNA silencing and is also referred to as quelling in fungi. The presence of long dsRNAs in cells stimulates the activity of a ribonuclease III enzyme referred to as dicer (Bass, 2000; Cell, 101, 235; Zamore et al., 2000, Cell, 101, 25-33; Hammond et al., 2000, Nature, 404, 293). Dicer is involved in the processing of the dsRNA into short pieces of dsRNA known as short interfering RNAs (siRNAs) (Zamore et al., 2000, Cell, 101, 25-33; Bass, 2000, Cell, 101, 235; Berstein et al., 2001, Nature, 409, 363). Short interfering RNAs derived from dicer activity are typically about 21 to about 23 nucleotides in length and comprise about 19 base pair duplexes (Zamore et al., 2000, Cell, 101, 25-33; Elbashir et al., 2001, Genes Dev., 15, 188). Dicer has also been implicated in the excision of 21- and 22-nucleotide small temporal RNAs (stRNAs) from precursor RNA of conserved structure that are implicated in translational control (Hutvagner et al., 2001, Science, 293, 834). The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex (Elbashir et al., 2001, Genes Dev., 15, 188).

The term "inhibition" is used often interchangeably with "reduction" or "reduction in expression levels" and indicates reduction in the level of a particular component that is inhibited, wherein the reduction may be partial, (e.g., 20%, 50%, 75%, 80%), or complete (about 100%). For example, a RIZ2 inhibitor inhibits RIZ2 protein in a cell by about 50%, or about 100%.

The terms "treatment," "treating," "alleviation" and the like, when used in the context of a disease, injury or disorder, are used herein to generally mean obtaining a desired pharmacologic and/or physiologic effect, and may also be used to refer to improving, alleviating, and/or decreasing the severity of one or more symptoms of a condition being treated. The effect may be prophylactic in terms of completely or partially delaying the onset or recurrence of a disease, condition, or symptoms thereof, and/or may be therapeutic in terms of a partial or complete cure for a disease or condition and/or adverse effect attributable to the disease or condition. "Treatment" as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition (e.g., arresting its development); or (c) relieving the disease or condition (e.g., causing regression of the disease or condition, providing improvement in one or more symptoms).

PRDM Genes and Biology

The instant disclosure relates to methods and compositions for modulating the expression and function of one or more PRDM genes, for example, PRDM2 genes. In general, PR/SET ([Su(var)3-9, enhancer-of-zeste and trithorax] that defines a large group of histone methyltransferases (HMTs) domain 2 (PRDM2) belongs to the positive regulatory domain (PRDM) gene family, a subfamily of Kruppel-like zinc finger gene products currently including 19 members in humans. PR domains have a protein-binding interface, and some of them can accommodate the universal methyl donor S-adenosyl methionine (SAM), therefore functioning as lysine methyltransferases (KMTs) PRDM (PRDI-BF1 and RIZ homology domain containing) protein family members belong to a superfamily of histone/protein methyltransferases (PRDMs), which are characterized by the conserved N-terminal PR domain, with methyltransferase activity and zinc linger arrays at she C-terminus. Members of this class are characterized by the presence of a PR domain and a variable number of Zn-finger repeats. Experimental evidence has shown that the PRDM proteins play an important role in gene expression regulation, modifying the chromatin structure either directly, through the intrinsic methyltransferase activity, or indirectly through the recruitment of chromatin remodeling complexes. PRDM proteins function as transcription factors, governing the expression of a vast array of other genes involved in developmental processes including growth, differentiation, proliferation, mobility, and survival. PRDM proteins are therefore master transcriptional regulators, driving and maintaining cell state transitions in response to developmental signals. Some PRDM proteins normally function as tumor suppressors, if their expression becomes dysregulated, or certain isoforms become expressed in abnormal proportions, these changes may become drivers of cancer onset and progression. Many cancer types are strongly associated with dysfunction of particular PRDM proteins. In such tumors, the normal PRDM protein may be expressed at levels that are abnormally low. RDM proteins have a dual action: they mediate the effect induced by different cell signals like steroid hormones and control the expression of growth factors. PRDM proteins therefore have a pivotal role in the transduction of signals that control cell proliferation and differentiation and consequently neoplastic transformation. (Zazzo et al., Biology (Basel). 2013 March; 2 (1): 107-141). The PR domain shares high homology with the catalytic SET (Suppressor of variegation 3-9, Enhancer of zeste and Trithorax) domain that defines a group of histone methyltransferases (Xiao B. et al., Curr. Opin. Struct. Biol. 2003; 13:699-705). In the human genome there are 17 genes encoding for proteins with a PR/SET and all of them but PRDM11 have a variable number of Zn-finger domains (Fumasoni I. et al., BMC Evol. Biol. 2007; 7:187). PRDM proteins have a pivotal role in the transduction of signals that control cell proliferation and differentiation and consequently neoplastic transformation (Fog C. K et al., BioEssays. 2011; 34:50-60). A common characteristic of PRDM family genes is the expression of different molecular forms by alternative splicing or by the action of different promoters. Furthermore, some genes of this family are expressed as two alternative forms, one lacking the PR domain (PR-minus) but otherwise identical to the other PR-containing product (PR-plus) (PRDM1, PRDM2, PRDM3, PRDM16) [(Gyory et al., J. Immunol, 2003, 170:3125-3133), (Liu L., et al., J. Biol. Chem. 1997, 272:2984-2991)]. Other genes encode for proteins that differ for the presence or absence of Zn-finger domains (PRDM6, PRDM9).

PRDM1 and PRDM2, initially identified as Blimp-1 (B lymphocyte-induced maturation protein-1) and RIZ (Retinoblastoma interacting zinc finger protein) respectively, have two promoters that encode for a PR-plus and a PR-minus isoform. PRDM1 promoters are localized upstream of exon 1 and exon 4 respectively. These transcriptional start sites at two promoters guide: PRDI-BF1 (Positive regulatory domain I-binding factor 1) α (PR-plus) e PRDI-BF1β (PR-minus) that differ only by the PR domain presence. Similarly to PRDM1, PRDM2 expresses two proteins, PRDM2a/RIZ1 (PR-plus) and PRDM2b/RIZ2 (PR-minus), by differential transcription initiated by the two promoters. One promoter of PRDM2 is located upstream of the open reading frame in a region including exon 1a and a second promoter is located within intron 5 and exon 6. PRDM2 was first identified in independent studies as retinoblastoma interacting zinc-finger protein (RIZ) and as GATA-3 binding protein through functional screenings of human cDNA libraries (Sorrentino, A. et al., 2018, Volume 1861, Issue 7, Pages 657-671). Later, a PRDM2 variant, named MTE-binding protein zinc-finger type (MTB-ZF), was isolated from a human monocytic leukemia cell line cDNA expression library.

TABLE 1

PRDM genes and proteins

| Gene/Protein | Cellular localization | Methyl transferase activity (if/where known) |
|---|---|---|
| PRDM1(BLIMP1)/PR domain zinc finger protein 1 | nucleocytoplasm | — |
| PRDM 2(RIZ)/PR domain zinc finger protein 2 (MTE binding protein) | Isoform: RIZ1: nucleus | H3K9 HMT activity |
| | Isoform: RIZ2: nucleus | — |

TABLE 1-continued

PRDM genes and proteins

| Gene/Protein | Cellular localization | Methyl transferase activity (if/where known) |
|---|---|---|
| PRDM3/MIDS1 and EVI1 complex locus protein 1 | Isoform 1: nucleus<br>Isoform 2: nucleus<br>Isoform 3: nucleus<br>Isoform 4: nucleus<br>Isoform 5: nucleus<br>Isoform 6: nucleus | H3K9me1 |
| PRDM4/PR domain zinc finger protein 4 | nucleus | — |
| PRDM5/PR domain zinc finger protein 5 | Isoform 1: nucleus<br>Isoform 2: nucleus<br>Isoform 3: nucleus | — |
| PRDM6/Putitive histone, lysine N-methyl transferase PRDM6 | Isoform 1: nucleus<br>Isoform 2: nucleus<br>Isoform 3: nucleus | H4K20 |
| PRDM7/Probable histone, lysine N-methyl transferase PRDM7 | Isoform 1: nucleus<br>Isoform 2: nucleus<br>Isoform 3: nucleus | — |
| PRDM8/PR domain zinc finger protein 8 | Isoform 1: nucleus<br>Isoform 2: nucleus | H3K9 |
| PRDM9/histone N-methyl transferase PRDM9 | nucleus | H3K4-me3 |
| PRDM10/PR domain zinc finger protein 10 | Isoform 1: nucleus<br>Isoform 2: nucleus<br>Isoform 3: nucleus<br>Isoform 4: nucleus<br>Isoform 5: nucleus<br>Isoform 6: nucleus | — |
| PRDM17/PR domain zinc finger protein 11 | nucleus | — |
| PRDM12/PR domain zinc finger protein 12 | nucleus | — |
| PRDM13/PR domain zinc finger protein 13 | nucleus | — |
| PRDM14/PR domain zinc finger protein 14 | nucleus | — |
| PRDM15/PR domain zinc finger protein 15 | nucleus | — |
| PRDM16/PR domain zinc finger protein 16 | Isoform 1: nucleus<br>Isoform 2: nucleus<br>Isoform 3: nucleus | H3K9me1 |
| PRDM17l/PR domain zinc finger protein 17 | nucleus | — |

Thus far, enzymatic activity has been experimentally demonstrated only for a few family members: PRDM9 (directed toward H3K4me3, H3K9me1/3, H3K18me1, H3K36me3 and H4K20me1/2), PRDM2, PRDM3 and PRDM16 (H3K9me1) and PRDM8 (H3K9me3) (Xie, M. et al., J. Biol. Chem., 1997, 272:42, 2636-26366). Additionally, activity has been reported for PRDM6, even though the nature of this activity requires further elucidation.

PRDM2, or retinoblastoma-binding protein (RIZ) RIZ encodes Rb-binding proteins and the PRDI-BF1/BLIMP1 transcription repressor, which promotes B-lymphocyte maturation. RIZ can have two isoforms, PRDM2a (RIZ1) and PRDM2b (RIZ2). Both the proteins are widely expressed in mammalian cells. RIZ1 is identical to RIZ2, except that it has an extra 201 residues at the amino terminus, which, in RIZ1 comprises PR domain. These extra residues in RIZ1 is known to confer specific function to RIZ1 protein. An internal promoter generates RIZ2, that lacks the RIZ1 PR domain. The PR domain represents the major functional motif within the RIZ1 amino-terminal region. PR domain is a derivative of SET domain and may function as the protein binding interface in the regulation of chromatin-mediated gene expression.

An exemplary sequence of the N-terminal region comprising the PR domain in RIZ1, that is absent in RIZ2 is shown below, and a putative PR domain is marked in bold:

(SEQ ID NO: 19)
MNQNTTEPVAATETLAEVPEHVLRGLPEEVRLFPSAVDKTR

IGVWATKPILKGKKFGPFVGDKKKRSQVKNNVYMWEVYYPN

LGWMCIDATDPEKGNWLRYVNWACSGEEQNLFPLEINRAIY

YKTLKPIAPGEELLVWYNGEDNPEIAAAIEEERASARSKRS

SPKSRKGKKKSQENKNKGNKIQDIQLKTSEPDFTSAN.

RIZ2 is characterized by the absence of the segment designated as SEQ ID NO: 19 that is present in RIZ1.

An exemplary RIZ2 protein sequence is provided below.

(SEQ ID NO: 20)
MRDSAEGPKEDEEKPSASALEQPATLQEVASQEVPP

ELATPAPAWEPQPEPDERLEAAACEVNDLGEEEEE

EEEEDEEEEEDDDDDELEDEGEEEASMPNENSVKE

PEIRCDEKPEDLLEEPKTTSEETLEDCSEVTPAMQ

IPRTKEEANGDVFETFMFPCQHCERKFTTKQGLER

HMHIHISTVNHAFKCKYCGKAFGTQINRRRHERRH

EAGLKRKPSQTLQPSEDLADGKASGENVASKDDSS

PPSLGPDCLIMNSEKASQDTINSSVVEENGEVKEL

HPCKYCKKVFGTHTNMRRHQRRVHERHLIPKGVRR

KGGLEEPQPPAEQAQATQNVYVPSTEPEEEGEADD

VYIMDISSNISENLNYYIDGKIQTNNNTSNCDVIE

MESASADLYGINCLLTPVTVEITQNIKTTQVPVTE

DLPKEPLGSTNSEAKKRRTASPPALPKIKAETDSD

PMVPSCSLSLPLSISTTEAVSFHKEKSVYLSSKLK

QLLQTQDKLTPAGISATEIAKLGPVCVSAPASMLP

VTSSRFKRRTSSPPSSPQHSPALRDFGKPSDGKAA

WTDAGLTSKKSKLESHSDSPAWSLSGRDERETVSP

PCFDEYKMSKEWTASSAFSSVCNQQPLDLSSGVKQ

KAEGTGKTPVQWESVLDLSVHKKHCSDSEGKEFKE

SHSVQPTCSAVKKRKPTTCMLQKVLLNEYNGIDLP

VENPADGTRSPSPCKSLEAQPDPDLGPGSGFPAPT

VESTPDVCPSSPALQTPSLSSGQLPPLLIPTDPSS

PPPCPPVLTVATPPPPLLPTVPLPAPSSSASPHPC

PSPLSNATAQSPLPILSPTVSPSPSPIPPVEPLMS

AASPGPPTLSSSSSSSSSSSSSFSSSSSSSSPSPPP

LSAISSVVSSGDNLEASLPMISFKQEELENEGLKP

REEPQSAAEQDVVVQETFNKNFVCNVCESPPFLSIK

DLTKHLSIHAEEWPFKCEFCVQLFKDKTDLSEHRF

LLHGVGNIFVCSVCKKEFAFLCNLQQHQRDLHPDK

VCTHHEFESGTLRPQNFTDPSKAHVEHMQSLPEDP

LETSKEEEELNDSSEELYTTIKIMASGIKTKDPDV

RLGLNQHYPSFKPPPFQYHHRNPMGIGVTATNFTT

HNIPQTFTTAIRCTKCGKGVDNMPELHKHILACAS

ASDKKRYTPKKNPVPLKQTVQPKNGVVVLDNSGKN

AFRRMGQPKRLNFSVELSKMSSNKLKLNALKKKNQ

LVQKAILQKNKSAKQKADLKNACESSSHICPYCNR

EFTYIGSLNKHAAFSCPKKPLSPPKKKVSHSSKKG

GHSSPASSDKNSNSNHRRRTADAEIKMQSMQTPLG

KTRARSSGPTQVPLPSSSFRSKQNVKFAASVKSKK

PSSSSLRNSSPIRMAKITHVEGKKPKAVAKNHSAQ

LSSKTSRSLHVRVQKSKAVLQSKSTLASKKRTDRF

NIKSRERSGGPVTRSLQLAAAADLSENKREDGSAK

QELKDFRNFL.

The sequence of SEQ ID NO: 20 aligns perfectly with RIZ1 at amino acid residue 202 for RIZ1 onwards. Shown below, the query sequence is RIZ1 (SEQ ID NO: 21), and the subject sequence is RIZ2 (SEQ ID NO: 22). For example, a PRDM2/RIZ1 is a sequence of that of NM_012231. For example, a PRDM2/RIZ2 is a sequence is that of NM_001007257. The sequence of NM_012231 is an exemplary human RIZ1 sequence. The sequence of NM_001007257 is an exemplary human RIZ2 sequence.

```
Query  202  MRDSAEGPKEDEEKPSASALEQPATLQEVASQEVPPELATPAPAWEPQPEPDERLEAAAC  261
            MRDSAEGPKEDEEKPSASALEQPATLQEVASQEVPPELATPAPAWEPQPEPDERLEAAAC
Sbjct    1  MRDSAEGPKEDEEKPSASALEQPATLQEVASQEVPPELATPAPAWEPQPEPDERLEAAAC   60

Query  262  EVNDLGEEEEEEEEDEEEEEDDDDDELEDEGEEEASNPNENSVKEPEIRCDEKPEDLLE   321
            EVNDLGEEEEEEEEDEEEEEDDDDDELEDEGEEEASNPNENSVKEPEIRCDEKPEDLLE
Sbjct   61  EVNDLGEEEEEEEEDEEEEEDDDDDELEDEGEEEASNPNENSVKEPEIRCDEKPEDLLE  120

Query  322  EPKTTSEETLEDCSEVTPAMQIPRTKEEANGDVFETFMFPCQHCERKFTTKQGLERHMHI  381
            EPKTTSEETLEDCSEVTPAMQIPRTKEEANGDVFETFMFPCQHCERKFTTKQGLERHMHI
Sbjct  121  EPKTTSEETLEDCSEVTPAMQIPRTKEEANGDVFETFMFPCQHCERKFTTKQGLERHMHI  180

Query  382  HISTVNHAFKCKYCGKAFGTQINRRRHERRHEAGLKRKPSQTLQPSEDLADGKASGENVA  441
            HISTVNHAFKCKYCGKAFGTQINRRRHERRHEAGLKRKPSQTLQPSEDLADGKASGENVA
Sbjct  181  HISTVNHAFKCKYCGKAFGTQINRRRHERRHEAGLKRKPSQTLQPSEDLADGKASGENVA  240

Query  442  SKDDSSPPSLGPDCLIMNSEKASQDTINSSVVEENGEVKELHPCKYCKKVFGTHTNMRRH  501
            SKDDSSPPSLGPDCLIMNSEKASQDTINSSVVEENGEVKELHPCKYCKKVFGTHTNMRRH
Sbjct  241  SKDDSSPPSLGPDCLIMNSEKASQDTINSSVVEENGEVKELHPCKYCKKVFGTHTNMRRH  300

Query  502  QRRVHERHLIPKGVRRKGGLEEPQPPAEQAQATQNVYVPSTEPEEEGEADDVYIMDISSN  561
            QRRVHERHLIPKGVRRKGGLEEPQPPAEQAQATQNVYVPSTEPEEEGEADDVYIMDISSN
Sbjct  301  QRRVHERHLIPKGVRRKGGLEEPQPPAEQAQATQNVYVPSTEPEEEGEADDVYIMDISSN  360

Query  562  ISENLNYYIDGKIQTNNNTSNCDVIEMESASADLYGINCLLTPVTVEITQNIKTTQVPVT  621
            ISENLNYYIDGKIQTNNNTSNCDVIEMESASADLYGINCLLTPVTVEITQNIKTTQVPVT
Sbjct  361  ISENLNYYIDGKIQTNNNTSNCDVIEMESASADLYGINCLLTPVTVEITQNIKTTQVPVT  420

Query  622  EDLPKEPLGSTNSEAKKRRTASPPALPKIKAETDSDPMVPSCSLSLPLSISTTEAVSFHK  681
            EDLPKEPLGSTNSEAKKRRTASPPALPKIKAETDSDPMVPSCSLSLPLSISTTEAVSFHK
Sbjct  421  EDLPKEPLGSTNSEAKKRRTASPPALPKIKAETDSDPMVPSCSLSLPLSISTTEAVSFHK  480

Query  682  EKSVYLSSKLKQLLQTQDKLIPAGISATEIAKLGPVCYSAPASHLPVTSSRFKRRTSSPP  742
            EKSVYLSSKLKQLLQTQDKLIPAGISATEIAKLGPVCYSAPASHLPVTSSRFKRRTSSPP
Sbjct  481  EKSVYLSSKLKQLLQTQDKLIPAGISATEIAKLGPVCYSAPASHLPVTSSRFKRRTSSPP  540
```

```
Query  742 SSPQHSPALRDFGKPSDGKAAWTDAGLTSKKSKLESHSDSPAWSLSGRDERETVSPPCFD   881
           SSPQHSPALRDFGKPSDGKAAWTDAGLTSKKSKLESHSDSPAWSLSGRDERETVSPPCFD
Sbjct  541 SSPQHSPALRDFGKPSDGKAAWTDAGLTSKKSKLESHSDSPAWSLSGRDERETVSPPCFD   600

Query  802 EYKMSKEWTASSAFSSVCNQQPLDLSSGVKQKAEGTGKTPVQNESVLDLSVHKKHCSDSE   861
           EYKMSKEWTASSAFSSVCNQQPLDLSSGVKQKAEGTGKTPVQNESVLDLSVHKKHCSDSE
Sbjct  601 EYKMSKEWTASSAFSSVCNQQPLDLSSGVKQKAEGTGKTPVQNESVLDLSVHKKHCSDSE   660

Query  862 GKEFKESHSVQPTCSAVKKRKPTTCMLQKVLLNEYNGIDLPVENPADGTRSPSPCKSLEA   922
           GKEFKESHSVQPTCSAVKKRKPTTCMLQKVLLNEYNGIDLPVENPADGTRSPSPCKSLEA
Sbjct  661 GKEFKESHSVQPTCSAVKKRKPTTCMLQKVLLNEYNGIDLPVENPADGTRSPSPCKSLEA   720

Query  922 QPDPDLGPGSGFPAPTVESTPDVCPSSPALQTPSLSSGQLPPLLIPTDPSSPPPCPPVLT   982
           QPDPDLGPGSGFPAPTVESTPDVCPSSPALQTPSLSSGQLPPLLIPTDPSSPPPCPPVLT
Sbjct  721 QPDPDLGPGSGFPAPTVESTPDVCPSSPALQTPSLSSGQLPPLLIPTDPSSPPPCPPVLT   788

Query  982 VATPPPPLLPTVPLPAPSSSASPHPCPSPLSNATAQSPLPILSPTVSPSPSPIPPVEPLN  1841
           VATPPPPLLPTVPLPAPSSSASPHPCPSPLSNATAQSPLPILSPTVSPSPSPIPPVEPLN
Sbjct  781 VATPPPPLLPTVPLPAPSSSASPHPCPSPLSNATAQSPLPILSPTVSPSPSPIPPVEPLN   848

Query 1042 SAASPGPPTLSSSSSSSSSSSSFSSSSSSSSPSPPPLSAISSVVSSGDNLEASLPIISFK  1101
           SAASPGPPTLSSSSSSSSSSSSFSSSSSSSSPSPPPLSAISSVVSSGDNLEASLPIISFK
Sbjct  841 SAASPGPPTLSSSSSSSSSSSSFSSSSSSSSPSPPPLSAISSVVSSGDNLEASLPIISFK   990

Query 1102 QEELENEGLKPREEPQSAAEQDVVVQETFNKNFVCNVCESPPFLSIKDLTKHLSIHAEEWP  1161
           QEELENEGLKPREEPQSAAEQDVVVQETFNKNFVCNVCESPPFLSIKDLTKHLSIHAEEWP
Sbjct  901 QEELENEGLKPREEPQSAAEQDVVVQETFNKNFVCNVCESPPFLSIKDLTKHLSIHAEEWP   980

Query 1162 FKCEFCVQLFKDKTDLSEHRFLLHGVGNIFVCSVCKKEFAFLCNLQQHQRDLHPDKVCTH  1221
           FKCEFCVQLFKDKTDLSEHRFLLHGVGNIFVCSVCKKEFAFLCNLQQHQRDLHPDKVCTH
Sbjct  961 FKCEFCVQLFKDKTDLSEHRFLLHGVGNIFVCSVCKKEFAFLCNLQQHQRDLHPDKVCTH  1020

Query 1222 HEFESGTLRPQNFTDPSKAHVEHMQSLPEDPLETSKEEEELNDSSEELYTTIKIMASGIK  1281
           HEFESGTLRPQNFTDPSKAHVEHMQSLPEDPLETSKEEEELNDSSEELYTTIKIMASGIK
Sbjct 1021 HEFESGTLRPQNFTDPSKAHVEHMQSLPEDPLETSKEEEELNDSSEELYTTIKIMASGIK  1080

Query 1282 TKDPDVRLGLNQHYPSFKPPPFQYHHRNPMGIGVTATNFTTHNIPQTFTTAIRCTKCGKG  1341
           TKDPDVRLGLNQHYPSFKPPPFQYHHRNPMGIGVTATNFTTHNIPQTFTTAIRCTKCGKG
Sbjct 1081 TKDPDVRLGLNQHYPSFKPPPFQYHHRNPMGIGVTATNFTTHNIPQTFTTAIRCTKCGKG  1140

Query 1342 VDNMPELHKHILACASASDKKRYTPKKNPVPLKQTVQPKNGVVVLDNSGKNAFRRMGQPK  1401
           VDNMPELHKHILACASASDKKRYTPKKNPVPLKQTVQPKNGVVVLDNSGKNAFRRMGQPK
Sbjct 1141 VDNMPELHKHILACASASDKKRYTPKKNPVPLKQTVQPKNGVVVLDNSGKNAFRRMGQPK  1288

Query 1402 RLNFSVELSKMSSMKLKLNALKKKNQLVQKAILQKNKSAKQKADLKNACESSSHICPYCN  1451
           RLNFSVELSKMSSMKLKLNALKKKNQLVQKAILQKNKSAKQKADLKNACESSSHICPYCN
Sbjct 1201 RLNFSVELSKMSSMKLKLNALKKKNQLVQKAILQKNKSAKQKADLKNACESSSHICPYCN  1250

Query 1462 REFTYIGSLNKHAAFSCPKKPLSPPKKKVSHSSKKGGHSSPASSDKNSNSNHRRRTADAE  1521
           REFTY GSLNKHAAFSCPKKPLSPPKKKVSHSSKKGGHSSPASSDKNSNSNHRRRTADAE
Sbjct 1261 REFTYTGSLNKHAAFSCPKKPLSPPKKKVSHSSKKGGHSSPASSDKNSNSNHRRRTADAE  1320

Query 1522 IKMQSMQTPLGKTRARSSGPTQVPLPSSSFRSKQNVKFAASVKSKKPSSSSLRNSSPIRM  1581
           IKMQSMQTPLGKTRARSSGPTQVPLPSSSFRSKQNVKFAASVKSKKPSSSSLRNSSPIRM
Sbjct 1321 IKMQSMQTPLGKTRARSSGPTQVPLPSSSFRSKQNVKFAASVKSKKPSSSSLRNSSPIRM  1380

Query 1582 AKITHVEGKKPKAVAKNHSAQLSSKTSRSLHVRVQKSKAVLQSKSTLASKKRTDRFNIKS  1641
           AKITHVEGKKPKAVAKNHSAQLSSKTSRSLHVRVQKSKAVLQSKSTLASKKRTDRFNIKS
Sbjct 1381 AKITHVEGKKPKAVAKNHSAQLSSKTSRSLHVRVQKSKAVLQSKSTLASKKRTDRFNIKS  1448

Query 1642 RERSGGPVTRSLQLAAAADLSENKREDGSAKQELKDF                         1678
           RERSGGPVTRSLQLAAAADLSENKREDGSAKQELKDF
Sbjct 1441 RERSGGPVTRSLQLAAAADLSENKREDGSAKQELKDF                         1477
```

Both RIZ1 and RIZ2 bind to GC-rich Sp-1-like DNA elements and repress transcription of the simian virus 40 early promoter, but RIZ1 is a more potent repressor than RIZ2, suggesting that the PR domain of RIZ1 modulates transcription (Huang, S., J. Biol. Chem., Vol. 273, No. 26, Issue of June 26, pp. 15933-15939).

RIZ1 proteins are expressed in normal tissues, but in many human malignant tissues and cancer cell lines, a reduction or absence of RIZ1 and/or an increase in RIZ2 expression levels have frequently been detected. As has been proposed for other PRDM proteins, this "yin-yang" imbalance in the amount of the two protein products may be important for neoplastic transformation. Moreover, an exclusive negative selection (specific genetically or epigenetically mediated downregulation) for RIZ1 versus RIZ2 seems to be a common feature for various human cancers. This observation suggests that RIZ1 may have tumor suppressor activity and that RIZ2 is necessary for oncogenesis by promoting cell proliferation through its mitogenic activity. RIZ2 putative intrinsic growth-promoting oncogenic properties have been linked to the first cluster of Zn-finger domains (residues 359-507) that are present in both RIZ1 and RIZ2. Indeed, stably transfected MCF7 cells expressing this cluster of Zn-fingers showed an increased proliferation rate compared to control cells, both in estrogen deprived conditions or upon estrogen stimulation, and showed higher expression levels of cyclin D1 and A and reduced responsiveness to the growth inhibitory effect of anti-estrogens. In addition, through a proteomic mass spectrometry-based approach, the forced expression of PRDM2 gene Zn-finger domains in MCF-7 cells was correlated to the differential expression of proteins associated with different types of carcinomas or involved in cell proliferation and differentiation, such as keratin K8, glycolytic enzyme a-enolase, acid protease cathepsin D and nucleoside diphosphate kinase A. Altered expression of these proteins may contribute to the observed higher proliferation rate. The oncogenic proprieties of RIZ2 are likely inhibited by the presence of the PR domain in RIZ1 protein. The drastic functional difference in chromatin regulation between RIZ1 and RIZ2, due to the PR domain conferring specific functions to RIZ1, may underlie their opposite roles in tumorigenesis.

The imbalance in the respective amounts of RIZ1 and RIZ2 may be an important cause of malignancy, with the PR-positive isoform commonly lost or downregulated and the PR-negative isoform always being present at higher levels in cancer cells. Interestingly, the RIZ1 isoform also represents an important target of estradiol action downstream of the interaction with hormone receptor. Furthermore, the imbalance between the two products could also be a molecular basis for other human diseases. In one embodiment according to the invention as illustrated in FIG. 1, a drug delivery vehicle is equipped with a protective layer (for example, PEGylation of liposomes) to extend the drug lifetime in the bloodstream and shield the drug delivery system from destruction by the immune system. In one embodiment, the drug delivery system is specifically targeted to cancer cells via a ligand that targets a receptor or other moiety on the surface of a tumor cell or cancer stem cell. The ligand may be a protein, peptide or other class of molecule with the ability to bind to the targeted cancer cell with high specificity and affinity. This targeted drug delivery system should protect against damage to healthy cells, as well as concentrate the payload at the target site. Together this should increase efficacy (at lower drug doses) and improve the safety profile, resulting in a higher therapeutic index.

In other embodiments, the drug delivery vehicle may carry payloads in addition to the inhibitory siRNA, to potentiate the anti-cancer efficacy of the drug formulation. Such additional payloads may include, but are not limited to, large or small molecule chemotherapy agents.

Modulating PRDM2 Gene Expression

PRDM2/RIZ1 may be regulated via methylation. In one aspect, RIZ2 hypermethylation may be targeted for cancer therapy. For instance, in a study, PRDM2/RIZ1 methylation frequency has been observed to be about 73% in tumor vs. 20% in distant lung tissue (Tan S. et al., Oncotargets and Therapy 2018: 11, 2991-3002).

The two RIZ isoforms regulate cellular functions in a "Yin-Yang" fashion (Di Zazzo, Biology 2016, 5, 54; doi: 10.3390) whereby the two forms produce dual complimentary opposite reactions. Specifically, the RIZ1 protein plays the role of tumor suppressor, arresting cancer cells in the G2/M phase of the cell cycle and promoting apoptosis, while the RIZ2 protein acts as a proto-oncogene, promoting cell division. Thus, an imbalance in the amounts of RIZ1 and RIZ2 may be an important cause of cancer progression. That view is supported by research finding that silencing or deregulation of RIZ1 expression, associated with increased RIZ2 expression, has been observed in a variety of human cancers, including hepatoma, leukemia, malignant lymphoma, breast cancer, colorectal cancer, thyroid carcinoma and others.

In one aspect, the instant disclosure provides a method for regulating PRDM2 gene expression. In one embodiment, the method can regulate RIZ2 expression. In some embodiments, the method can be used to decrease RIZ2 expression. In one embodiment the RIZ2 expression is decreased in a cell using the method described herein. In some embodiments, the method described herein is used to decrease RIZ2 expression in a cell within a mammalian system. In some embodiments, the mammalian system is a human system.

In one embodiment, provided herein is a method to decrease the level of RIZ2 in a cell, that shows aberrantly high expression of RIZ2 compared to a normal cell, wherein a normal cell is a healthy cell, or a cell collected from a healthy individual, wherein a healthy individual may be an individual who does not present clinical signs of a disease or a condition. In some embodiments, a cell that shows aberrantly high expression of RIZ2 is a cell that has a cell cycle regulation disorder. In some embodiments, a cell that shows aberrantly high expression of RIZ2 is a cell that exhibits hyperplasia. In some embodiments, a cell that shows aberrantly high expression of RIZ2 is a cancer cell.

In some embodiments, provided herein is a method of decreasing RIZ2 expression specifically in a cancer cell, or a cell exhibiting hyperplasia, wherein the cell exhibits an aberrantly high expression of RIZ2. In some embodiments, the cell that exhibits aberrantly high expression of RIZ2 also exhibits a decrease in expression of RIZ1 concurrently. In some embodiments, the method provided herein is capable of decreasing RIZ2 expression, and concurrently increase expression of RIZ1. In some embodiments, the method provided herein restores a RIZ1-RIZ2 balance in a cell. In some embodiments, the method provided herein allows upregulation of RIZ1 and downregulation of RIZ2. In some embodiments, the method provided herein allows upregulation of RIZ1 by downregulation of RIZ2. In some embodiments, the method provided herein comprises contacting the cell with a RIZ2 inhibitor.

Provided herein is a method of downregulation of RIZ2 in a cell expressing elevated RIZ2 levels than that of a normal cell, and simultaneously upregulating RIZ1 levels, wherein the cell expressing elevated RIZ2 levels than that of a normal cell also exhibits a decreased RIZ1 level than that of a normal cell, the method comprises contacting the cell with a RIZ2 inhibitor described in the disclosure. In some embodiments, a normal cell is a cell that exhibits a normal cell division cycle. In one embodiment, provided herein is a method of restoring RIZ1-RIZ2 balance in a cell. In one embodiment, the ratio of RIZ1 to RIZ2 mRNA expression levels are altered by greater than at least 1.1-fold. For example, in one embodiment, the ratio of RIZ1 to RIZ2 mRNA expression levels are altered by greater than at least 1.2-fold. In one embodiment, the ratio of RIZ1 to RIZ2 mRNA expression levels are altered by greater than at least 1.3-fold. In one embodiment, the ratio of RIZ1 to RIZ2 mRNA expression levels are altered by greater than at least 1.4-fold. In one embodiment, the ratio of RIZ1 to RIZ2 mRNA expression levels are altered by greater than at least 1.5-fold. In one embodiment, the ratio of RIZ1 to RIZ2 mRNA expression levels are altered by greater than at least 1.6-fold. In one embodiment, the ratio of RIZ1 to RIZ2 mRNA expression levels are altered by greater than at least 1.7-fold. In one embodiment, the ratio of RIZ1 to RIZ2 mRNA expression levels are altered by greater than at least 1.8-fold. In one embodiment, the ratio of RIZ1 to RIZ2 mRNA expression levels are altered by greater than at least 1.9-fold. In one embodiment, the ratio of RIZ1 to RIZ2 mRNA expression levels are alters the ratio of RIZ1 to RIZ2 mRNA expression levels by at least 2-fold.

In some embodiments, the method provided herein comprises contacting the cell with a composition comprising a Retinoblastoma Protein-Interacting Zinc Finger Protein 2 (RIZ2) inhibitor. In some embodiments, the RIZ2 inhibitor is a non-naturally occurring agent, e.g., a synthetic agent. In some embodiments, the RIZ2 inhibitor is a small molecule. In some embodiments, the small molecule is designed to be specific for inhibiting RIZ2 and not inhibiting RIZ1. In some embodiments, the RIZ2 inhibitor comprises a peptide. In some embodiments, the RIZ2 inhibitor is a peptide that specifically inhibits RIZ2 in a cell, and comprises at least about 4 amino acids, at least about 4 amino acids, at least about 4 amino acids, at least about 5 amino acids, at least about 6 amino acids, at least about 7 amino acids, at least about 8 amino acids, at least about 9 amino acids, at least about 10 amino acids, at least about 11 amino acids, at least about 12 amino acids, at least about 13 amino acids, at least about 14 amino acids, at least about 15 amino acids, at least about 16 amino acids, at least about 17 amino acids, at least about 18 amino acids, at least about 19 amino acids, or at least about 20 amino acids, or more than 20 amino acids. In some embodiments, the RIZ2 inhibitor comprises a conjugated polypeptide. In some embodiments, the conjugated polypeptide comprises at least one bioactive polypeptide capable of decreasing RIZ2 level (RIZ2 inhibitor), and a moiety that confers stability, or passage across cell membrane or allows targeting the bioactive peptide to a specific cell, a tissue or an organ when applied in vivo. In some embodiments, the RIZ2 inhibitor comprises one or more polynucleotides. In some embodiments, RIZ2 inhibitor comprises a synthetic polynucleotide. In some embodiments, RIZ2 inhibitor comprises a synthetic polynucleotide such as an siRNA.

In some embodiments, the method comprises contacting the cell with a RIZ2 inhibitor wherein the RIZ2 inhibitor is present at an amount sufficient to decrease the RIZ2 level in the cell, and to increase the RIZ1 level in the cell such that the level of RIZ2 and RIZ1 are comparable to a normal cell, or such that the ratio of RIZ1 versus RIZ2 is brought back to levels similar to normal cell, i.e., a cell that has a normal proliferation rate, e.g., a normal cell cycle.

In some embodiments, the methods described herein is a method of inhibiting cell proliferation, comprising contacting a population of cells with a composition comprising a RIZ2 inhibitor.

In some embodiments, the methods described herein, when applied to a population of cells, reduces cell proliferation rate in the cell population from a hyperproliferative state to a proliferation rate similar to normal healthy cells.

In some embodiments, the methods described herein, when applied to a population of cells, results in a reduction of a cell number of the population of cells by at least 10%. In some embodiments, contacting the cells with a RIZ2 inhibitor results in a reduction of a cell number of the population of cells by at least about 15%, or by at least about 20%, at least about 25%, by at least about 30%, by at least about 35%, at least about 40%, at least about 45%, by at least about 50%, at least about 55%, at least about 60%, by at least about 65%, by at least about 70%, by at least about 75%, by at least about 80%, at least about 85%, or at least about 90%.

In some embodiments, contacting the cells with the RIZ2 inhibitor results in a reduction of a cell number of the population of cells by about 90%. In some embodiments, inhibiting cell proliferation comprises reducing the cell mass by at least 10%. %. In some embodiments, contacting the cells with a RIZ2 inhibitor results in a reduction of a cell mass of the population of cells by at least about 15%, or by at least about 20%, at least about 25%, by at least about 30%, by at least about 35%, at least about 40%, at least about 45%, by at least about 50%, at least about 55%, at least about 60%, by at least about 65%, by at least about 70%, by at least about 75%, by at least about 80%, at least about 85%, or at least about 90%.%. In some embodiments, contacting the cells with a RIZ2 inhibitor results in a reduction of a cell mass of the population of cells by at least about 15%, or by at least about 20%, at least about 25%, by at least about 30%, by at least about 35%, at least about 40%, at least about 45%, by at least about 50%, at least about 55%, at least about 60%, by at least about 65%, by at least about 70%, by at least about 75%, by at least about 80%, at least about 85%, or at least about 90%.

In some embodiments, inhibiting cell proliferation comprises reducing a cell mass by about 50%. In some embodiments, inhibiting cell proliferation comprises reducing a cell mass by about 60%. In some embodiments, inhibiting cell proliferation comprises reducing a cell mass by about 65%. In some embodiments, inhibiting cell proliferation comprises reducing a cell mass by about 70%. In some embodiments, inhibiting cell proliferation comprises reducing a cell mass by about 75%.

In some embodiments, the method described here comprises a method of treating a hyperproliferative disorder in a subject, e.g., a human subject, by administering to the subject a therapeutically effective amount of the RIZ2 inhibitor, wherein, when administered at a dose and suitable time interval reduced or ameliorated the hyperproliferative disorder in the subject. In some embodiments, the hyperproliferative disorder is cancer.

PRDM2 siRNA Designs

Provided herein is an inhibitory RNA molecule suitable for inhibiting RIZ2 expression. In some embodiments, the specific RNA molecule is suitable for therapeutic applications. synthetic small nucleic acid molecules, such as short interfering nucleic acid (siNA), short interfering RNA (siRNA), double-stranded RNA (dsRNA), micro-RNA (miRNA), and short hairpin RNA (shRNA) molecules capable of modulating gene expression in cells by RNA inference (RNAi). The siNA molecules of the invention can be chemically modified. The use of chemically modified siNA can improve various properties of native siRNA molecules through increased resistance to nuclease degradation in vivo and/or improved cellular uptake. The chemically modified siNA molecules of the instant invention provide useful reagents and methods for a variety of therapeutic, cosmetic, cosmeceutical, prophylactic, diagnostic, agricultural, target validation, genomic discovery, genetic engineering and pharmacogenomic applications.

In some embodiments, the siRNA binds to at least 5, 6, 7, 8, 9, 10 contiguous nucleotides that can bind to at least 5, 6, 7, 8, 9, 10 contiguous nucleotides of the PRDM2 gene.

In some embodiments, the siRNA binds to at least 5, 6, 7, 8, 9, 10 contiguous nucleotides that can bind to at least 5, 6, 7, 8, 9, 10 contiguous nucleotides of the RIZ1 or RIZ2 gene.

In some embodiments, the siRNA binds to at least 5, 6, 7, 8, 9, 10 contiguous nucleotides that can bind to at least 5, 6, 7, 8, 9, 10 contiguous nucleotides of the RIZ2 gene.

In some embodiments, the siRNA binds to at least 5, 6, 7, 8, 9, 10 contiguous nucleotides that can bind to at least 5, 6, 7, 8, 9, 10 contiguous nucleotides of the RIZ2 gene but not the RIZ1 gene.

In some embodiments, the siRNA binds specifically to at least 5, 6, 7, 8, 9, 10 contiguous nucleotides of the RIZ2 gene, and predominantly affects RIZ2 gene expression without negatively affecting RIZ1 expression levels.

In one aspect, the present disclosure provides one or more siRNA sequences capable of reducing (e.g., silencing) the expression of RIZ2 gene, without negatively affecting the expression of RIZ1 gene, and specifically, without reducing the expression of RIZ1 gene. More specifically, provided herein are siRNA sequences that reduce or inhibit the expression of a RIZ2 gene, and induces the expression of RIZ1 gene. In some embodiments, the siRNA sequences provided herein are capable of reducing, or inhibiting human RIZ2 expression, without inhibiting human RIZ1 expression. In one embodiment, the present disclosure is based on the surprising and unexpected finding that one or more siRNA targeting a common region of the RIZ2 and RIZ1 gene, predominantly inhibits RIZ2 but spares RIZ1, even though the siRNA shares homology to both the genes/gene products.

In some embodiments, the siRNA is designed to target a region between 1-500 nucleotides from the 5'-end of the RIZ2 mRNA. In some embodiments, the siRNA is designed to target a region between 10-500 nucleotides from the 5'-end of the RIZ2 mRNA. In some embodiments, the siRNA is designed to target a region between 100-500 nucleotides from the 5'-end of the RIZ2 mRNA. In some embodiments, the siRNA is designed to target a region between 200-500 nucleotides from the 5'-end of the RIZ2 mRNA. In some embodiments, the siRNA is designed to target a region between 500-1000 nucleotides from the 5'-end of the RIZ2 mRNA. In some embodiments the siRNA is designed to target a region between 200-2000 nucleotides from the 5'-end of the RIZ2 mRNA. In some embodiments, the siRNA is designed to target a region between 500-2500 nucleotides from the 5'-end of the RIZ2 mRNA. In some embodiments, the siRNA is designed to target a region between 1000-2500 nucleotides from the 5'-end of the RIZ2 mRNA. In some embodiments, the siRNA is designed to target a region between 1600-2200 nucleotides from the 5'-end of the RIZ2 mRNA. In some embodiments, the siRNA is designed to target a region between 1800-2200 nucleotides from the 5'-end of the RIZ2 mRNA. In some embodiments, the siRNA is designed to target a region between 1900-1950 nucleotides from the 5'-end of the RIZ2 mRNA. In some embodiments, the siRNA is designed to target a region between 1920-1940 nucleotides from the 5'-end of the RIZ2 mRNA. In some embodiments, the siRNA is designed to target a region between 2000-3500 nucleotides from the 5'-end of the RIZ2 mRNA. In some embodiments, the siRNA is designed to target a region between 1000-5000 nucleotides from the 5'-end of the RIZ2 mRNA. In some embodiments, the siRNA is designed to target a region between 1500-3000 nucleotides from the 5'-end of the RIZ2 mRNA. In some embodiments, the siRNA is designed to target a region between 2500-3500 nucleotides from the 5'-end of the RIZ2 mRNA. In some embodiments, the siRNA is designed to target a region between 3500-5000 nucleotides from the 5'-end of the RIZ2 mRNA. In some embodiments, the siRNA is designed to target a region between 4000-5000 nucleotides from the 5'-end of the RIZ2 mRNA. In some embodiments, the siRNA is designed to target a region between 4250-4500 nucleotides from the 5'-end of the RIZ2 mRNA. In some embodiments, the siRNA is designed to target a region between 4300-4400 nucleotides from the 5'-end of the RIZ2 mRNA. In some embodiments, the siRNA is designed to target a region between 4500-5000 nucleotides from the 5'-end of the RIZ2 mRNA. In some embodiments, the siRNA is designed to target a region between 4550-4700 nucleotides from the 5'-end of the RIZ2 mRNA. In some embodiments, the siRNA is designed to target a region between 4560-4600 nucleotides from the 5'-end of the RIZ2 mRNA. In some embodiments, the siRNA is designed to target a region between 4500-6000 nucleotides from the 5'-end of the RIZ2 mRNA. In some embodiments, the siRNA is designed to target a region between 5000-6140 nucleotides from the 5'-end of the RIZ2 mRNA. In some embodiments, the siRNA is designed to target a region between 6050-6155 nucleotides from the 5'-end of the RIZ2 mRNA. In some embodiments, the siRNA is designed to target a region between 6090-6120 nucleotides from the 5'-end of the RIZ2 mRNA.

Provided below is an exemplary list of sequences comprising positive and negative strands of siRNA shown in the exemplary studies for the invention disclosed herein.

TABLE 2

RIZ-specific siRNA

| Name | SEQ ID NO | (Sense strand) | SEQ ID NO | (Antisense stranded) |
| --- | --- | --- | --- | --- |
| ARIZ-1 011 | | 5'-GGGAGAGAUGAG AGAAAdTdT-3' | 10 | 5'-UUUCUCUCUCAU CUCUCCdTdT-3' |
| ARIZ 61-047 | | 5'Disulfide-GGGAGAGA4GAGAG AGAAAdTdT-3' (where4 = 2'-methoxyuridine) | 11 | 5'P-446C6C6CUCAUC 6C6CCCdTdT-3' (where 4 = 2'-methoxyuridine; 6 = 2'-Fluoro-deoxyuridine; bold + underline = phosphorothioate) |
| ARIZ-2 012 | | 5'-GUGUAGUGCUGUAA AGAAAdTdT-3' | 12 | 5'-UUUCUUUACAGCA CUACACdTdT-3' |
| ARIZ-3 013 | | 5'-GCAAAAUGUCGUCG TAAUAAddT-3' | 13 | 5'-UUAUUCGACGACA UUUUGCdTdT-3' |
| ARIZ-4 014 | | 5'-UGGAAAAGGUGUCG ACAAUdTdT-3' | 14 | 5'-AUUGUCGACACCU UUUCCAdTdT-3' |
| ARIZ-5 015 | | 5'-GGACUUCAGGAACU UCCUGdTdT-3' | 15 | 5'-CAGGAAGUUCCUG AAGUCCdTdT-3' |
| ARIZ-7 062 | | 5'-CUUAAUAACUAGAG GAGAAdTdT-3' | 16 | 5'P-UUCUCCUCUAGUUA TUUAAGddT-3' |
| ARIZ-8 063 | | 5'-CGCAAAGGAUACGA AAUCdTdT-3' | 17 | 5'P-GAUUCCGUAUCCUU UGCCGdTdT-3' |

TABLE 2-continued

RIZ-specific siRNA

| Name | SEQ ID NO | (Sense strand) | SEQ ID NO | (Antisense stranded) |
|---|---|---|---|---|
| ARIZ-9 064 | 5'-GGAUAAGCACUACG GCAAAdTdT-3' | | 18 | 5'P-UUUGCCGUAGUGCU UAUCCdTdT-3' |

Provided herein is a number of double stranded polynucleotide compositions comprising a sense strand and an antisense strand presented in Table 2, wherein the left column comprising the sense strand sequence for each double stranded polynucleotide pairs with an antisense strand sequence presented on the right column within the row. In one embodiment, the siRNA is 21 nucleotides in length. In one embodiment, the siRNA comprises a 1, 2, or 3 nucleotide single nucleotide overhang at the 5'- or the 3'-end.

Therefore, in one embodiment, provided herein is a RIZ 2 inhibitor comprising a double stranded polynucleotide comprising a sense strand of SEQ ID NO: 1, and an antisense strand of SEQ ID NO: 10.

In one embodiment, provided herein is a RIZ 2 inhibitor comprising a double stranded polynucleotide comprising a sense strand of SEQ ID NO: 6 and an antisense strand of SEQ ID NO: 11.

In one embodiment, provided herein is a RIZ 2 inhibitor comprising a double stranded polynucleotide comprising a sense strand of SEQ ID NO: 2, and an antisense strand of SEQ ID NO: 12.

In one embodiment, provided herein is a RIZ 2 inhibitor comprising a double stranded polynucleotide comprising a sense strand of SEQ ID NO: 3, and an antisense strand of SEQ ID NO: 13.

In one embodiment, provided herein is a RIZ 2 inhibitor comprising a double stranded polynucleotide comprising a sense strand of SEQ ID NO: 4, and an antisense strand of SEQ NO: 14.

In one embodiment, provided herein is a RIZ 2 inhibitor comprising a double stranded polynucleotide comprising a sense strand of SEQ ID NO: 5, and an antisense strand of SEQ ID NO: 15.

In one embodiment, provided herein is a RIZ 2 inhibitor comprising a double stranded polynucleotide comprising a sense strand of SEQ ID NO: 7, and an antisense strand of SEQ ID NO: 16.

In one embodiment, provided herein is a RIZ 2 inhibitor comprising a double stranded polynucleotide comprising a sense strand of SEQ ID NO: 8, and an antisense strand of SEQ NO: 17.

In one embodiment, provided herein is a RIZ 2 inhibitor comprising a double stranded polynucleotide comprising a sense strand of SEQ ID NO: 9, and an antisense strand of SEQ NO: 18.

In one aspect, the present invention provides double stranded polynucleotide compositions for inhibiting RIZ2 mRNA expression. In one embodiment, the double stranded polynucleotide may occur without any modifications. In one embodiment, one or more nucleotides within the sense or antisense molecule is modified. For example ARIZ-0047 sense and antisense strands have the same nucleotide sequence as ARIZ-0011 but comprises modified nucleotides, e.g., the sense strand comprises a disulfide modification at the 5'-end. In one embodiment, the oligomer comprises one modified nucleotide, e.g., a 2'-methoxyuridine interrupting the stretch of non-modified nucleotides, e.g., the 9$^{th}$ nucleotide residue from the 5'-end of SEQ ID NO: 6. In one embodiment, the sense or the antisense strand may comprise more than one modifications, For example, the antisense strand of ARIZ-0047 (SEQ ID NO: 11) comprises two 5'-P'-methoxyuridine residues in tandem, and a terminal 3'-dinucleotide at the 3' end comprise phosphorothioate bonds.

Contemplated herein are one or more modifications to either the sense strand, or the antisense strand for any one of the double stranded polynucleotide compositions presented herein in table 1. In some embodiments, one or both the strands are designed to comprise a modification. In some embodiments, one strand may comprise an interrupted or gapped motif and the other strand may comprise a gapped motif, a hemimer motif, a blockmer motif, a fully modified motif, a positionally modified motif or an alternating motif. An "interrupted" or "gapped" motif comprises a modified nucleoside interrupting a contiguous sequence of nucleosides, such that the nucleotide stretch is divided into 2, or preferably 3 regions, e.g., an internal region flanked by two external regions. The regions are interrupted and separated from each other at least by having modified (different) sugar groups that comprise the nucleosides. In some embodiments, the nucleosides with different sugar groups comprise oligomeric compound p-D-ribonucleosides, or a 2' modified nucleosides, or a 4'-thio modified nucleosides, or a 4'-thio-2'-modified nucleosides, or a bicyclic sugar modified nucleosides.

In some embodiments, the internal region or the gap generally comprises p-D-ribonucleosides but can be a sequence of sugar modified nucleosides. In some embodiments, the nucleosides located in the gap of a gapped oligomeric compound have different sugar groups than both of the wings. In some embodiments, the gapped oligomeric compounds are "symmetric". In some embodiments, the gapped oligomeric compounds are "asymmetric". A gapmer having the same uniform sugar modification in each of the wings may be a symmetric gapped oligomeric compound. A gapmer having different uniform modifications in each wing is termed an asymmetric gapped oligomeric compound. In some embodiments, the gapped oligomeric compounds such as these can have for example both wings comprising 4'-thio modified nucleosides (symmetric gapmer) and a gap comprising p-D-ribonucleosides or modified nucleosides other than 4'-thio modified nucleosides. In some embodiments, the asymmetric gapped oligomeric compounds may comprise one wing comprising 2'-OCH 3 modified nucleosides; and the other wing comprising 4'-thio modified nucleosides with the internal region (gap) comprising p D-ribonucleosides or sugar modified nucleosides that are other than 4'-thio or 2'-OCH 3 modified nucleosides.

In some embodiments, each strand of the compositions of the present invention can be modified to fulfil a particular role in for example the siRNA pathway. The antisense strand can be modified at the 5'-end to enhance its role in one region of the RISC while 5 the 3'-end can be modified differentially to enhance its role in a different region of the RISC.

In one embodiment, siRNAs comprise a T overhang. In some embodiments, the T overhang comprises a single Uridine (interchangeably designated as Thymidine (T) in the sequences presented herein, or two Uridine nucleotide residues in tandem (e.g., dTdT).

In some embodiments, one or more residues are linked by phosphorothioate bonds.

In one aspect, provided herein is a use of any one of the RIZ2 siRNAs described in the specification for treatment of a hyperproliferative disorder, e.g., cancer. In one aspect, provided herein is a use of any one of the RIZ2 siRNAs described in the specification for preparing a medicament suitable for the treatment of a hyperproliferative disorder, e.g., cancer.

ARIZ siRNAs-011 through -014 are complementary to sequences shared by both the RIZ1 and RIZ2 mRNA transcripts. ARIZ-015 is complementary to the last 19 bases at the 3' end of the RIZ2 mRNA, and contains 10 nucleotides unique to RIZ2 mRNA that correspond to four terminal amino acids unique to RIZ2, as well as 9 nucleotides common to both RIZ1 and RIZ2 mRNA. ARIZ-047 is the same sequence as ARIZ-011 except for the indicated base modifications.

ARIZ siRNAs-062 through -064 are complementary to sequences unique to RIZ2 mRNA.

In one embodiment, provided herein is an siRNA that targets only RIZ2 and spares RIZ1 mRNA. In one embodiment, provided herein is an siRNA that targets only RIZ1 but does not affect RIZ2 mRNA. In one embodiment, provided herein is an siRNA that targets RIZ2 mRNA, and spares RIZ1 mRNA, and that exerts an inhibitory effect on RIZ2 mRNA. Provided herein are surprising results that, despite the fact that an siRNA disclosed herein can target either of RIZ1 or RIZ2 mRNA, Applicant's observations indicate that the siRNA specifically inhibits RIZ2 mRNA. Yet more surprising was the observation, as presented herein, that the siRNA results in increase of RIZ1 mRNA level. Even further surprising are the observations disclosed for the first time herein, is that the siRNA of the invention can preferentially lead to cell death of cancer cells, and spares the non-cancer cells. This is highly unexpected in a condition where the siRNA can target a region common to both RIZ2 and RIZ1 mRNA and therefore potentially inhibit both mRNAs.

In one embodiment, the siRNA provided herein targets a RIZ2 mRNA, which when present at a higher concentration in a given cell, e.g., a diseased cell, a cell with hyperproliferative disorder such as a cancer cell is available to manipulation by the siRNA, compared to the concurrent low concentration of the RIZ1 mRNA as occurs in a diseased cell, e.g., a cancer cell. Without wishing to be bound by any theory, it may be possible that once the siRNA of the invention targets a RIZ2 mRNA which is more prone to be targeted being at a higher concentration than RIZ1 mRNA in a diseased cell, the siRNA inhibits RIZ2 expression, leading to a concomitant increase in RIZ1 mRNA. Increase in RIZ1 mRNA can help reset the cell cycle homeostasis and the cell death may be achieved for the aberrantly proliferative cells, e.g., cancer cells.

In some embodiments, the RIZ2 inhibitor comprising any one of the siRNA in Table 2 reduces the expression of RIZ2 mRNA in a treated cell by at least 5% compared to an untreated cell. In some embodiments, a RIZ2 siRNA reduces the expression of RIZ2 mRNA by at least 6%. In some embodiments, a RIZ2 siRNA reduces the expression of RIZ2 mRNA by at least 7%. In some embodiments, a RIZ2 siRNA reduces the expression of RIZ2 mRNA by at least 8%. In some embodiments, a RIZ2 siRNA reduces the expression of RIZ2 mRNA by at least 9%. In some embodiments, a RIZ2 siRNA reduces the expression of RIZ2 mRNA by at least 10%. In some embodiments, a RIZ2 siRNA reduces the expression of RIZ2 mRNA by at least 11%. In some embodiments, a RIZ2 siRNA reduces the expression of RIZ2 mRNA by at least 12%. In some embodiments, a RIZ2 siRNA reduces the expression of RIZ2 mRNA by at least 13%. In some embodiments, a RIZ2 siRNA reduces the expression of RIZ2 mRNA by at least 14%. In some embodiments, a RIZ2 siRNA reduces the expression of RIZ2 mRNA by at least 15%. In some embodiments, a RIZ2 siRNA reduces the expression of RIZ2 mRNA by at least 16%. In some embodiments, a RIZ2 siRNA reduces the expression of RIZ2 mRNA by at least 17%. In some embodiments, a RIZ2 siRNA reduces the expression of RIZ2 mRNA by at least 18%. In some embodiments, a RIZ2 siRNA reduces the expression of RIZ2 mRNA by at least 19%. In some embodiments, a RIZ2 siRNA reduces the expression of RIZ2 mRNA by at least 20%. In some embodiments, a RIZ2 siRNA reduces the expression of RIZ2 mRNA by at least 21%. In some embodiments, a RIZ2 siRNA reduces the expression of RIZ2 mRNA by at least 22%. In some embodiments, a RIZ2 siRNA reduces the expression of RIZ2 mRNA by at least 23%. In some embodiments, a RIZ2 siRNA reduces the expression of RIZ2 mRNA by at least 24%. In some embodiments, a RIZ2 siRNA reduces the expression of RIZ2 mRNA by at least 25%. In some embodiments, a RIZ2 siRNA reduces the expression of RIZ2 mRNA by at least 26%. In some embodiments, a RIZ2 siRNA reduces the expression of RIZ2 mRNA by at least 27%. In some embodiments, a RIZ2 siRNA reduces the expression of RIZ2 mRNA by at least 28%. In some embodiments, a RIZ2 siRNA reduces the expression of RIZ2 mRNA by at least 29%. In some embodiments, a RIZ2 siRNA reduces the expression of RIZ2 mRNA by at least 30%. In some embodiments, a RIZ2 siRNA reduces the expression of RIZ2 mRNA by at least 31%. In some embodiments, a RIZ2 siRNA reduces the expression of RIZ2 mRNA by at least 32%. In some embodiments, a RIZ2 siRNA reduces the expression of RIZ2 mRNA by at least 33%. In some embodiments, a RIZ2 siRNA reduces the expression of RIZ2 mRNA by at least 34%. In some embodiments, a RIZ2 siRNA reduces the expression of RIZ2 mRNA by at least 35%. In some embodiments, a RIZ2 siRNA reduces the expression of RIZ2 mRNA by at least 36%. In some embodiments, a RIZ2 siRNA reduces the expression of RIZ2 mRNA by at least 37%. In some embodiments, a RIZ2 siRNA reduces the expression of RIZ2 mRNA by at least 38%. In some embodiments, a RIZ2 siRNA reduces the expression of RIZ2 mRNA by at least 39%. In some embodiments, a RIZ2 siRNA reduces the expression of RIZ2 mRNA by at least 40%. In some embodiments, a RIZ2 siRNA reduces the expression of RIZ2 mRNA by at least 41%. In some embodiments, a RIZ2 siRNA reduces the expression of RIZ2 mRNA by at least 42%. In some embodiments, a RIZ2 siRNA reduces the expression of RIZ2 mRNA by at least 43%. In some embodiments, a RIZ2 siRNA reduces the expression of RIZ2 mRNA by at least 44%. In some embodiments, a RIZ2 siRNA reduces the expression of RIZ2 mRNA by at least 45%. In some embodiments, a RIZ2 siRNA reduces the expression of RIZ2 mRNA by at least 46%. In some embodiments, a RIZ2 siRNA reduces the expression of RIZ2 mRNA by at least 47%. In some embodiments, a RIZ2 siRNA reduces the expression of RIZ2 mRNA by at least 48%. In some embodiments, a RIZ2 siRNA reduces the expression of RIZ2 mRNA by at least 49%. In some embodiments, a RIZ2 siRNA reduces the expression of RIZ2 mRNA by at least 50%. In some embodiments, a RIZ2 siRNA reduces the expression of RIZ2 mRNA by at least 51%. In some embodiments, a RIZ2 siRNA reduces the expression of RIZ2 mRNA by at least 52%. In some embodiments, a RIZ2 siRNA reduces the expression of RIZ2 mRNA by at least 53%. In some embodiments, a RIZ2 siRNA reduces the expression of RIZ2 mRNA by at least 54%. In some embodiments, a RIZ2 siRNA reduces the expression of RIZ2 mRNA by at least 55%. In some embodiments, a RIZ2 siRNA reduces the expression of RIZ2 mRNA by at least 56%. In some embodiments, a RIZ2 siRNA reduces the expression of RIZ2 mRNA by at least 57%. In some embodiments, a RIZ2 siRNA reduces the expression of RIZ2 mRNA by at least 58%. In some embodiments, a RIZ2 siRNA reduces the expression of RIZ2 mRNA by at least 59%. In some embodiments, a RIZ2 siRNA reduces the expression of RIZ2 mRNA by at least 60%. In some embodiments, a RIZ2 siRNA reduces the expression of RIZ2 mRNA by at least 61%. In some embodiments, a RIZ2 siRNA reduces the expression of RIZ2 mRNA by at least 62%. In some embodiments, a RIZ2 siRNA reduces the expression of RIZ2 mRNA by at least 63%. In some embodiments, a RIZ2 siRNA reduces the expression of RIZ2 mRNA by at least 64%. In some embodiments, a RIZ2 siRNA reduces the expression of RIZ2 mRNA by at least 65%. In some embodiments, a RIZ2 siRNA reduces the expression of RIZ2 mRNA by at least 66%. In some embodiments, a RIZ2 siRNA reduces the expression of RIZ2 mRNA by at least 67%. In some embodiments, a RIZ2 siRNA reduces the expression of RIZ2 mRNA by at least 68%. In some embodiments, a RIZ2 siRNA reduces the expression of RIZ2 mRNA by at least 69%. In some embodiments, a RIZ2 siRNA reduces the expression of RIZ2 mRNA by at least 70%. In some embodiments, a RIZ2 siRNA reduces the expression of RIZ2 mRNA by at least 71%. In some embodiments, a RIZ2 siRNA reduces the expression of RIZ2 mRNA by at least 72%. In some embodiments, a RIZ2 siRNA reduces the expression of RIZ2 mRNA by at least 73%. In some embodiments, a RIZ2 siRNA reduces the expression of RIZ2 mRNA by at least 74%. In some embodiments, a RIZ2 siRNA reduces the expression of RIZ2 mRNA by at least 75%. In some embodiments, a RIZ2 siRNA reduces the expression of RIZ2 mRNA by at least 76%. In some embodiments, a RIZ2 siRNA reduces the expression of RIZ2 mRNA by at least 77%. In some embodiments, a RIZ2 siRNA reduces the expression of RIZ2 mRNA by at least 78%. In some embodiments, a RIZ2 siRNA reduces the expression of RIZ2 mRNA by at least 79%. In some embodiments, a RIZ2 siRNA reduces the expression of RIZ2 mRNA by at least 80%. In some embodiments, a RIZ2 siRNA reduces the expression of RIZ2 mRNA by at least 81%. In some embodiments, a RIZ2 siRNA reduces the expression of RIZ2 mRNA by at least 82%. In some embodiments, a RIZ2 siRNA reduces the expression of RIZ2 mRNA by at least 83%. In some embodiments, a RIZ2 siRNA reduces the expression of RIZ2 mRNA by at least 84%. In some embodiments, a RIZ2 siRNA reduces the expression of RIZ2 mRNA by at least 85%. In some embodiments, a RIZ2 siRNA reduces the expression of RIZ2 mRNA by at least 86%. In some embodiments, a RIZ2 siRNA reduces the expression of RIZ2 mRNA by at least 87%. In some embodiments, a RIZ2 siRNA reduces the expression of RIZ2 mRNA by at least 88%. In some embodiments, a RIZ2 siRNA reduces the expression of RIZ2 mRNA by at least 89%. In some embodiments, a RIZ2 siRNA reduces the expression of RIZ2 mRNA by at least 90%.

In some embodiments, a RIZ2 siRNA reduces the expression of RIZ2 mRNA as compared to expression of a housekeeping gene in the cells. exemplary housekeeping genes are GAPDH, or beta actin gene. In some embodiments, a RIZ2 siRNA reduces the expression of RIZ2 mRNA as compared to the expression of RIZ2 mRNA in a control cell or a population of control cells. Exemplary housekeeping genes are GAPDH, or beta actin gene.

In one embodiment, provided herein is a method of restoring RIZ1-RIZ2 balance in a cell. In one embodiment, the ratio of RIZ1 to RIZ2 mRNA expression levels are altered by greater than at least 1.1-fold. For example, in one embodiment, the ratio of RIZ1 to RIZ2 mRNA expression levels are altered by greater than at least 1.2-fold. In one embodiment, the ratio of RIZ1 to RIZ2 mRNA expression levels are altered by greater than at least 1.3-fold. In one embodiment, the ratio of RIZ1 to RIZ2 mRNA expression levels are altered by greater than at least 1.4-fold. In one embodiment, the ratio of RIZ1 to RIZ2 mRNA expression levels are altered by greater than at least 1.5-fold. In one embodiment, the ratio of RIZ1 to RIZ2 mRNA expression levels are altered by greater than at least 1.6-fold. In one embodiment, the ratio of RIZ1 to RIZ2 mRNA expression levels are altered by greater than at least 1.7-fold. In one embodiment, the ratio of RIZ1 to RIZ2 mRNA expression levels are altered by greater than at least 1.8-fold. In one embodiment, the ratio of RIZ1 to RIZ2 mRNA expression levels are altered by greater than at least 1.9-fold. In one embodiment, the ratio of RIZ1 to RIZ2 mRNA expression levels are alters the ratio of RIZ1 to RIZ2 mRNA expression levels by at least 2-fold.

In some embodiments, the RIZ2 inhibitor is an siRNA that reduces cell proliferation of a diseased cell (e.g. cancer cell) by at least 10%. In some embodiments the RIZ2 inhibitor siRNA reduces cancer cell proliferation by about 15%. In some embodiments the RIZ2 inhibitor siRNA reduces cancer cell proliferation by about 20%. In some embodiments the RIZ2 inhibitor siRNA reduces cancer cell proliferation by about 25%. In some embodiments the RIZ2 inhibitor siRNA reduces cancer cell proliferation by about 30%. In some embodiments the RIZ2 inhibitor siRNA reduces cancer cell proliferation by about 35%. In some embodiments the RIZ2 inhibitor siRNA reduces cancer cell proliferation by about 40%. In some embodiments the RIZ2 inhibitor siRNA reduces cancer cell proliferation by about 45%. In some embodiments the RIZ2 inhibitor siRNA reduces cancer cell proliferation by about 50%. In some embodiments the RIZ2 inhibitor siRNA reduces cancer cell proliferation by about 55%. In some embodiments the RIZ2 inhibitor siRNA reduces cancer cell proliferation by about 60%. In some embodiments the RIZ2 inhibitor siRNA reduces cancer cell proliferation by about 65%. In some embodiments the RIZ2 inhibitor siRNA reduces cancer cell proliferation by about 70%. In some embodiments the RIZ2 inhibitor siRNA reduces cancer cell proliferation by about 75%. In some embodiments the RIZ2 inhibitor siRNA reduces cancer cell proliferation by about 80%. In some embodiments the RIZ2 inhibitor siRNA reduces cancer cell proliferation by about 81%. In some embodiments the RIZ2 inhibitor siRNA reduces cancer cell proliferation by about 82%. In some embodiments the RIZ2 inhibitor siRNA reduces cancer cell proliferation by about 83%. In some embodiments the RIZ2 inhibitor siRNA reduces cancer cell proliferation by about 84%. In some embodiments the RIZ2 inhibitor siRNA reduces cancer cell proliferation by about 85%. In some embodiments the RIZ2 inhibitor siRNA reduces cancer cell proliferation by about 86%. In some embodiments the RIZ2 inhibitor siRNA reduces cancer cell proliferation by about 87%. In some embodiments the RIZ2 inhibitor siRNA reduces cancer cell proliferation by about 88%. In some embodiments the RIZ2 inhibitor siRNA reduces cancer cell proliferation by about 89%. In some embodiments the RIZ2 inhibitor siRNA reduces cancer cell proliferation by about 90%. In some embodiments the RIZ2 inhibitor siRNA reduces cancer cell proliferation by about 91%. In some embodiments the RIZ2 inhibitor siRNA reduces cancer cell proliferation by about 92%. In some embodiments the RIZ2 inhibitor siRNA reduces cancer cell proliferation by about 93%. In some embodiments the RIZ2 inhibitor siRNA reduces cancer cell proliferation by about 94%. In some embodiments the RIZ2 inhibitor siRNA reduces cancer cell proliferation by about 95%. In some embodiments the RIZ2 inhibitor siRNA reduces cancer cell proliferation by about 96%. In some embodiments the RIZ2 inhibitor siRNA reduces cancer cell proliferation by about 97%. In some embodiments the RIZ2 inhibitor siRNA reduces cancer cell proliferation by about 98%.

In some embodiments the RIZ2 inhibitor siRNA reduces cancer cell proliferation by about 35%. In some embodiments the RIZ2 inhibitor siRNA reduces cancer cell proliferation by about 40%. In some embodiments the RIZ2 inhibitor siRNA reduces cancer cell proliferation by about 45%. In some embodiments the RIZ2 inhibitor siRNA reduces cancer cell proliferation by about 50%. In some embodiments the RIZ2 inhibitor siRNA reduces cancer cell proliferation by about 55%. In some embodiments the RIZ2 inhibitor siRNA reduces cancer cell proliferation by about 60%. In some embodiments the RIZ2 inhibitor siRNA reduces cancer cell proliferation by about 65%. In some embodiments the RIZ2 inhibitor siRNA kills cancer cells by about 70%. In some embodiments the RIZ2 inhibitor siRNA kills cancer cells by about 75%. In some embodiments the RIZ2 inhibitor siRNA kills cancer cells by about 80%. In some embodiments the RIZ2 inhibitor siRNA kills cancer cells by about 81%. In some embodiments the RIZ2 inhibitor siRNA kills cancer cells by about 82%. In some embodiments the RIZ2 inhibitor siRNA kills cancer cells by about 83%. In some embodiments the RIZ2 inhibitor siRNA kills cancer cells by about 84%. In some embodiments the RIZ2 inhibitor siRNA kills cancer cells by about 85%. In some embodiments the RIZ2 inhibitor siRNA kills cancer cells by about 86%. In some embodiments the RIZ2 inhibitor siRNA kills cancer cells by about 87%. In some embodiments the RIZ2 inhibitor siRNA kills cancer cells by about 88%. In some embodiments the RIZ2 inhibitor siRNA kills cancer cells by about 89%. In some embodiments the RIZ2 inhibitor siRNA kills cancer cells by about 90%. In some embodiments the RIZ2 inhibitor siRNA kills cancer cells by about 91%. In some embodiments the RIZ2 inhibitor siRNA kills cancer cells by about 92%. In some embodiments the RIZ2 inhibitor siRNA kills cancer cells by about 93%. In some embodiments the RIZ2 inhibitor siRNA kills cancer cells by about 94%. In some embodiments the RIZ2 inhibitor siRNA kills cancer cells by about 95%. In some embodiments the RIZ2 inhibitor siRNA kills cancer cells by about 96%. In some embodiments the RIZ2 inhibitor siRNA kills cancer cells by about 97%. In some embodiments the RIZ2 inhibitor siRNA kills cancer cells by about 98%.

In one embodiment the RIZ2 inhibitor siRNA may reduce tumor cell mass by at least about 10%. In one embodiment the RIZ2 inhibitor siRNA may reduce cell mass (e.g. tumor cell mass) by about 50% compared to the untreated cells, or compared to a control cell population. In some embodiments, the reduction in cell mass may be greater than 50%, e.g., by about 55%, 60%, 65%, 70%, 75%, 80%, 85%, or 90%.

In one embodiment, the RIZ2 inhibitor siRNA does not significantly affect a non-cancer cell. In one embodiment, the RIZ2 inhibitor siRNA kills cancer cells by about 2 fold, 2.2 fold, In some embodiments, one or more siRNAs are formulated into pharmaceutical compositions for use in treating a hyperproliferative disorder, or a neoplasia, e.g., breast cancer, colon cancer, endometrial cancer, esophageal cancer, glioma, kidney cancer, leukemia, lymphoma, lung cancer, liver cancer, parathyroid cancer, pituitary cancer, meningiomas, myeloma, neuroblastoma, prostate cancer, or thyroid cancers.

siRNA Delivery

In one aspect, the siRNA of the invention is encapsulated in a liposome.

In another aspect, the siRNA of the invention is a naked double stranded molecule.

In one embodiment, the siRNA of the invention is conjugated to a cell targeting moiety. In one embodiment, the siRNA of the invention is associated with a cell targeting moiety. In one embodiment, the siRNA is associated with a cell targeting moiety that is capable of targeting a cell surface element. In an exemplary embodiment, the cell targeting moiety targets a cancer cell, or a hyperproliferative cell.

In one embodiment, the cell targeting moiety is a ligand, and antibody or an antibody fragment, a single chain antibody, a peptide or an aptamer. In one embodiment, the cell targeting moiety is a cell-penetrating peptide. In some embodiments, the delivery system comprises one or more of lipids, cyclodextrin, chitosan, carbohydrate polymers, elastin-like polymers (ELP), calcium phosphate polymers or combinations thereof.

In some embodiments, the delivery system comprises cyclodextrin.

In some embodiments, the delivery system comprises chitosan.

In some embodiments, the delivery system comprises carbohydrate polymers.

In some embodiments, the delivery system comprises elastin-like polymers (ELP). In one embodiment, the targeted delivery system comprises passively targeted nanocarriers. "Passively" targeted nanocarriers utilize the enhanced permeability and retention (EPR) effect.

In some embodiments, specific molecules or ligands on cancer cell surface are targeted, with e.g., an antibody or a fragment thereof. For example, single chain anti-prostate stem cell antigen (PSCA) antibody (scAb$_{PSCA}$) as a specific 'address tag' for prostate cancer targeted imaging and therapy (Ling Y, Wei K, Luo Y, Gao X, Zhong S. Dual docetaxel/superparamagnetic iron oxide loaded nanoparticles for both targeting magnetic resonance imaging and cancer therapy. *Biomaterials.* 2011; 32:7139-50). For example, Hadjipanayis et al. employed an anti-epidermal growth factor receptor (EGFR) deletion mutant antibody to fabricate iron oxide nanoparticles for targeted imaging and therapeutic treatment of glioblastoma (Hadjipanayis C G, Machaidze R, Kaluzova M, Wang L, Schuette A J, Chen H. et al. EGFRvIII antibody-conjugated iron oxide nanoparticles for magnetic resonance imaging-guided convection-enhanced delivery and targeted therapy of glioblastoma. *Cancer Res.* 2010; 70:6303-12). For example, Chen and Shuai et al. used a CD3 single chain antibody (scAb$_{CD3}$) functionalized nonviral polymeric vector for gene delivery to T cells (Chen G, Chen W, Wu Z, Yuan R, Li H, Gao J. et al. MRI-visible polymeric vector bearing CD3 single chain antibody for gene delivery to T cells for immunosuppression. *Biomaterials.* 2009; 30:1962-70). Any of these techniques can be adapted into the siRNA delivery mechanisms contemplated herein.

In one embodiment, the siRNA is associated with one or more lipid components, e.g., a cationic lipid. In one embodiment, the siRNA is associated with one or more lipid components, e.g., at least a cationic lipid and an anionic lipid. In one embodiment, the siRNA is modified with a polyethylene glycol (PEG) molecule. In one embodiment, the siRNA is associated in a complex comprising one or more lipids and a PEG. In one embodiment, the siRNA is associated in a complex comprising one or more lipids and a PEG wherein the PEG has a fixed length. In one embodiment, the PEG comprises a chain having about 20-about 120 carbon atoms. In one embodiment, the PEG comprises a chain having about 40-120 carbon atoms. In one embodiment, the PEG comprises a chain having about 60-120 carbon atoms. In one embodiment, the PEG comprises a chain having about 80-120 carbon atoms. In one embodiment, the PEG comprises a chain having about 100-120 carbon atoms. In one embodiment, the PEG comprises a chain having about 20-40 carbon atoms. In one embodiment, the PEG comprises a chain having about 20-60 carbon atoms. In one embodiment, the PEG comprises a chain having about 20-80 carbon atoms. In one embodiment, the PEG comprises a chain having about 20-100 carbon atoms. In some embodiments, the PEG is about 2000 kDa.

In one embodiment, the siRNA of the invention may be delivered via a nanoparticle. In one embodiment, the nanoparticle may be a lipid nanoparticle. In one embodiment, the nanoparticle may comprise a calcium phosphate nanoparticle. In some embodiments, the calcium phosphate nanoparticle comprises more than one siRNA.

In one embodiment, the nanoparticle is non-toxic, stable, and degradable in vivo releasing the siRNA. In one embodiment, the nanoparticle comprises a calcium phosphosilicate complex. The calcium phosphosilicate complex is stable and non-toxic.

In some embodiments, the nanoparticles, as exemplified in FIG. 1, are termed "nanojackets."

In one embodiment, the nanoparticle, (e.g., the lipid nanoparticle, the calcium phosphosilicate etc.) comprises particles that are between 80-250 nm in diameter.

In one embodiment, the siRNA of the invention may be associated with a cell targeting moiety. In one embodiment siRNAs may be designed wherein a 5'- or a 3' overhang region may be chemically crosslinked to a targeting moiety. In one embodiment, the siRNA is attached via a linker to a targeting moiety. In some embodiments, the linker is a non-reactive short linker, e.g. a short peptide linker. In one embodiment, the linker may be a bioactive peptide linker. In some embodiment, the linker is a short PEG molecule, comprising 10-12 carbon atoms in a chain. In some embodiments, the PEG molecule is crosslinked to the 5' end or the 3'-end of one strand of the siRNA. In one embodiment, the crosslinker is a maleimide functional bi-conjugational linker. In one embodiment, the crosslinker is a short polymer. In one embodiment, the polymer is a functional polymer, a conjugated polymer or a copolymer, for example, a PLGA-PEG, a PLA-PEG, a PCA-PEG, a lipid PEG, a polylysine PEG.

In some embodiments, the siRNA delivery system is a Solid Nucleic Acid Lipid Nanoparticle (SNALP) technology, which utilizes cationic or charge-conversional lipids with polyethylene glycol (PEG) surface groups.

In some embodiments, the siRNA delivery system is a cyclodextrin-based delivery system.

In some embodiments, the siRNA is conjugated directly or via a linker to an aptamer. Aptamers are synthetically tractable ligands for both diagnostic and therapeutic purposes, and are often referred to as nucleic acid ligands, "oligobodies," or "chemical antibodies." Aptamers that bind cell surface receptors are readily endocytosed. Aptamers are characterized by an ability to fold into complex tertiary structures and to bind with high affinity (low nM to high pM equilibrium dissociation constants) and specificity to their targets. Isolation of aptamers specific for a target of interest involves iterative rounds of a process termed SELEX (systematic evolution of ligands by exponential enrichment; (Tuerk and Gold, 1990, *Proc. Natl. Acad. Sci. USA.* 89, 6988-6992). For the SELEX process, an aptamer library is incubated with a protein target. The protein-bound aptamers are then specifically recovered. These sequences are amplified with PCR or RT-PCR. Single-stranded RNA or DNA sequences representing the recovered sequences are then generated from these PCR products, and used in the subsequent selection round. Exemplary aptamers known to one of skill in the art may include tenascin-C aptamer (TTA1), PMSA aptamer, CTLA-4 aptamer, HIV-bivalent aptamer etc., depending on the cancer type, target etc. (Thiel et al., Oligonucleotides. 2009 Sep. 1; 19 (3): 209-222).

Pharmaceutical Compositions

Provided herein is a pharmaceutical composition comprising a RIZ2 inhibitor. And a pharmaceutically acceptable ingredient. In some embodiments, the RIZ2 inhibitor comprises one or more polynucleotide molecules and a delivery system. In some embodiments, the RIZ2 inhibitor comprises an inhibitory RNA molecule, such as a double stranded siRNA molecule. In some embodiments, the inhibitory RNA molecule hybridizes to at least 10 contiguous nucleobases on the PRDM2 gene or a PRDM2 gene product. In some embodiments, the inhibitory RNA molecule is about 10 to about 21 nucleotides in length. In some embodiments, the RIZ2 inhibitor comprises more than one siRNA.

Provided herein is an siRNA formulated in a pharmaceutical composition for administering by subcutaneous injection.

Provided herein is an siRNA formulated in a pharmaceutical composition for administering by intravenous injection.

Provided herein is an siRNA formulated in a pharmaceutical composition for systemic administration.

Provided herein is an siRNA formulated in a pharmaceutical composition for administering locally or topically.

In one embodiment, the pharmaceutically acceptable excipient may be pathogen free water. In one embodiment, the pharmaceutically acceptable excipient may be a suitable buffer at neutral pH., e.g., phosphate buffered saline. In some embodiments, the pharmaceutically acceptable excipient may be a slightly acidic aqueous solution. In some embodiments, the pharmaceutically acceptable excipient may comprise glycol, glycerol, DMSO, soluble components, sugars, salts etc. In some embodiments, the formulation comprises a bulking agent, e.g. sucrose, trehalose, mannitol, glycine, lactose and/or raffinose, to impart a desired consistency to the formulation and/or stabilization of formulation components. In some embodiments, excipient commonly used for topical administration may be used, as is known to one of skill in the art.

Provided herein is a pharmaceutical composition comprising an inhibitory double-stranded RNA comprising a sequence of SEQ ID NO: 1, or a sequence having at least 90% identity to SEQ ID NO: 1. In some embodiments, provided herein is a pharmaceutical composition comprising an inhibitory double-stranded RNA comprising a sequence of SEQ ID NO: 10, or a sequence having at least 90% identity to SEQ ID NO: 10. Provided herein is a pharmaceutical composition comprising an inhibitory double-stranded RNA comprising the sequence of SEQ ID NO: 1 as sense strand and the sequence of SEQ ID NO: 10 as antisense strand.

Provided herein is a pharmaceutical composition comprising an inhibitory double-stranded RNA comprising a sequence of SEQ ID NO: 6, or a sequence having at least 90% identity to SEQ ID NO: 6. In some embodiments, provided herein is a pharmaceutical composition comprising an inhibitory double-stranded RNA comprising a sequence of SEQ ID NO: 11, or a sequence having at least 90% identity to SEQ ID NO: 11. Provided herein is a pharmaceutical composition comprising an inhibitory double-stranded RNA comprising the sequence of SEQ ID NO: 6 as sense strand and the sequence of SEQ ID NO: 11 as antisense strand.

Provided herein is a pharmaceutical composition comprising an inhibitory double-stranded RNA In one embodiment, provided herein is a RIZ2 inhibitor comprising a double stranded polynucleotide comprising a sense strand of SEQ ID NO: 2 or a sequence having at least 90% identity to SEQ ID NO: 2, and an anti sense strand of SEQ ID NO: 12, or a sequence having at least 90% identity to SEQ ID NO:12.

In one embodiment, provided herein is a pharmaceutical composition comprising a RIZ2 inhibitor comprising a double stranded polynucleotide comprising a sense strand of SEQ ID NO: 3, or a sequence having at least 90% identity to SEQ ID NO:3, and an antisense strand of SEQ ID NO: 13, or a sequence having at least 90% identity to SEQ ID NO:13.

In one embodiment, provided herein is a pharmaceutical composition comprising a RIZ2 inhibitor comprising a double stranded polynucleotide comprising a sense strand of SEQ ID NO: 4, or a sequence having at least 90% identity to SEQ ID NO:4, and an antisense strand of SEQ NO: 14, or a sequence having at least 90% identity to SEQ ID NO:14.

In one embodiment, provided herein is a pharmaceutical composition comprising a RIZ2 inhibitor comprising a double stranded polynucleotide comprising a sense strand of SEQ ID NO: 5, or a sequence having at least 90% identity to SEQ ID NO:5, and an antisense strand of SEQ ID NO: 15, or a sequence having at least 90% identity to SEQ ID NO:15.

In one embodiment, provided herein is a pharmaceutical composition comprising a RIZ2 inhibitor comprising a double stranded polynucleotide comprising a sense strand of SEQ ID NO: 7, or a sequence having at least 90% identity to SEQ ID NO:7, and an antisense strand of SEQ IO NO: 16, or a sequence having at least 90% identity to SEQ ID NO: 16.

In one embodiment, provided herein is a pharmaceutical composition comprising a RIZ2 inhibitor comprising a double stranded polynucleotide comprising a sense strand of SEQ ID NO: 8, or a sequence having at least 90% identity to SEQ ID NO:8, and an antisense strand of SEQ ID NO: 17 or a sequence having at least 90% identity to SEQ ID NO:17.

In one embodiment, provided herein is a pharmaceutical composition comprising a RIZ2 inhibitor comprising a double stranded polynucleotide comprising a sense strand of SEQ ID NO: 9, or a sequence having at least 90% identity to SEQ ID NO:9, and an antisense strand of SEQ ID NO: 18, or a sequence having at least 90% identity to SEQ ID NO:18.

In some embodiments, the pharmaceutical composition comprises one or more siRNAs described above, and a siRNA delivery system, such as a liposome, a nanoparticle, as disclosed herein. In some embodiments, the pharmaceutical composition having the delivery system comprises a cell targeting moiety, wherein the cell targeting moiety is a ligand, and antibody or an antibody fragment, a single chain antibody, a peptide or an aptamer. In some embodiments, the cell targeting moiety is a cell-penetrating peptide. In some embodiments, the delivery system comprises one or more of lipids, cyclodextrin, chitosan, carbohydrate polymers, elastin-like polymers (ELP), calcium phosphate polymers or combinations thereof.

Provided herein is a pharmaceutical composition comprising the RIZ2 inhibitor comprises comprising: (i) an siRNA comprising a double stranded RNA of 10-21 nucleotides that have homology to human PRDM2/RIZ2 gene; covalently linked to a (ii) a PEG molecule, linked to a (iii) cell targeting moiety; wherein the cell targeting moiety is an aptamer.

In one embodiment, the pharmaceutical composition comprises one or more chemotherapeutic drugs. Exemplary chemotherapeutic drugs may include but are not limited to: obinutuzumab, bendamustine, chlorambucil, cyclophosphamide, ibrutinib, methotrexate, cytarabine, dexamethasone, cisplatin, bortezomib, fludarabine, idelalisib, acalabrutinib, lenalidomide, venetoclax, cyclophosphamide, ifosfamide, etoposide, pentostatin, melphalan, carfilzomib, ixazomib, panobinostat, daratumumab, elotuzumab, thalidomide, lenalidomide, or pomalidomide, or a combination thereof.

In one embodiment, the therapeutic composition may comprise additional drugs, for example, checkpoint inhibitors, e.g., a PD1 inhibitor, a PDL1 inhibitor, or a CTLA4 inhibitor or a combination thereof.

Therapeutic and Diagnostic Methods

Therapeutic compositions described above comprising one or more inhibitory RNA molecules targeting RIZ2 may be used to treat cell proliferative disorders in a subject. In some embodiments, the subject is a human. In one embodiment, the cell proliferative disorder is a cancer. In one embodiment, the cell proliferative disorder is associated with or a result of cell cycle deregulation, loss of cell cycle checkpoint inhibition, and/or RIZ1/RIZ2 imbalance. It has been well known that histone H3 K9 methyltransferase activity of RIZ1 plays a significant role in negative regulation of cell proliferation, and RIZ1 expression is reduced in various cancers. RIZ2 was found to be upregulated in cancer cells, but its biological activity was not clear. It was mainly believed to be a non-functional counterpart of RIZ1, and it was hypothesized that RIZ2, acting as a negative regulator of RIZ1 function, mediates the proliferative effect of estrogen through regulation of survival and differentiation gene expression. J Cell Physiol 2012 March; 227 (3):964-75. Additionally, RIZ2 being an N-terminal-truncated shorter transcript and translated product compared to RIZ1, the former presented less opportunity for manipulation independent of RIZ1.

The instant disclosure provide a method for targeting RIZ2, and compositions that inhibit RIZ2 independent of RIZ1.

Provided herein are therapeutic methods and compositions to specifically target and manipulate RIZ2. In one embodiment, the therapeutic composition comprises a pharmaceutical composition comprising a RIZ2-specific siRNA, for the treatment of a cell proliferative disorder. In one embodiment, the cell proliferative disorder is cancer.

Provided herein is a method of treating cancer, comprising administering to a subject in need thereof a pharmaceutical composition described in any of the sections above. As a result of the disclosed study, it is now understood that the RIZ2 provides a highly promising therapeutic target and not only can RIZ2 be selectively downregulated in cancer cells, RIZ1 can be upregulated by inhibiting RIZ2. It is also understood that RIZ/RIZ2 imbalance, e.g., downregulation of RIZ1 and upregulation of RIZ2 is a significantly upstream nodal regulation of the cell cycle, that is common in many cancers, and therefore the therapy is applicable to a wide variety of cancers. For instance, In one embodiment, the method and compositions described herein are therapeutically applicable to solid cancers. In one embodiment, the method and compositions described herein are therapeutically applicable to liquid cancers. In one embodiment, the cancer is a cancer of breast, colon, endometrial, esophageal, gastric, glioma, kidney, liver, lung, lymphoma, melanoma, meningioma, myeloma, nasopharyngeal, neuroblastoma, ovarian, pancreatic, parathyroid, pituitary, prostate, thyroid, or uterine tissue.

In one embodiment, the cancer is a solid tumor. In one embodiment, the cancer is a lung cancer. It is contemplated that any cancer may be treated using the methods and compositions described herein. Examples of cancer include, but are not limited to, carcinoma, lymphoma, blastoma, sarcoma, and leukemia or lymphoid malignancies. More particular examples of such cancers are noted below and include: squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial cancer or uterine carcinoma, salivary gland carcinoma, kidney or renal cancer, prostate cancer, vulval cancer, thyroid cancer, hepatic carcinoma, anal carcinoma, penile carcinoma, as well as head and neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor).

In other embodiments, the RIZ2 inhibitor, as described above and herein, is used to treat a hyperproliferative disorder, e.g., a hyperplasia, a cancer or hyperproliferative connective tissue disorder (e.g., a hyperproliferative fibrotic disease). In one embodiment, the hyperproliferative fibrotic disease is multisystemic or organ-specific. Exemplary hyperproliferative fibrotic diseases include, but are not limited to, multisystemic (e.g., systemic sclerosis, multifocal fibrosclerosis, sclerodermatous graft-versus-host disease in bone marrow transplant recipients, nephrogenic systemic fibrosis, scleroderma), and organ-specific disorders (e.g., fibrosis of the eye, lung, liver, heart, kidney, pancreas, skin and other organs). In other embodiments, the disorder is chosen from liver cirrhosis or tuberculosis. In other embodiments, the disorder is leprosy.

In one embodiment, the RIZ2 inhibitor is specifically designed to target and treat lung cancer. In some embodiments, the RIZ2 inhibitor is formulated for aerosol delivery into the lung. In some embodiments, the RIZ2 inhibitor is formulated for systemic delivery via intravenous injection.

In one embodiments, the RIZ2 inhibitor comprising the ARIZ-047 siRNA is designed for treating lung cancer.

In one embodiment, ARIZ-047 exhibit no toxic effect on living cell, or experimental animals.

In some embodiments, the therapeutic composition comprising the RIZ2 inhibitor may be co-administered with a chemotherapeutic agent. The chemotherapeutic can be cyclophosphamide, doxorubicin, vincristine, prednisone, or rituximab, or a combination thereof. Other chemotherapeutics include obinutuzumab, bendamustine, chlorambucil, cyclophosphamide, ibrutinib, methotrexate, cytarabine, dexamethasone, cisplatin, bortezomib, fludarabine, idelalisib, acalabrutinib, lenalidomide, venetoclax, cyclophosphamide, ifosfamide, etoposide, pentostatin, melphalan, carfilzomib, ixazomib, panobinostat, daratumumab, elotuzumab, thalidomide, lenalidomide, or pomalidomide, or a combination thereof. "Co-administered" refers to administering two or more therapeutic agents or pharmaceutical compositions during a course of treatment. Such co-administration can be simultaneous administration or sequential administration. Sequential administration of a later-administered therapeutic agent or pharmaceutical composition can occur at any time during the course of treatment using the RIZ2 inhibitor.

In one embodiment, the RIZ2 inhibitor siRNA may be co-administered with cisplatin.

In one embodiment, use of an siRNA described here (e.g., ARIZ-047), with a drug as described above may provide advantage in that a lower concentration or dose of the drug can be sufficient for achieving the therapeutic effect, thereby reducing the drug related toxic effects in the subject with cancer.

Administration of the pharmaceutical compositions contemplated herein may be carried out using conventional techniques including, but not limited to, infusion, transfusion, or parenterally. In some embodiments, parenteral administration includes infusing or injecting intravascularly, intravenously, intramuscularly, intraarterially, intrathecally, intratumorally, intradermally, intraperitoneally, transtracheally, subcutaneously, subcuticularly, intraarticularly, subcapsularly, subarachnoidly and intrasternally.

In one embodiment, the pharmaceutical composition comprising RIZ2 inhibitor may be administered once every day, once every 2 days, or 3 days, or 4 days or 5 days or 6 days or 7 days or 8 days or 9 days or 10 days or 11 days or 12 days or 13 days or 14 days. In one embodiment, the pharmaceutical composition comprising RIZ2 inhibitor may be administered once every 15 days. In one embodiment, the pharmaceutical composition comprising RIZ2 inhibitor may be administered once every 20 days. In one embodiment, the pharmaceutical composition comprising RIZ2 inhibitor may be administered once every month. In one embodiment, the pharmaceutical composition comprising RIZ2 inhibitor may be administered once every 2 months, or 3 months, or 4 months, or 5 months or 6 months.

In one aspect, provided herein is a method of patient selection that selecting a patient as a subject in need for administering a composition comprising a RIZ2 inhibitor, the method comprising: (i) detecting an elevated RIZ1 methylation level in a biological sample of the subject compared to a control sample or control value; or, (ii) detecting a downregulation of RIZ1 mRNA levels compared to a control sample or control value; wherein an at least 1.1-fold elevation of methylated RIZ1, or, at least 2-fold downregulation of RIZ1 mRNA levels in the biological sample of the subject compared to the control sample or value determines the subject to be in need for administering the composition comprising a RIZ2 inhibitor, and wherein the control sample is a sample from a clinically healthy individual, a control value is an average value of RIZ1 methylation levels from two or more clinically healthy individual samples.

In some embodiments, the RIZ2 inhibitor reduces hypermethylation of RIZ1 gene.

Kits

The invention also provides kits comprising a RIZ2 inhibitor. Some aspects of this disclosure provide kits for the treatment of cancer, or a hyperproliferative disorder. In one embodiment, the kit is a neoplasia treatment kit.

In one embodiment, the kit may comprise a therapeutic composition comprising a RIZ2 inhibitor as described in the disclosure, in a properly labeled bottle with indicated concentration and directions for use, preserved in a temperature and environmental conditions that ensure safety, and efficacy of the therapeutic active ingredient.

In one embodiment, the kit may comprise a detector set for detecting RIZ1 and RIZ2 mRNA in a biological sample. The detector set may comprise a set of primers, e.g., a set of forward primers, and reverse primers for detecting RIZ1 levels, and a set of forward primers, and reverse primers for detecting RIZ2 levels. In some embodiments, RIZ 1 level is measured in sputum samples, and serve as biomarker for neoplasia. In one embodiment, the kit comprises one or more components for detecting RIZ1 levels and RIZ2 levels (e.g., mRNA, protein etc) in a biological sample from a human. In some embodiments the kit may comprises a diagnosis unit for detecting RIZ1 methylation. In one embodiment, RIZ1 methylation can be detected using methylation based sequencing. In one embodiment, RIZ1 methylation may be detected by using one or more methylation based primers. The kit may comprise one or more vials comprising a primer, a reagent, an enzyme, a buffer etc. Each vial is labeled with component, concentration. The kit comprises at least one written instruction sheet for use of the kit.

The neoplasia treatment kit comprises written instructions for using the modified immune cells in the treatment of the neoplasia.

The detection kit comprises written instructions on the components included, safety parameters and directions for use.

In some embodiments, a single kit may comprise components of a therapeutic kit and a detection kit.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

Embodiments

1. A method of inhibiting cell proliferation, comprising contacting a population of cells with a composition comprising a Retinoblastoma Protein-Interacting Zinc Finger Protein 2 (RIZ2) inhibitor.

2. The method of embodiment [0191], wherein the RIZ2 inhibitor reduces expression of RIZ2 in the cells.

3. The method of embodiment [0191] or 1, wherein the RIZ2 inhibitor reduces expression of RIZ2 mRNA in the cells.

4. The method of embodiment 3, wherein the RIZ2 mRNA is reduced by at least 10% when compared to expression of a housekeeping gene in the cells.

5. The method of embodiment 3 or 4, wherein the RIZ2 mRNA is reduced by at least 10% relative to a control cell population.

6. The method of embodiment 5, wherein the control cell population is a cell population that has not been contacted with the composition comprising the RIZ2 inhibitor.

7. The method of embodiment 5, wherein expression of RIZ2 mRNA is reduced by at least 50% relative to the control cell population.

8. The method of embodiment 5, wherein expression of RIZ2 mRNA is reduced by at least 80% relative to the control cell population.

9. The method of any one of the embodiments [0191]-8, wherein the RIZ2 inhibitor further increases expression of RIZ1 in the cell population.

10. The method of embodiment 9, wherein the composition alters a ratio of RIZ1 mRNA expression level to RIZ2 mRNA expression level.

11. The method of embodiment 9, wherein the composition alters the ratio of RIZ1 protein expression level to RIZ2 protein expression level.

12. The method of embodiment 9 or 10, wherein the RIZ2 inhibitor alters the ratio of RIZ1 to RIZ2 mRNA expression levels by greater than at least 1.1-fold.

13. The method of embodiment 9 or 10, wherein the RIZ2 inhibitor alters the ratio of RIZ1 to RIZ2 mRNA expression levels by greater than at least 1.5-fold.

14. The method of embodiment 9 or 10, wherein the RIZ2 inhibitor alters the ratio of RIZ1 to RIZ2 mRNA expression levels by at least 2-fold.

15. The method of any one of the embodiments [0191]-8, wherein the RIZ2 inhibitor further decreases hypermethylation of RIZ1.

16. The method of embodiment 1, wherein the cells are mammalian cells.

17. The method of embodiment 1, wherein the cells are human cells.

18. The method of embodiment 1, wherein the cells are cancer cells.

19. The method of embodiment 1, wherein the cells are from a tissue that is a breast, colon, endometrial, esophageal, gastric, glioma, kidney, liver, lung, lymphoma, melanoma, meningioma, myeloma, nasopharyngeal, neuroblastoma, ovarian, pancreatic, parathyroid, pituitary, prostate, thyroid, or a uterine tissue.

20. The method of embodiment 18, wherein the cancer cells are from a blood cancer.

21. The method of embodiment 8, wherein the cancer cells are from a solid tumor.

22. The method of embodiment 1, wherein the contacting comprises contacting a population of cells with the composition comprising the RIZ2 inhibitor.
23. The method of embodiment 22, wherein the contacting results in a reduction of a cell number of the population of cells by at least 10%.
24. The method of embodiment 22, wherein the contacting results in a reduction of a cell number of the population of cells by about 90%.
25. The method of embodiment 1 or 22, wherein inhibiting cell proliferation comprises reducing a cell mass by at least 10%.
26. The method of embodiment 25, wherein inhibiting cell proliferation comprises reducing a cell mass by about 50%.
27. The method of embodiment [0191], wherein contacting the cell further comprises incorporating the RIZ2 inhibitor into the cell.
28. The method of embodiment 1, wherein the RIZ2 inhibitor comprises a non-naturally occurring compound.
29. The method of embodiment 28, wherein the RIZ2 inhibitor is a synthetic agent.
30. The method of embodiment 29, wherein the RIZ2 inhibitor comprises a peptide.
31. The method of embodiment 29, wherein the RIZ2 inhibitor comprises a conjugated polypeptide.
32. The method of embodiment 29, wherein the RIZ2 inhibitor comprises one or more polynucleotides.
33. The method of embodiment 32, wherein RIZ2 inhibitor comprises a synthetic polynucleotide.
34. The method of embodiment 33, wherein the one or more polynucleotides comprise one or more modified nucleotides.
35. The method of embodiment [0191], wherein the composition comprising the RIZ2 inhibitor comprises one or more polynucleotides coupled to a delivery system.
36. The method of embodiment 35, wherein the delivery system comprises one or more of lipids, cyclodextrin, chitosan, carbohydrate polymers, elastin-like polymers (ELP), calcium phosphate polymers or combinations thereof.
37. The method of embodiment 35, wherein the delivery system comprises a lipid.
38. The method of embodiment 35, wherein the delivery system comprises a PEGylated lipid.
39. The method of embodiment 35, wherein the delivery system comprises a cell targeting moiety.
40. The method of embodiment 39, wherein the cell targeting moiety, is cell-type specific.
41. The method of embodiment 39, wherein the cell targeting moiety is a ligand that selectively binds to a receptor on a target cell.
42. The method of embodiment 39, wherein the cell targeting moiety is an antibody that binds to a cell surface molecule on a target cell.
43. The method of embodiment 42, wherein the cell targeting moiety is a single chain antibody or an antibody fragment.
44. The method of embodiment 39, wherein the cell targeting moiety is a peptide.
45. The method of embodiment 44, wherein the cell targeting moiety is a cell-penetrating peptide.
46. The method of embodiment 44 or 45, wherein the cell targeting moiety is cyclic peptide.
47. The method of embodiment 39, wherein the cell targeting moiety is an aptamer.
48. The method of embodiment 35, wherein the delivery system comprises a liposome.
49. The method of embodiment 35, wherein the delivery system comprises a nanoparticle.
50. The method of any one of the embodiments [0191]-49, wherein the RIZ2 inhibitor comprises an RNA molecule.
51. The method of embodiment 50, wherein the RIZ2 inhibitor comprises an inhibitory RNA molecule.
52. The method of embodiment 51, wherein the inhibitory RNA molecule hybridizes to at least 10 contiguous nucleobases on the PRDM2 gene or a PRDM2 gene product.
53. The method of embodiment 50, wherein the inhibitory RNA is about 10 to about 21 nucleotides in length.
54. The method of embodiment 50, wherein the inhibitory RNA molecule is double-stranded.
55. The method of embodiment 50, wherein the RNA molecule comprises one or more modified nucleotides.
56. The method of any one of the embodiments [0191]-55, wherein the RIZ2 inhibitor comprises an inhibitory double-stranded RNA comprising a sense strand having a sequence of SEQ ID NO: 1, and an antisense strand having a sequence of SEQ ID NO: 10.
57. The method of any one of the embodiments [0191]-55, wherein the RIZ2 inhibitor comprises an inhibitory double-stranded RNA comprising a sense strand having a sequence of SEQ ID NO: 6; and an antisense strand having a sequence of SEQ ID NO: 11.
58. The method of any one of the embodiments [0191]-55, wherein the RIZ2 inhibitor comprises an inhibitory double-stranded RNA molecule comprising a sense strand and an antisense strand selected from Table 2.
59. A method of treating a cell proliferative disease or a disorder in a subject, comprising administering to the subject a composition comprising a RIZ2 inhibitor.
60. A method of selecting a patient as a subject in need for administering a composition comprising a RIZ2 inhibitor, the method comprising:
(i) detecting an elevated RIZ1 methylation level in a biological sample of the subject compared to a control sample or control value; or,
(ii) detecting a downregulation of RIZ1 mRNA levels compared to a control sample or control value;
wherein an at least 1.1-fold elevation of methylated RIZ1, or, at least 2-fold downregulation of RIZ1 mRNA levels in the biological sample of the subject compared to the control sample or value determines the subject to be in need for administering the composition comprising a RIZ2 inhibitor, and
wherein the control sample is a sample from a clinically healthy individual, a control value is an average value of RIZ1 methylation levels from two or more clinically healthy individual samples.
61. The method of embodiment 59, wherein the cell proliferative disease or disorder is a cancer.
62. The method of embodiment 61, wherein the cancer is a cancer of breast, colon, endometrial, esophageal, gastric, glioma, kidney, liver, lung, lymphoma, melanoma, meningioma, myeloma, nasopharyngeal, neuroblastoma, ovarian, pancreatic, parathyroid, pituitary, prostate, thyroid, or uterine tissue.
63. The method of embodiment 61, wherein the cancer is a solid tumor.
64. The method of embodiment 62, wherein the cancer is a lung cancer.
65. The method of embodiment 59, wherein administering comprises administering an effective amount of the RIZ2 inhibitor.
66. The method of embodiment 65, wherein the effective amount of the RIZ2 inhibitor is an amount that reduces at least one or more disease parameters associated with the cell proliferative disorder.

67. The method of embodiment 66, wherein the cell proliferative disease is a cancer and the effective amount of the RIZ2 reduces the number of cancer cells.

68. The method of embodiment 66, wherein the cell proliferative disease is a solid tumor and the effective amount of the RIZ2 reduces the tumor mass.

69. The method of embodiment 59 or 60, wherein the composition comprising the RIZ2 inhibitor comprises one or more polynucleotides coupled to a delivery system.

70. The method of embodiment 69, wherein the one or more polynucleotides comprise an inhibitory RNA molecule.

71. The method of embodiment 70, wherein the inhibitory RNA molecule is a double-stranded RNA molecule comprising a sense strand having a sequence of SEQ ID NO: 1, and an antisense strand having a sequence of SEQ ID NO: 10.

72. The method of embodiment 70, wherein the inhibitory RNA molecule is a double-stranded RNA molecule comprising a sense strand having a sequence of SEQ ID NO: 6, and an antisense strand having a sequence of SEQ ID NO: 11.

73. The method of embodiment 1, wherein the composition further comprises a delivery system.

74. The method of any one of the embodiments 74, wherein the delivery system comprises a lipid and/or a cell targeting moiety.

75. The method of embodiment 75, wherein the lipid is a PEGylated lipid.

76. The method of embodiment 75, wherein the cell targeting moiety is a cell-penetrating peptide, a cyclic peptide, an antibody or a fragment thereof, or an aptamer.

77. A pharmaceutical composition comprising: (a) the RIZ2 inhibitor; and (b) a pharmaceutically acceptable excipient.

78. The pharmaceutical composition of the preceding embodiments, wherein the RIZ2 inhibitor comprises one or more polynucleotide molecules and a delivery system.

79. The pharmaceutical composition of embodiment 78, wherein the RIZ2 inhibitor comprises an inhibitory RNA molecule.

80. The pharmaceutical composition of embodiment 77, wherein the inhibitory RNA molecule hybridizes to at least 10 contiguous nucleobases on the PRDM2 gene or a PRDM2 gene product.

81. The pharmaceutical composition of embodiment 77, wherein the inhibitory RNA molecule is about 10 to about 21 nucleotides in length.

82. The pharmaceutical composition of embodiment 77, wherein the inhibitory RNA molecule is double-stranded.

83. The pharmaceutical composition of embodiment 77, wherein the inhibitory double-stranded RNA comprising a sense strand having a sequence of SEQ ID NO: 1, and an antisense strand having a sequence of SEQ ID NO: 10.

84. The pharmaceutical composition of embodiment 77, wherein the inhibitory double-stranded RNA comprising a sense strand and an antisense strand selected from Table 2.

85. The pharmaceutical composition of embodiment 77, wherein the inhibitory double-stranded RNA comprising a sense strand having a sequence of SEQ ID NO: 6, and an antisense strand having a sequence of SEQ ID NO: 11.

86. The pharmaceutical composition of embodiment 78, wherein the delivery system comprises a cell targeting moiety.

87. The pharmaceutical composition of embodiment 86, wherein the cell targeting moiety is a ligand, and antibody or an antibody fragment, a single chain antibody, a peptide or an aptamer.

88. The pharmaceutical composition of embodiment 86, wherein cell-penetrating peptide.

89. The pharmaceutical composition of embodiment 86, wherein the delivery system comprises one or more of lipids, cyclodextrin, chitosan, carbohydrate polymers, elastin-like polymers (ELP), calcium phosphate polymers or combinations thereof.

90. The pharmaceutical composition of embodiment 78, wherein the RIZ2 inhibitor comprises:
(i) an siRNA comprising a double stranded RNA of 10-21 nucleotides that have homology to human PRDM2/RIZ2 gene; covalently linked to a
(ii) a PEG molecule, linked to a
(iii) cell targeting moiety;
wherein the cell targeting moiety is an aptamer.

91. The pharmaceutical composition of embodiment 78, wherein the delivery system comprises a liposome.

92. The pharmaceutical composition of embodiment 78, wherein the delivery system comprises a nanoparticle.

93. The pharmaceutical composition of embodiment 92, wherein the nanoparticle comprise lipids, cyclodextrin, chitosan, carbohydrate polymers, elastin-like polymers (ELP), calcium phosphate polymers, and combinations thereof.

94. The pharmaceutical composition of embodiment 92, wherein the nanoparticle comprising a calcium phosphosilicate complex.

95. The pharmaceutical composition of embodiment 90, further comprising a calcium phosphosilicate complex associated with the RIZ2 inhibitor.

96. The pharmaceutical composition of embodiment 77, further comprising one or more chemotherapeutic drugs.

INCORPORATION BY REFERENCE

All publications and patents mentioned herein are hereby incorporated by reference in their entirety as if each individual publication or patent was specifically and individually indicated to be incorporated by reference.

EXAMPLES

Example 1: Effect of RIZ2 siRNA

The following examples are put forth so as to provide those of ordinary skill in the art with a complete disclosure and description of how to make and use the assay, screening, and therapeutic methods of the invention, and are not intended to limit the scope of what the inventors regard as their invention.

An exemplary demonstration of the siRNAs designs described herein for effective cytotoxicity to human lung cancer cells using A549 cell line is described below.

Methods: A549 cells were plated in a 96 well plate (1,000 cells/well) and after 24 hours were transfected with 100 nM siRNA, using 0.2 µl DharmaFECT 1 (Dharmacon, Inc.), according to manufacturer's directions. Media was changed after two days, and after four days, percent cell viability was determined, relative to untreated cells using MTS cell viability assay. RIZ1 and RIZ2 mRNA levels were determined in control and siRNA-transfected cells using qPCR. RNA was extracted from cells 48 hours after transfection, and mRNA expression levels were detected using PRDM isoform A and PRDM isoform C specific PCR primers. RIZ mRNA expression levels were determined relative to GAPDH mRNA expression levels. Scrambled siRNA was used a negative control, and Tox (Transfection control siRNA, commercially available) was used a positive control.

Figure 2:
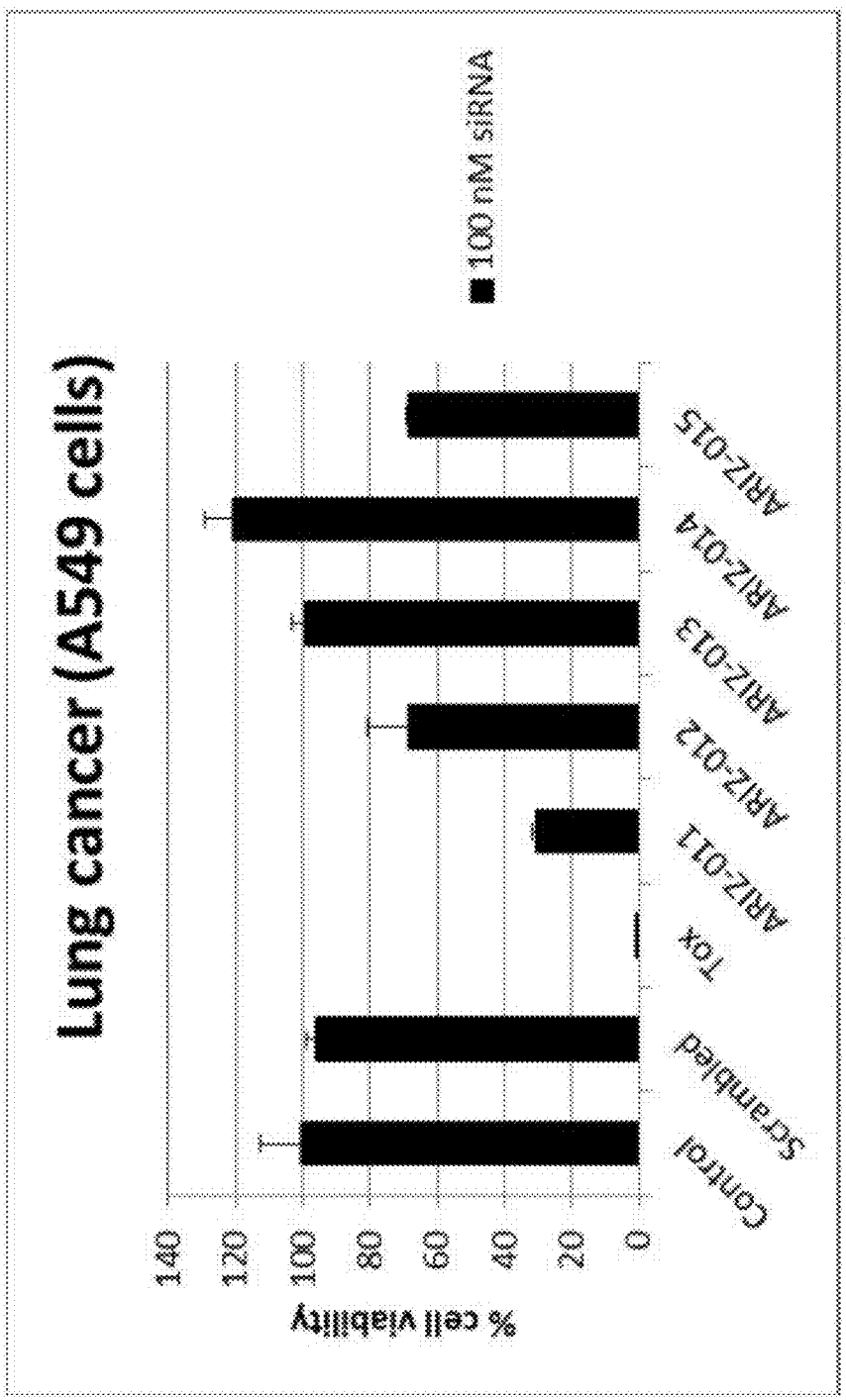
FIG. 2 depicts viability of human lung cancer cells (cell line A549) after exposure to siRNAs directed against PRDM2.

Results and discussion: As shown in FIG. 2, the resulting cell viability of A549 lung cancer cells following exposure to the various siRNAs, including ARIZ-011, ARIZ-012, ARIZ-013, ARIZ-014, and ARIZ-015, according to the method described in Example 1, above. Viability of the A549 lung cancer cells was decreased via the application of ARIZ-011, ARIZ-012, and ARIZ-015. However, ARIZ-011 showed highly encouraging results.

Figure 3:
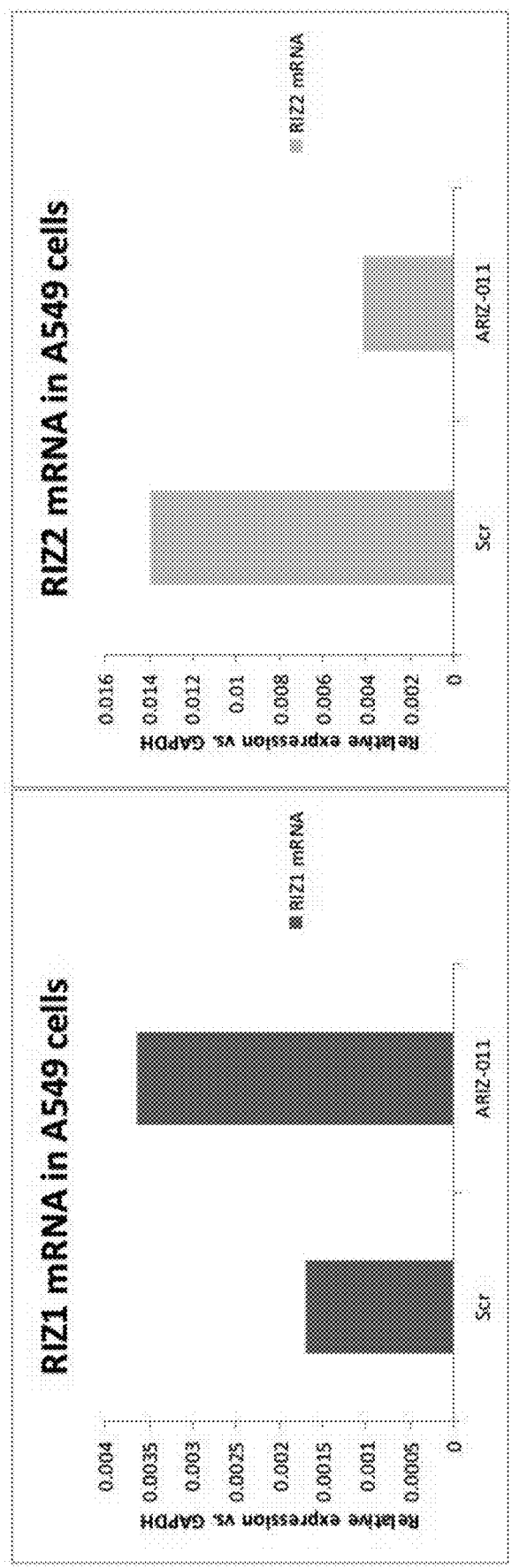
FIG. 3 depicts RIZ1 and RIZ2 mRNA levels in A549 lung cancer cells following exposure to ARIZ-011.

The relative levels of RIZ1 and RIZ2 mRNA in A549 cells after treatment with siRNA ARIZ-011 was tested, and as shown in FIG. 3, ARIZ-011 not only showed nearly a 75% decrease in RIZ2 mRNA, it also showed a simultaneous increase in RIZ1 mRNA. This was a surprising and unexpected result that relates to not only a decrease in RIZ2 mRNA, but restoration of the RIZ1/RIZ2 ratio imbalance in the cancerous cell line.

Summarizing the results, it is demonstrated that PRDM2 siRNAs were effective in killing A549 lung cancer cells. siRNA ARIZ-011 was the most effective siRNA tested, reducing relative cell viability to 30% after a single exposure to the siRNA.

siRNA ARIZ-015, an siRNA specific to RIZ2, which encompasses 10 nucleotides unique to the 3' end of the RIZ2 mRNA, was less effective at killing A549 cells (70% cell viability) than ARIZ-011 that is complementary to both RIZ1 and RIZ2 mRNA (30% cell viability).

The RIZ mRNA assay results shown in FIG. 3 was surprising and unexpected in that knockdown of the apparent oncoprotein RIZ2 by siRNA ARIZ-011 coincides with upregulated expression of the tumor suppressor protein RIZ1.

Example 2: Effect of Co-Administering RIZ2 siRNA and Chemotherapeutic Agent

This is an exemplary demonstration that coadministration of PRDM siRNA with a cychemotherapeutic agent (5-fluorouracil) potentiates human colon cancer cell killing while having a minimal effect on healthy cells.

Methods: Cells (cell line HCT116), were plated in a 96 well plate (1,000 cells/well) and after 24 hours were transfected with siRNA ARIZ-011 at 100 nM, using 0.2 μl DharmaFECT 1 (Dharmacon, Inc.), according to manufacturer's directions. Where indicated, 5-fluorouracil (25 μM) was added one day after transfection. Media (with 5-flurouracil where indicated) was changed after two days, and after four days, percent cell viability was determined, relative to untreated cells.

Figure 4:
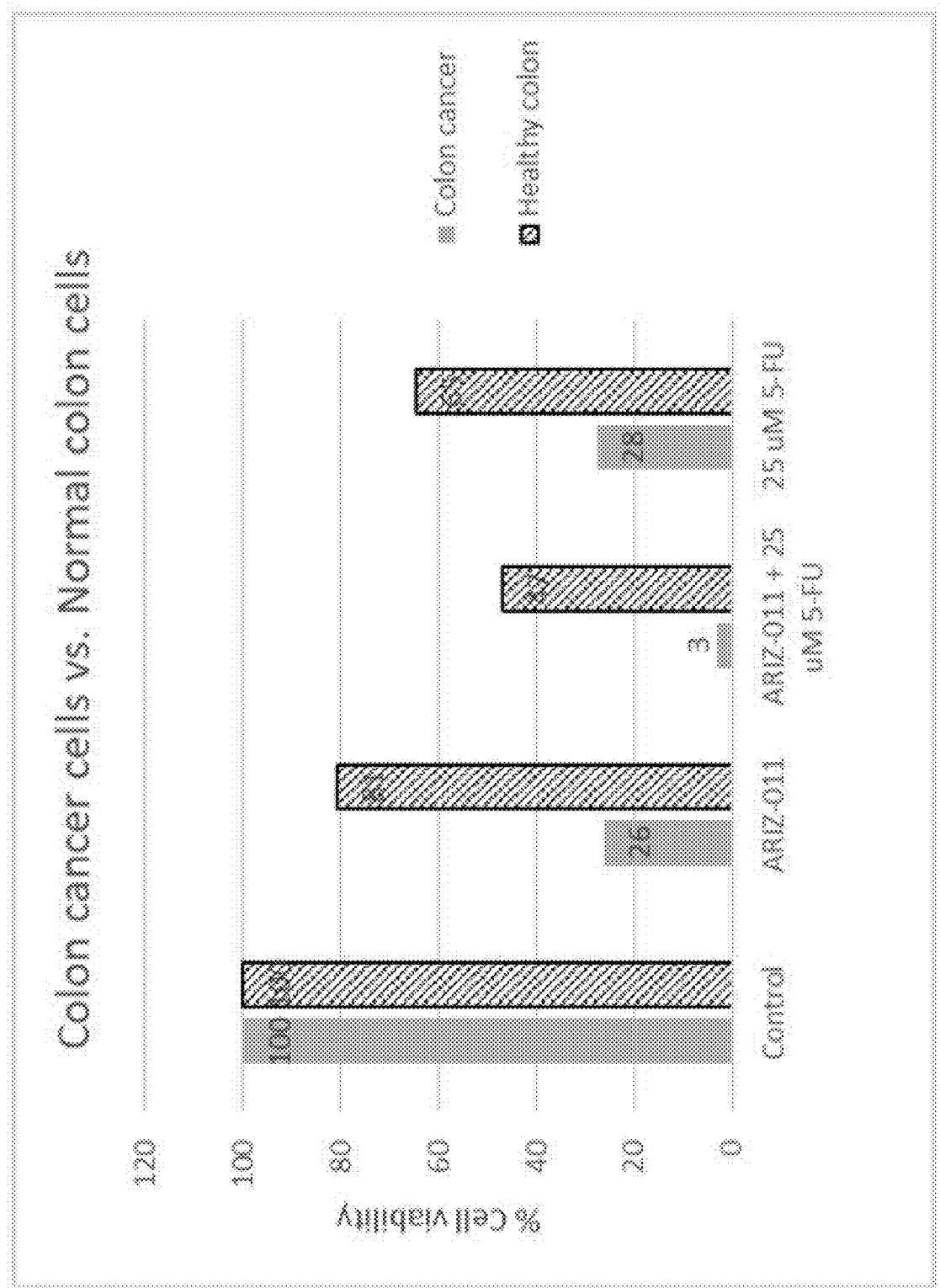
FIG. 4 depicts viability of human colon cancer cells (cell line HCT116) and normal colon cells (cell line CCD112) after exposure to ARIZ-011.
Figure 5:
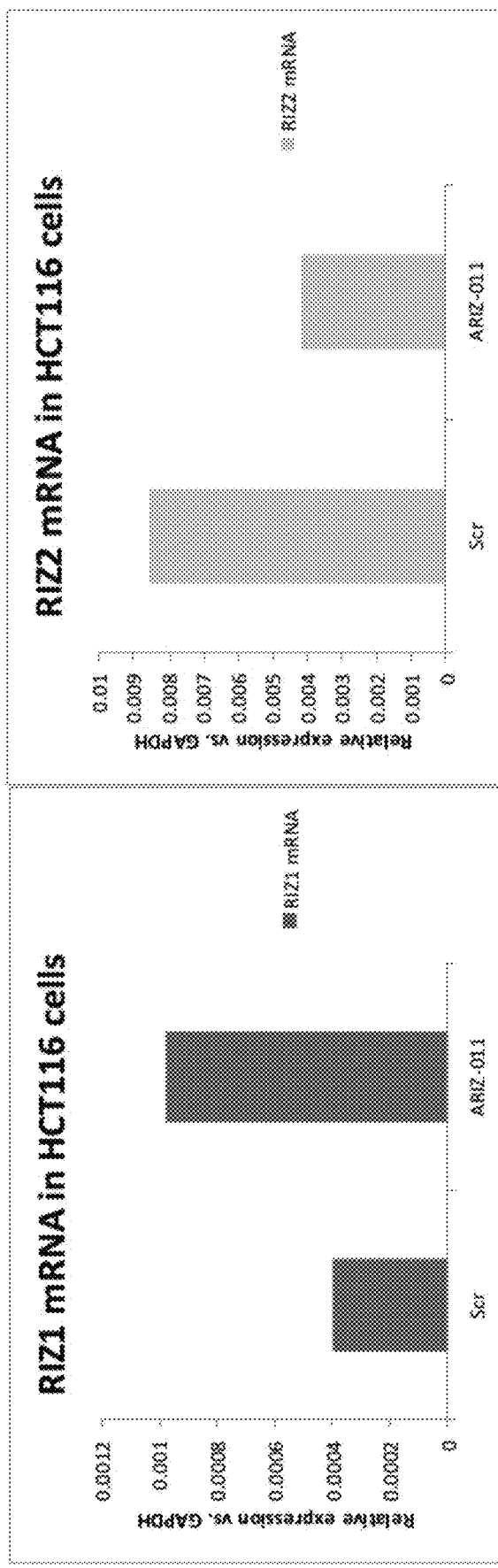
FIG. 5 depicts RIZ1 and RIZ2 mRNA levels in HCT116 cancer cells following exposure to ARIZ-011.

Results and Discussion: As illustrated in FIG. 4, coadministration of ARIZ-011 siRNA and 5FU led to decreased cell viability of HCT116 colon cancer cells by 97%, compared to about 72-74% in response to single administration of either the siRNA, or 5FU. Similar to the reported observation in Example 1, the RIZ2 siRNA selectively decreased the expression level of RIZ2, but a concurrent increase in RIZ1 mRNA was observed in the HCT116 cells (FIG. 5).

While siRNA ARIZ-011 alone was effective at killing HCT116 colon cancer cells (74% killing at a 100 nM dose), at par with the chemotherapeutic agent, 5-fluorouracil (5-FU) at 25 concentration (72%), these results showed that the siRNA was able to further increase the effectiveness of the chemotherapeutic agent. RIZ2 siRNA led to the rise in mRNA for the tumor suppressor RIZ1, which is known to kill cancer cells due to cell cycle arrest.

Example 3: siRNA Modifications

An exemplary modification of nucleobases in the designed siRNAs is demonstrated and tested as follows.

Taking the siRNA ARIZ-011, a modified siRNA is designed, as shown and designated ARIZ -047 (Table 1), row 6. In essence, a 5'-disulfide moiety is incorporated, and one uridine is replaced with 2'-methoxyuridine in the siRNA backbone, sense strand. The non-sense strand modifications are also shown in the right hand column of row 6.

Figure 6:
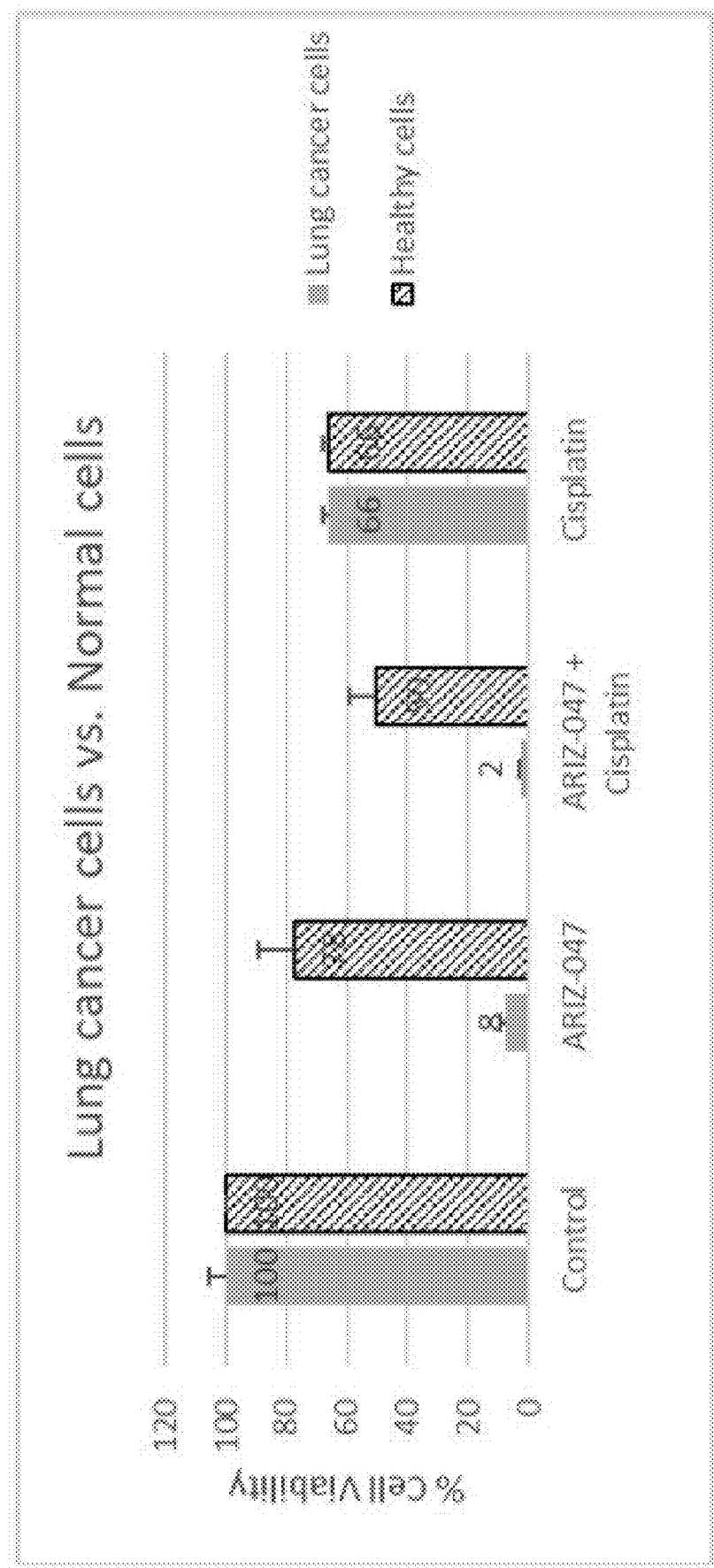
FIG. 6 depicts viability of human lung cancer cells (cell line A549) and normal epithelial cells (cell line CCD112) after exposure to ARIZ-047 (with or without cisplatin).

As shown in FIG. 6, siRNA ARIZ-047 alone (without cisplatin) was highly effective at killing A549 lung cancer cells (92% cell killing), with only limited harm to healthy cells (CCD-112 normal colon fibroblasts). These results show that modified siRNA (ARIZ-047) is highly effective in killing cancer cells at a 20 nM dose, a five-fold lower dose than the unmodified ARIZ-011, while demonstrating a minimal effect against normal cells. In addition, ARIZ-047 in combination with cisplatin was significantly more effective (98% cell killing) than ARIZ-047 alone, but resulted in substantially greater harm to healthy cells (50% killing) than ARIZ-047 alone.

Figure 7:
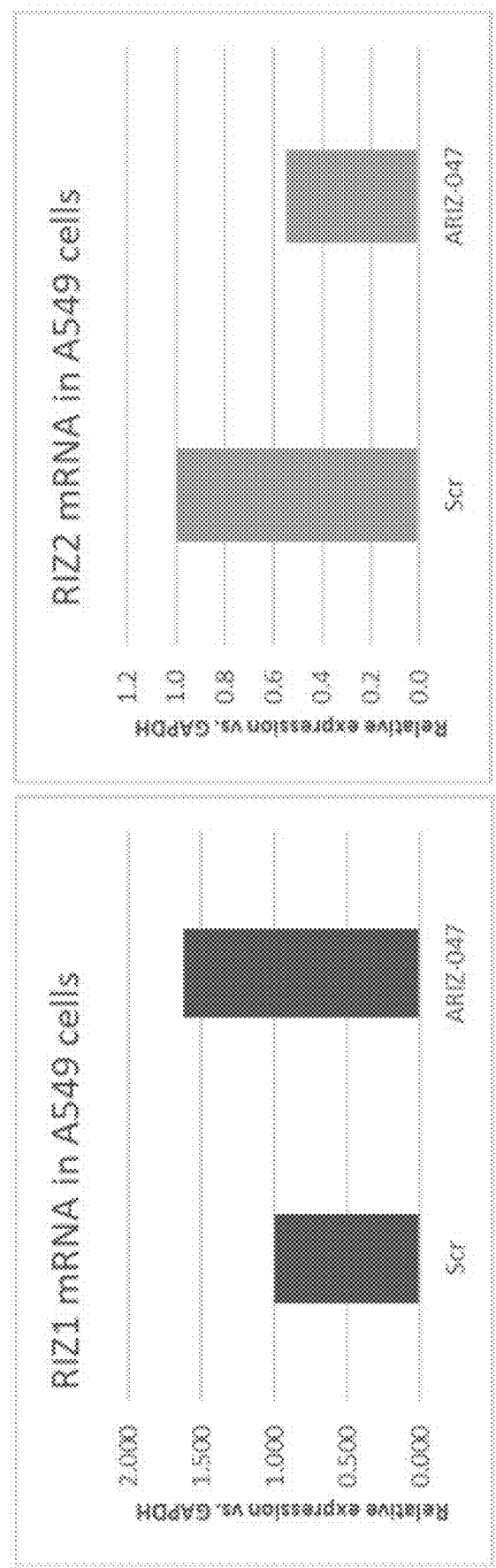
FIG. 7 depicts RIZ1 and RIZ2 mRNA levels in A549 lung cancer cells after exposure to ARIZ-047.

Similar to earlier data for lung and colon cancer, the RIZ mRNA assay results shown in FIG. 7 for lung cancer cells show an increase in RIZ1 mRNA and a decrease in RIZ2 mRNA. Again, these results indicating an effect on RIZ1 levels further suggest that RIZ2 upregulation reduces the expression of RIZ1.

Example 4: Effect of siRNA on Multiple Myeloma Cells

Figure 8:
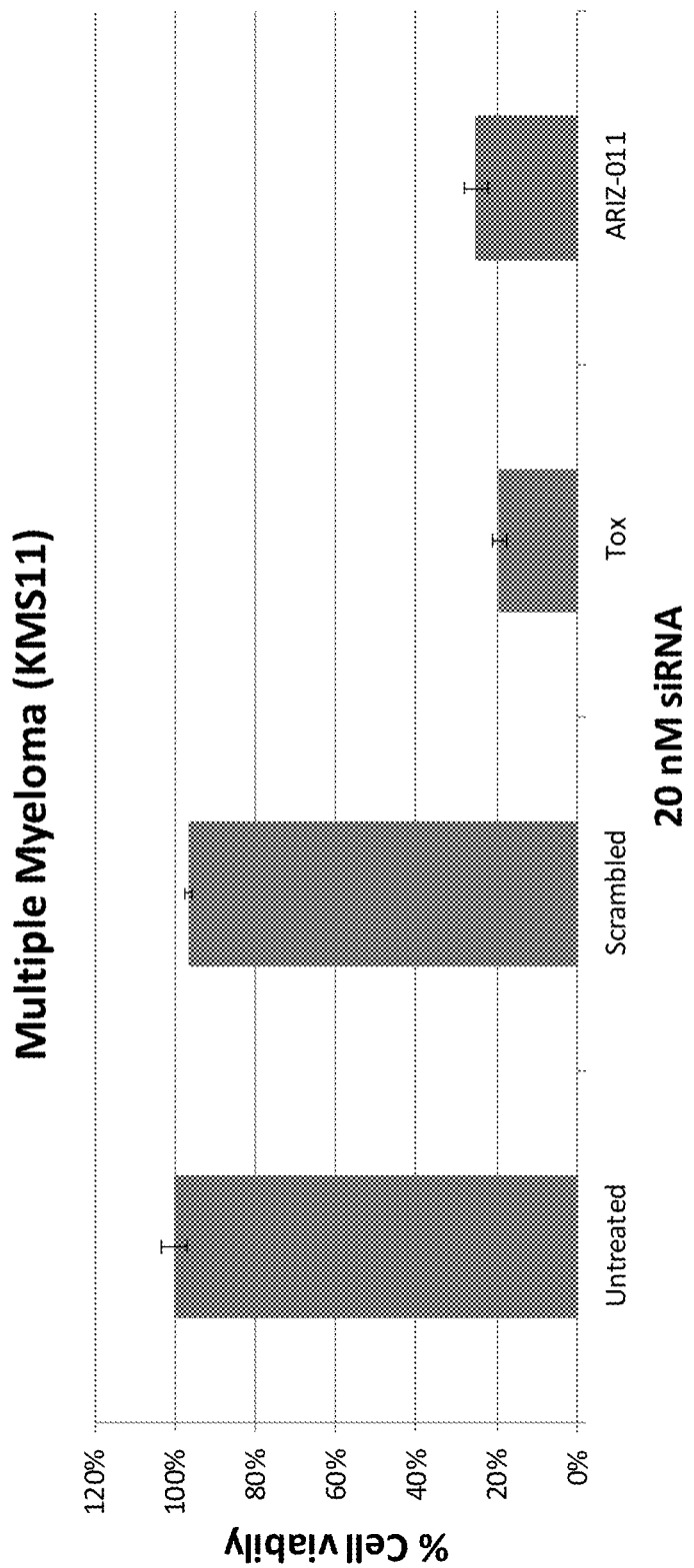
FIG. 8 depicts the percent viability of KMS11 multiple myeloma cells following treatment of the cells with ARIZ-011.

In this example, the effect of siRNA ARIZ-011 was further tested on a multiple myeloma cell line, KMS-11. KMS-11 cell line was obtained from commercially available sources, and was originally derived from four multiple myeloma patient's cells. These cells have characteristics of plasma cells. Using protocols similar to described in the previous sections, it was observed that ARIZ-011 was responsible for KMS-11 cell death in culture comparable to the Tox positive control, by about 80% (FIG. 8). These results indicate that ARIZ-011 is effective across multiple cancer cell lines, and can be a instrumental for development of a cancer therapeutic that targets a nodal point in cell cycle dysregulation and hyperproliferation.

Example 5: Targeted Drug Delivery Design

Figure 9:
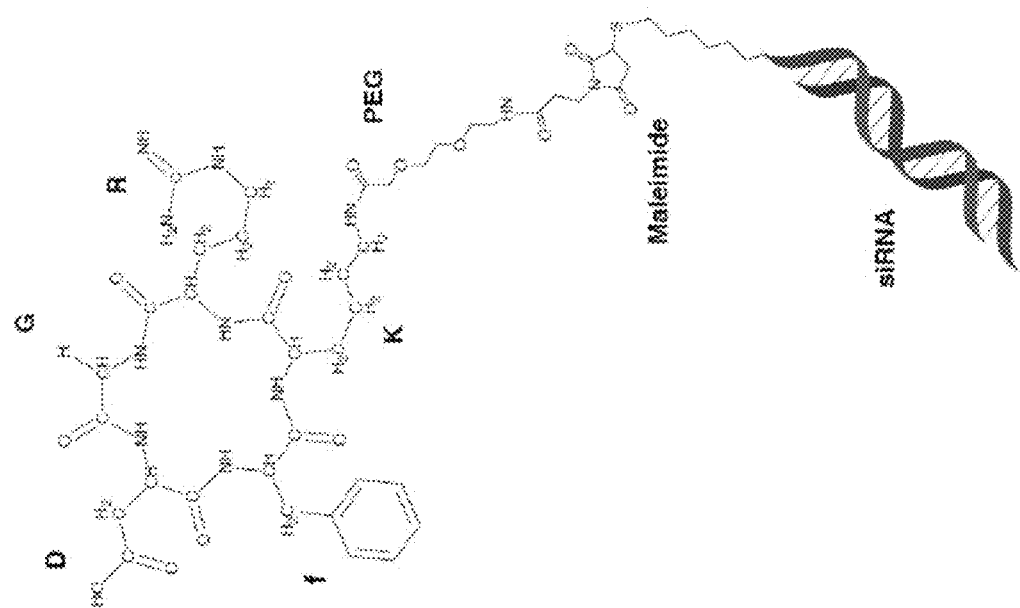
FIG. 9 depicts a c(RGDfk)-PEG-MAL-siRNA (SEQ ID NO: 23) construct that self-assembles to form a nanoparticle drug delivery system targeting the integrin $\alpha v\beta 3$ receptor.

An exemplary design is shown here for a targeted drug delivery system for cancer treatment with the siRNA disclosed herein. The carrier is a tumor-targeted, self-assembled peptide nanoparticle, consisting of a cyclic peptide targeting ligand conjugated to 8-amino-3,6-dioxaoctanoic acid-β-maleimidopropionic acid conjugated to an anti-RIZ siRNA, capable of delivering the siRNA payload specifically to cancer cells expressing the target receptor in an animal model.

siRNA ARIZ-047 described earlier in the document is conjugated to a RGDfk circular peptide (SEQ ID NO: 24) to form a (RGDfk)/siRNA (SEQ ID NO: 23) (FIG. 9). The siRNA is linked via a short linker to a PEG molecule, with the RGDfk (SEQ ID NO: 24) at the other end.

Example 6. Testing siRNA Efficacy In Vivo

Female athymic nude mice were used to prepare lung adenocarcinoma tumor model with A549 cells. The (RGDfk)/siRNA (SEQ ID NO: 23) injected intravenously once daily into mice bearing A549 lung cancer tumor xenografts. The mice are monitored for tumor size for the effect of c(RGDfk)/siRNA (SEQ ID NO: 23). At 14 days, mice were sacrificed and tumor was excised and evaluated. Blood and other tissues were harvested for mRNA levels for RIZ1, RIZ2 and other genes of interest are tested by RTPCR.

The use of a targeting agent as shown here, e.g., RGDfk-conjugated siRNA molecule ("RGDfK" disclosed as SEQ ID NO: 23) eliminates the need for a liposomal or other nanoparticle-type delivery system. This will reduce or avoid the toxicity associated with the use of liposomes or other types of nanoparticle delivery systems caused by their accumulation in the liver and other organs.

Example 7: In Vivo Delivery Using Liposomes

Targeted drug delivery system for cancer treatment, comprising a calcium phosphate nanoparticle displaying a targeting ligand is used in this exemplary study to deliver a PRDM2 siRNA payload specifically to cancer cells in an animal model.

Nanoparticles are prepared that carry ARIZ-047 and that can additionally display the targeting peptide c(RGDfk) (SEQ ID NO: 24) to target human A549 lung cancer cells, according to the methods described by Parette et al. (U.S. Pat. No. 10,226,424). Briefly, 21- or 25-base pair siRNA are first conjugated to PEG moieties. The phosphoamide chemistry involves conjugating siRNA with 5' $PO_4$ end groups to an amine-terminated methoxy PEG molecule while the thioether chemistry involves conjugating siRNA with 5'-sulfhydryl end groups to a maleimide-terminated methoxy PEG molecule. To achieve the phosphoamide conjugation, 0.12M N-(3-Dimethylaminopropyl)-N'-ethylcarbodiimide hydrochloride, 47.6 uM single stranded siRNA (inactive strand containing 5' $PO_4$ groups) and 0.238M amine-PEG are dissolved in 0.1M imidazole at pH 6 and incubated 18 hrs at 50 C. This reaction typically yields 15-30% conjugation. Alternatively, the addition of 0.1M MES buffer, pH 4, into the phosphoamide reaction mixture results in conjugation efficiency of 75-90%. For the thioether chemistry, 200 uM single stranded siRNA (inactive strand containing 5' $PO_4$ groups) is combined with 0.476M amine-PEG in the presence of 0.02M DTT in a 0.1M Tris HCl buffer and the reaction is incubated at 25 C 18 hrs. This reaction yields approximately 50% conjugation. These reactions have been performed using 2 kDa and 5 kDa PEG molecules. Following conjugation, the inactive (sense) strand is annealed to the unconjugated active (antisense) strand RNA in the reaction mix by heating to 70 C followed by slow cooling. For the highly efficient (75-90%) phosphoamide reaction, unconjugated, annealed siRNA containing either 5'$PO_4$ groups on both the active (anti sense) and inactive (sense) strand or one 5' $PO_4$ group on the active (antisense) strand are added to the reaction mixture to facilitate desalt purification, as described below. The presence of 5' $PO_4$ groups on the inactive (sense) strand results in a more negatively charged particle while the absence of these groups shifts the particle charge closer to neutral.

Particles are washed via centrifuge filtration with 5% dextrose containing calcium and phosphate to remove unincorporated siRNA and siRNA-PEG conjugates. Alternatively, unincorporated siRNA, Ca, Cl, Na and Pat can be removed from the suspension by ultracentrifugation at 132,000 g, which results in particle collection in the bottom 10% of the sample volume. Separation of the bottom 10% of the sample volume containing the particles reduces residual unincorporated components by up to 90%. Capture of the siRNA within the particle is sequence dependent and ranges from 10-25% of the siRNA added in the synthesis. The synthesis describe herein results in calcium phosphate nanoparticles containing siRNA with monomodal particle size distributions of ≤160 nm, as shown below.

Figure 10:
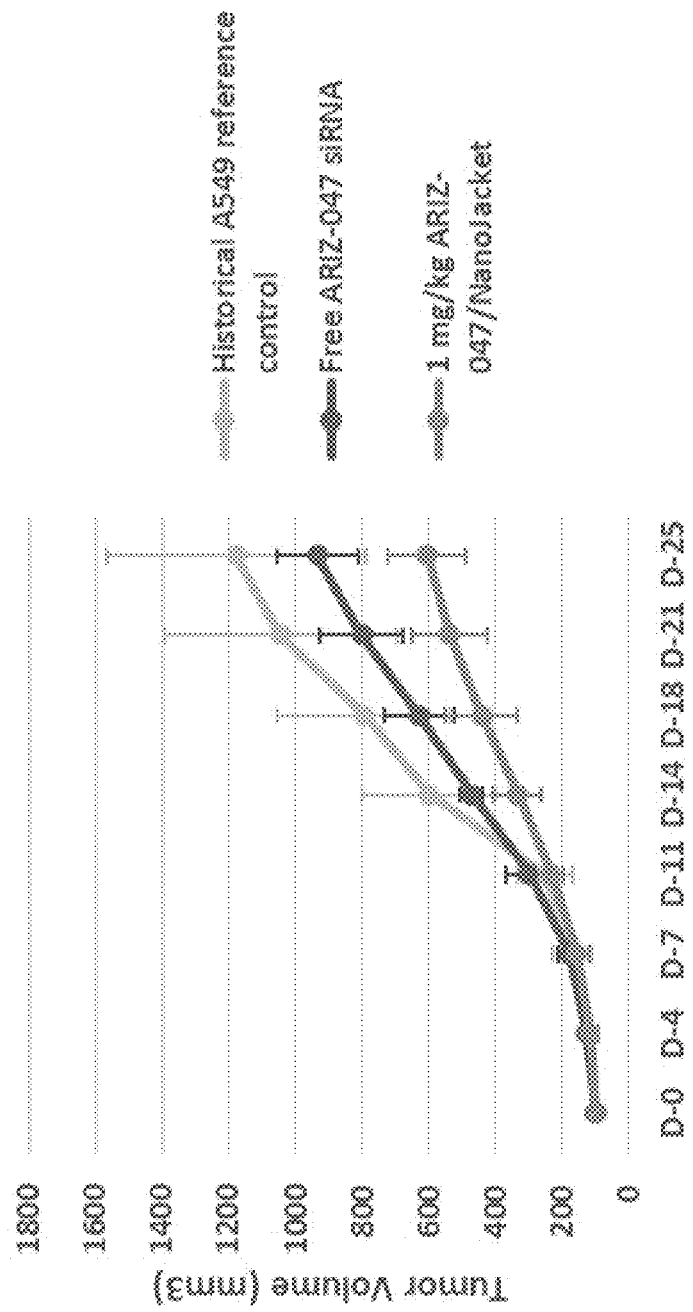
FIG. 10 depicts tumor and exemplary data showing tumor regression in A549 lung cancer xenograft model. siRNA (ARIZ-047) delivered in a nanoparticle shows the most promising effect on tumor growth control.

The nanoparticle preparations are administered intravenously to mice bearing A549 lung cancer tumor xenografts, where the xenografts as in the previous example. Mice were administered siRNA at a dose of 1 mg/Kg ARIZ-047 encapsulated in a nanoparticle described in the section. In some embodiments, these nanoparticles are termed "nanojackets." The mice are subsequently monitored for tumor size, and for any toxic effects of the treatment to determine therapeutic efficacy. Most surprisingly ARIZ-047 showed efficient control of tumor growth (FIG. 10) over a 25 day period observed. Tumor growth was suppressed by about 50% compared to no-siRNA reference control.

SEQUENCE LISTING

```
Sequence total quantity: 24
SEQ ID NO: 1            moltype = DNA  length = 21
FEATURE                 Location/Qualifiers
source                  1..21
                        mol_type = other DNA
                        organism = synthetic construct
                        note = Description of Artificial Sequence: Synthetic
                         oligonucleotide
                        note = Description of Combined DNA/RNA Molecule: Synthetic
                         oligonucleotide
misc_feature            1..19
                        note = RNA
misc_feature            20..21
                        note = DNA
SEQUENCE: 1
gggagagatg agagagaaat t                                                      21

SEQ ID NO: 2            moltype = DNA  length = 21
FEATURE                 Location/Qualifiers
source                  1..21
                        mol_type = other DNA
                        organism = synthetic construct
                        note = Description of Artificial Sequence: Synthetic
                         oligonucleotide
                        note = Description of Combined DNA/RNA Molecule: Synthetic
                         oligonucleotide
```

```
misc_feature              1..19
                          note = RNA
misc_feature              20..21
                          note = DNA
SEQUENCE: 2
gtgtagtgct gtaaagaaat t                                              21

SEQ ID NO: 3              moltype = DNA  length = 21
FEATURE                   Location/Qualifiers
source                    1..21
                          mol_type = other DNA
                          organism = synthetic construct
                          note = Description of Artificial Sequence: Synthetic
                           oligonucleotide
                          note = Description of Combined DNA/RNA Molecule: Synthetic
                           oligonucleotide
misc_feature              1..19
                          note = RNA
misc_feature              20..21
                          note = DNA
SEQUENCE: 3
gcaaaatgtc gtcgaataat t                                              21

SEQ ID NO: 4              moltype = DNA  length = 21
FEATURE                   Location/Qualifiers
source                    1..21
                          mol_type = other DNA
                          organism = synthetic construct
                          note = Description of Artificial Sequence: Synthetic
                           oligonucleotide
                          note = Description of Combined DNA/RNA Molecule: Synthetic
                           oligonucleotide
misc_feature              1..19
                          note = RNA
misc_feature              20..21
                          note = DNA
SEQUENCE: 4
tggaaaaggt gtcgacaatt t                                              21

SEQ ID NO: 5              moltype = DNA  length = 21
FEATURE                   Location/Qualifiers
source                    1..21
                          mol_type = other DNA
                          organism = synthetic construct
                          note = Description of Artificial Sequence: Synthetic
                           oligonucleotide
                          note = Description of Combined DNA/RNA Molecule: Synthetic
                           oligonucleotide
misc_feature              1..19
                          note = RNA
misc_feature              20..21
                          note = DNA
SEQUENCE: 5
ggacttcagg aacttcctgt t                                              21

SEQ ID NO: 6              moltype = DNA  length = 21
FEATURE                   Location/Qualifiers
source                    1..21
                          mol_type = other DNA
                          organism = synthetic construct
                          note = Description of Artificial Sequence: Synthetic
                           oligonucleotide
                          note = Description of Combined DNA/RNA Molecule: Synthetic
                           oligonucleotide
modified_base             1
                          mod_base = OTHER
                          note = 5'Disulfide guanosine
modified_base             9
                          mod_base = OTHER
                          note = 2'-methoxyuridine
misc_feature              1..19
                          note = RNA
misc_feature              20..21
                          note = DNA
SEQUENCE: 6
gggagagatg agagagaaat t                                              21

SEQ ID NO: 7              moltype = DNA  length = 21
FEATURE                   Location/Qualifiers
```

```
source                  1..21
                        mol_type = other DNA
                        organism = synthetic construct
                        note = Description of Artificial Sequence: Synthetic
                         oligonucleotide
                        note = Description of Combined DNA/RNA Molecule: Synthetic
                         oligonucleotide
misc_feature            1..19
                        note = RNA
misc_feature            20..21
                        note = DNA
SEQUENCE: 7
cttaataact agaggagaat t                                                 21

SEQ ID NO: 8            moltype = DNA  length = 20
FEATURE                 Location/Qualifiers
source                  1..20
                        mol_type = other DNA
                        organism = synthetic construct
                        note = Description of Artificial Sequence: Synthetic
                         oligonucleotide
                        note = Description of Combined DNA/RNA Molecule: Synthetic
                         oligonucleotide
misc_feature            1..18
                        note = RNA
misc_feature            19..20
                        note = DNA
SEQUENCE: 8
cgcaaaggat acgaaatctt                                                   20

SEQ ID NO: 9            moltype = DNA  length = 21
FEATURE                 Location/Qualifiers
source                  1..21
                        mol_type = other DNA
                        organism = synthetic construct
                        note = Description of Artificial Sequence: Synthetic
                         oligonucleotide
                        note = Description of Combined DNA/RNA Molecule: Synthetic
                         oligonucleotide
misc_feature            1..19
                        note = RNA
misc_feature            20..21
                        note = DNA
SEQUENCE: 9
ggataagcac tacggcaaat t                                                 21

SEQ ID NO: 10           moltype = DNA  length = 21
FEATURE                 Location/Qualifiers
source                  1..21
                        mol_type = other DNA
                        organism = synthetic construct
                        note = Description of Artificial Sequence: Synthetic
                         oligonucleotide
                        note = Description of Combined DNA/RNA Molecule: Synthetic
                         oligonucleotide
misc_feature            1..19
                        note = RNA
misc_feature            20..21
                        note = DNA
SEQUENCE: 10
tttctctctc atctctccct t                                                 21

SEQ ID NO: 11           moltype = DNA  length = 21
FEATURE                 Location/Qualifiers
source                  1..21
                        mol_type = other DNA
                        organism = synthetic construct
                        note = Description of Artificial Sequence: Synthetic
                         oligonucleotide
                        note = Description of Combined DNA/RNA Molecule: Synthetic
                         oligonucleotide
modified_base           1
                        mod_base = OTHER
                        note = Phosphate 2'-methoxyuridine
modified_base           2
                        mod_base = OTHER
                        note = 2'-methoxyuridine
modified_base           3
                        mod_base = OTHER
```

```
                              note = 2'-fluoro-deoxyuridine
modified_base                 5
                              mod_base = OTHER
                              note = 2'-fluoro-deoxyuridine
modified_base                 7
                              mod_base = OTHER
                              note = 2'-fluoro-deoxyuridine
modified_base                 14
                              mod_base = OTHER
                              note = 2'-fluoro-deoxyuridine
modified_base                 16
                              mod_base = OTHER
                              note = 2'-fluoro-deoxyuridine
modified_base                 19
                              mod_base = OTHER
                              note = Cytidine phosphorothioate
modified_base                 20
                              mod_base = OTHER
                              note = Deoxythymidine phosphorothioate
modified_base                 21
                              mod_base = OTHER
                              note = Deoxythymidine phosphorothioate
misc_feature                  1..2
                              note = RNA
misc_feature                  3
                              note = DNA
misc_feature                  4
                              note = RNA
misc_feature                  5
                              note = DNA
misc_feature                  6
                              note = RNA
misc_feature                  7
                              note = DNA
misc_feature                  8..13
                              note = RNA
misc_feature                  14
                              note = DNA
misc_feature                  15
                              note = RNA
misc_feature                  16
                              note = DNA
misc_feature                  17..19
                              note = RNA
misc_feature                  20..21
                              note = DNA
SEQUENCE: 11
tttctctctc atctctccct t                                                   21

SEQ ID NO: 12                 moltype = DNA  length = 21
FEATURE                       Location/Qualifiers
source                        1..21
                              mol_type = other DNA
                              organism = synthetic construct
                              note = Description of Artificial Sequence: Synthetic
                               oligonucleotide
                              note = Description of Combined DNA/RNA Molecule: Synthetic
                               oligonucleotide
misc_feature                  1..19
                              note = RNA
misc_feature                  20..21
                              note = DNA
SEQUENCE: 12
tttctttaca gcactacact t                                                   21

SEQ ID NO: 13                 moltype = DNA  length = 21
FEATURE                       Location/Qualifiers
source                        1..21
                              mol_type = other DNA
                              organism = synthetic construct
                              note = Description of Artificial Sequence: Synthetic
                               oligonucleotide
                              note = Description of Combined DNA/RNA Molecule: Synthetic
                               oligonucleotide
misc_feature                  1..19
                              note = RNA
misc_feature                  20..21
                              note = DNA
SEQUENCE: 13
```

```
ttattcgacg acattttgct t                                              21

SEQ ID NO: 14           moltype = DNA  length = 21
FEATURE                 Location/Qualifiers
source                  1..21
                        mol_type = other DNA
                        organism = synthetic construct
                        note = Description of Artificial Sequence: Synthetic
                         oligonucleotide
                        note = Description of Combined DNA/RNA Molecule: Synthetic
                         oligonucleotide
misc_feature            1..19
                        note = RNA
misc_feature            20..21
                        note = DNA
SEQUENCE: 14
attgtcgaca cctttttccat t                                             21

SEQ ID NO: 15           moltype = DNA  length = 21
FEATURE                 Location/Qualifiers
source                  1..21
                        mol_type = other DNA
                        organism = synthetic construct
                        note = Description of Artificial Sequence: Synthetic
                         oligonucleotide
                        note = Description of Combined DNA/RNA Molecule: Synthetic
                         oligonucleotide
misc_feature            1..19
                        note = RNA
misc_feature            20..21
                        note = DNA
SEQUENCE: 15
caggaagttc ctgaagtcct t                                              21

SEQ ID NO: 16           moltype = DNA  length = 21
FEATURE                 Location/Qualifiers
source                  1..21
                        mol_type = other DNA
                        organism = synthetic construct
                        note = Description of Artificial Sequence: Synthetic
                         oligonucleotide
                        note = Description of Combined DNA/RNA Molecule: Synthetic
                         oligonucleotide
modified_base           1
                        mod_base = OTHER
                        note = Phosphate uridine
misc_feature            1..19
                        note = RNA
misc_feature            20..21
                        note = DNA
SEQUENCE: 16
ttctcctcta gttattaagt t                                              21

SEQ ID NO: 17           moltype = DNA  length = 21
FEATURE                 Location/Qualifiers
source                  1..21
                        mol_type = other DNA
                        organism = synthetic construct
                        note = Description of Artificial Sequence: Synthetic
                         oligonucleotide
                        note = Description of Combined DNA/RNA Molecule: Synthetic
                         oligonucleotide
modified_base           1
                        mod_base = OTHER
                        note = Phosphate guanosine
misc_feature            1..19
                        note = RNA
misc_feature            20..21
                        note = DNA
SEQUENCE: 17
gattccgtat cctttgccgt t                                              21

SEQ ID NO: 18           moltype = DNA  length = 21
FEATURE                 Location/Qualifiers
source                  1..21
                        mol_type = other DNA
                        organism = synthetic construct
                        note = Description of Artificial Sequence: Synthetic
                         oligonucleotide
```

```
                         note = Description of Combined DNA/RNA Molecule: Synthetic
                          oligonucleotide
modified_base            1
                         mod_base = OTHER
                         note = Phosphate uridine
misc_feature             1..19
                         note = RNA
misc_feature             20..21
                         note = DNA
SEQUENCE: 18
tttgccgtag tgcttatcct t                                                    21

SEQ ID NO: 19            moltype = AA   length = 201
FEATURE                  Location/Qualifiers
source                   1..201
                         mol_type = protein
                         organism = Homo sapiens
SEQUENCE: 19
MNQNTTEPVA ATETLAEVPE HVLRGLPEEV RLFPSAVDKT RIGVWATKPI LKGKKFGPFV    60
GDKKKRSQVK NNVYMWEVYY PNLGWMCIDA TDPEKGNWLR YVNWACSGEE QNLFPLEINR   120
AIYYKTLKPI APGEELLVWY NGEDNPEIAA AIEEERASAR SKRSSPKSRK GKKKSQENKN   180
KGNKIQDIQL KTSEPDFTSA N                                             201

SEQ ID NO: 20            moltype = AA   length = 1481
FEATURE                  Location/Qualifiers
source                   1..1481
                         mol_type = protein
                         organism = Homo sapiens
SEQUENCE: 20
MRDSAEGPKE DEEKPSASAL EQPATLQEVA SQEVPPELAT PAPAWEPQPE PDERLEAAAC    60
EVNDLGEEEE EEEEEDEEEE EDDDDDELED EGEEEASMPN ENSVKEPEIR CDEKPEDLLE   120
EPKTTSEETL EDCSEVTPAM QIPRTKEEAN GDVFETFMFP CQHCERKFTT KQGLERHMHI   180
HISTVNHAFK CKYCGKAFGT QINRRRHERR HEAGLKRKPS QTLQPSEDLA DGKASGENVA   240
SKDDSSPPSL GPDCLIMNSE KASQDTINSS VVEENGEVKE LHPCKYCKKV FGTHTNMRRH   300
QRRVHERHLI PKGVRRKGGL EEPQPPAEQA QATQNVYVPS TEPEEEGEAD DVYIMDISSN   360
ISENLNYYID GKIQTNNNTS NCDVIEMESA SADLYGINCL LTPVTVEITQ NIKTTQVPVT   420
EDLPKEPLGS TNSEAKKRRT ASPPALPKIK AETDSDPMVP SCSLSLPLSI STTEAVSFHK   480
EKSVYLSSKL KQLLQTQDKL TPAGISATEI AKLGPVCVSA PASMLPVTSS RFKRRTSSPP   540
SSPQHSPALR DFGKPSDGKA AWTDAGLTSK KSKLESHSDS PAWSLSGRDE RETVSPPCFD   600
EYKMSKEWTA SSAFSSVCNQ QPLDLSSGVK QKAEGTGKTP VQWESVLDLS VHKKHCSDSE   660
GKEFKESHSV QPTCSAVKKR KPTTCMLQKV LLNEYNGIDL PVENPADGTR SPSPCKSLEA   720
QPDPDLGPGS GFPAPTVEST PDVCPSSPAL QTPSLSSGQL PPLLIPTDPS SPPPCPPVLT   780
VATPPPPLLP TVPLPAPSSS ASPHPCPSPL SNATAQSPLP ILSPTVSPSP SPIPPVEPLM   840
SAASPGPPTL SSSSSSSSSS SSFSSSSSSS SPSPPPLSAI SSVVSSGDNL EASLPMISFK   900
QEELENEGLK PREEPQSAAE QDVVVQETFN KNFVCNVCES PFLSIKDLTK HLSIHAEEWP   960
FKCEFCVQLF KDKTDLSEHR FLLHGVGNIF VCSVCKKEFA FLCNLQQHQR DLHPDKVCTH  1020
HEFESGTLRP QNFTDPSKAH VEHMQSLPED PLETSKEEEE LNDSSEELYT TIKIMASGIK  1080
TKDPDVRLGL NQHYPSFKPP PFQYHHRNPM GIGVTATNFT THNIPQTFTT AIRCTKCGKG  1140
VDNMPELHKH ILACASASDK KRYTPKKNPV PLKQTVQPKN GVVVLDNSGK NAFRRMGQPK  1200
RLNFSVELSK MSSNKLKLNA LKKKNQLVQK AILQKNKSAK QKADLKNACE SSSHICPYCN  1260
REFTYIGSLN KHAAFSCPKK PLSPPKKKVS HSSKKGGHSS PASSDKNSNS NHRRRTADAE  1320
IKMQSMQTPL GKTRARSSGP TQVPLPSSSF RSKQNVKFAA SVKSKKPSSS SLRNSSPIRM  1380
AKITHVEGKK PKAVAKNHSA QLSSKTSRSL HVRVQKSKAV LQSKSTLASK KRTDRFNIKS  1440
RERSGGPVTR SLQLAAAADL SENKREDGSA KQELKDFRNF L                      1481

SEQ ID NO: 21            moltype = AA   length = 1477
FEATURE                  Location/Qualifiers
source                   1..1477
                         mol_type = protein
                         organism = Homo sapiens
SEQUENCE: 21
MRDSAEGPKE DEEKPSASAL EQPATLQEVA SQEVPPELAT PAPAWEPQPE PDERLEAAAC    60
EVNDLGEEEE EEEEEDEEEE EDDDDDELED EGEEEASMPN ENSVKEPEIR CDEKPEDLLE   120
EPKTTSEETL EDCSEVTPAM QIPRTKEEAN GDVFETFMFP CQHCERKFTT KQGLERHMHI   180
HISTVNHAFK CKYCGKAFGT QINRRRHERR HEAGLKRKPS QTLQPSEDLA DGKASGENVA   240
SKDDSSPPSL GPDCLIMNSE KASQDTINSS VVEENGEVKE LHPCKYCKKV FGTHTNMRRH   300
QRRVHERHLI PKGVRRKGGL EEPQPPAEQA QATQNVYVPS TEPEEEGEAD DVYIMDISSN   360
ISENLNYYID GKIQTNNNTS NCDVIEMESA SADLYGINCL LTPVTVEITQ NIKTTQVPVT   420
EDLPKEPLGS TNSEAKKRRT ASPPALPKIK AETDSDPMVP SCSLSLPLSI STTEAVSFHK   480
EKSVYLSSKL KQLLQTQDKL TPAGISATEI AKLGPVCVSA PASMLPVTSS RFKRRTSSPP   540
SSPQHSPALR DFGKPSDGKA AWTDAGLTSK KSKLESHSDS PAWSLSGRDE RETVSPPCFD   600
EYKMSKEWTA SSAFSSVCNQ QPLDLSSGVK QKAEGTGKTP VQWESVLDLS VHKKHCSDSE   660
GKEFKESHSV QPTCSAVKKR KPTTCMLQKV LLNEYNGIDL PVENPADGTR SPSPCKSLEA   720
QPDPDLGPGS GFPAPTVEST PDVCPSSPAL QTPSLSSGQL PPLLIPTDPS SPPPCPPVLT   780
VATPPPPLLP TVPLPAPSSS ASPHPCPSPL SNATAQSPLP ILSPTVSPSP SPIPPVEPLM   840
SAASPGPPTL SSSSSSSSSS SSFSSSSSSS SPSPPPLSAI SSVVSSGDNL EASLPMISFK   900
QEELENEGLK PREEPQSAAE QDVVVQETFN KNFVCNVCES PFLSIKDLTK HLSIHAEEWP   960
FKCEFCVQLF KDKTDLSEHR FLLHGVGNIF VCSVCKKEFA FLCNLQQHQR DLHPDKVCTH  1020
HEFESGTLRP QNFTDPSKAH VEHMQSLPED PLETSKEEEE LNDSSEELYT TIKIMASGIK  1080
```

```
TKDPDVRLGL NQHYPSFKPP PFQYHHRNPM GIGVTATNFT THNIPQTFTT AIRCTKCGKG    1140
VDNMPELHKH ILACASASDK KRYTPKKNPV PLKQTVQPKN GVVVLDNSGK NAFRRMGQPK    1200
RLNFSVELSK MSSNKLKLNA LKKKNQLVQK AILQKNKSAK QKADLKNACE SSSHICPYCN    1260
REFTYIGSLN KHAAFSCPKK PLSPPKKKVS HSSKKGGHSS PASSDKNSNS NHRRRTADAE    1320
IKMQSMQTPL GKTRARSSGP TQVPLPSSSF RSKQNVKFAA SVKSKKPSSS SLRNSSPIRM    1380
AKITHVEGKK PKAVAKNHSA QLSSKTSRSL HVRVQKSKAV LQSKSTLASK KRTDRFNIKS    1440
RERSGGPVTR SLQLAAAADL SENKREDGSA KQELKDF                             1477

SEQ ID NO: 22           moltype = AA   length = 1477
FEATURE                 Location/Qualifiers
source                  1..1477
                        mol_type = protein
                        organism = Homo sapiens
SEQUENCE: 22
MRDSAEGPKE DEEKPSASAL EQPATLQEVA SQEVPPELAT PAPAWEPQPE PDERLEAAAC     60
EVNDLGEEEE EEEEEDEEEE EDDDDDELED EGEEEASMPN ENSVKEPEIR CDEKPEDLLE    120
EPKTTSEETL EDCSEVTPAM QIPRTKEEAN GDVFETFMFP CQHCERKFTT KQGLERHMHI    180
HISTVNHAFK CKYCGKAFGT QINRRRHERR HEAGLKRKPS QTLQPSEDLA DGKASGENVA    240
SKDDSSPPSL GPDCLIMNSE KASQDTINSS VVEENGEVKE LHPCKYCKKV FGTHTNMRRH    300
QRRVHERHLI PKGVRRKGGL EEPQPPAEQA QATQNVYVPS TEPEEEGEAD DVYIMDISSN    360
ISENLNYYID GKIQTNNNTS NCDVIEMESA SADLYGINCL LTPVTVEITQ NIKTTQVPVT    420
EDLPKEPLGS TNSEAKKRRT ASPPALPKIK AETDSDPMVP SCSLSLPLSI STTEAVSFHK    480
EKSVYLSSKL KQLLQTQDKL TPAGISATEI AKLGPVCVSA PASMLPVTSS RFKKRTSSPP    540
SSPQHSPALR DFGKPSDGKA AWTDAGLTSK KSKLESHSDS PAWSLSGRDE RETVSPPCFD    600
EYKMSKEWTA SSAFSSVCNQ QPLDLSSGVK QKAEGTGKTP VQWESVLDLS VHKKHCSDSE    660
GKEFKESHSV QPTCSAVKKR KPTTCMLQKV LLNEYNGIDL PVENPADGTR SPSPCKSLEA    720
QPDPDLGPGS GFPAPTVEST PDVCPSSPAL QTPSLSSGQL PPLLIPTDPS SPPPCPPVLT    780
VATPPPPLLP TVPLPAPSSS ASPHPCPSPL SNATAQSPLP ILSPTVSPSP SPIPPVEPLM    840
SAASPGPPTL SSSSSSSSSS SSFSSSSSSS SPSPPPLSAI SSVVSSGDNL EASLPMISFK    900
QEELENEGLK PREEPQSAAE QDVVVQETFN KNFVCNVCES PFLSIKDLTK HLSIHAEEWP    960
FKCEFCVQLF KDKTDLSEHR FLLHGVGNIF VCSVCKKEFA FLCNLQQHQR DLHPDKVCTH   1020
HEFESGTLRP QNFTDPSKAH VEHMQSLPED PLETSKEEEE LNDSSEELYT TIKIMASGIK   1080
TKDPDVRLGL NQHYPSFKPP PFQYHHRNPM GIGVTATNFT THNIPQTFTT AIRCTKCGKG   1140
VDNMPELHKH ILACASASDK KRYTPKKNPV PLKQTVQPKN GVVVLDNSGK NAFRRMGQPK   1200
RLNFSVELSK MSSNKLKLNA LKKKNQLVQK AILQKNKSAK QKADLKNACE SSSHICPYCN   1260
REFTYIGSLN KHAAFSCPKK PLSPPKKKVS HSSKKGGHSS PASSDKNSNS NHRRRTADAE   1320
IKMQSMQTPL GKTRARSSGP TQVPLPSSSF RSKQNVKFAA SVKSKKPSSS SLRNSSPIRM   1380
AKITHVEGKK PKAVAKNHSA QLSSKTSRSL HVRVQKSKAV LQSKSTLASK KRTDRFNIKS   1440
RERSGGPVTR SLQLAAAADL SENKREDGSA KQELKDF                            1477

SEQ ID NO: 23           moltype = AA   length = 5
FEATURE                 Location/Qualifiers
source                  1..5
                        mol_type = protein
                        organism = synthetic construct
SITE                    4
                        note = D-Phenylalanine
SITE                    5
                        note = Lysine attached to an siRNA molecule via a
                          polyethylene glycol-maleimide linker
REGION                  1..5
                        note = Cyclic peptide wherein the N-terminus of the
                          Arginine is linked to the C-terminus of the Lysine
SEQUENCE: 23
RGDFK                                                                  5

SEQ ID NO: 24           moltype = AA   length = 5
FEATURE                 Location/Qualifiers
source                  1..5
                        mol_type = protein
                        organism = synthetic construct
SITE                    4
                        note = D-Phenylalanine
REGION                  1..5
                        note = Cyclic peptide wherein the N-terminus of the
                          Arginine is linked to the C-terminus of the Lysine
SEQUENCE: 24
RGDFK                                                                  5
```

We claim:

1. A pharmaceutical composition comprising: a RIZ2 inhibitor, comprising a double stranded siRNA molecule having 10-21 nucleotides that have complementarity to human PRDM2/RIZ2 gene; (b) a pharmaceutically acceptable excipient, and (c) a drug delivery vehicle comprising a nanoparticle;
   wherein the double stranded siRNA comprises a sense strand having the sequence 5'-Disulfide-GGGAGAGA4GAGAGAGAAAdTdT-3' (SEQ ID NO: 6), and an antisense strand having the sequence 5'P-446C6C6CUCAUC6C6CCCdTdT-3' (SEQ ID NO: 11), wherein, 4 is 2'-methoxyuridine; 6 is 2'-Fluorodeoxyuridine; bold+underline represents phosphorothioate.

2. The pharmaceutical composition of claim 1, further comprising a PEG molecule.

3. The pharmaceutical composition of claim 1, wherein the nanoparticle comprises a calcium phosphate complex incorporating the RIZ2 inhibitor.

4. The pharmaceutical composition of claim 1, further comprising one or more chemotherapeutic drugs.

5. The pharmaceutical composition of claim 1, further comprising a cell targeting moiety.

6. The pharmaceutical composition of claim 5, wherein the cell targeting moiety is an aptamer.

7. The pharmaceutical composition of claim 1, wherein the nanoparticle comprises a calcium phosphosilicate complex incorporating the RIZ2 inhibitor.

8. A pharmaceutical composition comprising:
   (i) a calcium phosphate nanoparticle,
   (ii) a double stranded siRNA molecule, encapsulated by the nanoparticle, wherein the double stranded siRNA molecule comprises (a) a sense strand having the sequence: 5'-Disulfide-GGGAGAGA4GAGAGAGAAAdTdT-3' (SEQ ID NO: 6), wherein 4 is 2'-methoxyuridine, and (b) an antisense strand having the sequence: 5'P-446C6C6CUCAUC6C6CCCdTdT-3' (SEQ ID NO: 11), wherein, 4 is 2'-methoxyuridine; 6 is 2'-Fluorodeoxyuridine; bold+underline represents phosphorothioate;
   (iii) a PEG molecule, and
   (iv) a cell targeting moiety;
   wherein the pharmaceutical composition is formulated for systemic delivery to a subject in need thereof.

* * * * *

UNITED STATES PATENT AND TRADEMARK OFFICE
CERTIFICATE OF CORRECTION

PATENT NO. : 12,012,597 B2
APPLICATION NO. : 17/945739
DATED : June 18, 2024
INVENTOR(S) : Lonnie L. Bookbinder et al.

Page 1 of 1

It is certified that error appears in the above-identified patent and that said Letters Patent is hereby corrected as shown below:

In the Claims

Column 59, Line 11, Claim 1:
"5'P-446C6C6CUCAUC6C6CCCdTdT-3' (SEQ ID NO:" should read
-- 5'P 446C6C6CUCAUC6C6CCCdTdT-3' (SEQ ID NO: --

Column 60, Line 15, Claim 8:
"446C6C6CUCAUC6C6CCCdTdT-3' (SEQ ID NO:" should read
-- 446C6C6CUCAUC6C6CCCdTdT-3' (SEQ ID NO: --

Signed and Sealed this
Third Day of December, 2024

*Katherine Kelly Vidal*
Katherine Kelly Vidal
*Director of the United States Patent and Trademark Office*